US012774498B2

(12) United States Patent
Venturelli et al.

(10) Patent No.: US 12,774,498 B2
(45) Date of Patent: Oct. 27, 2026

(54) CELL-BASED DNA SENSORS AND METHODS OF USING SAME

(71) Applicant: Wisconsin Alumni Research Foundation, Madison, WI (US)

(72) Inventors: Ophelia Venturelli, Madison, WI (US); Yu-Yu Cheng, Madison, WI (US); Zhengyi Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 885 days.

(21) Appl. No.: 18/067,194

(22) Filed: Dec. 16, 2022

(65) Prior Publication Data

US 2024/0026466 A1 Jan. 25, 2024

Related U.S. Application Data

(60) Provisional application No. 63/290,442, filed on Dec. 16, 2021.

(51) Int. Cl.

| | |
|---|---|
| ***C12Q 1/689*** | (2018.01) |
| ***C12N 15/90*** | (2006.01) |
| ***C12Q 1/6897*** | (2018.01) |

(52) U.S. Cl.

CPC ........... *C12Q 1/689* (2013.01); *C12N 15/902* (2013.01); *C12Q 1/6897* (2013.01)

(58) Field of Classification Search

CPC ..... C12Q 1/689; C12Q 1/6897; C12N 15/902

See application file for complete search history.

(56) References Cited

FOREIGN PATENT DOCUMENTS

GB 2563577 A * 12/2018 ............ C12M 25/01

OTHER PUBLICATIONS

Popp, P.F. et al. Scientific Reports 7:14058 (DOI:10.1038/s41598-017-15107-z), 13 pages. Nov. 2017. (Year: 2017).*

Pearce, S.C. et al. Microbiology 163:462-471 (DOI 10.1099/mic.0.000446). (Year: 2017).*

"Interstitial Definition & Meaning—Merriam-Webster", Merriam-Webster, Incorporated, 1 page. (Year: 2026).*

Altschul et al., Basic Local Alignment Search Tool, *J. Mol. Biol.* 215:403-410 (1990).

Bai, J., Luo, Y., Wang, X et al. A protein-independent fluorescent RNA aptamer reporter system for plant genetic engineering. *Nat Commun* 11, 3847 (2020).

(Continued)

*Primary Examiner* — Diana B Johannsen

(74) *Attorney, Agent, or Firm* — Daniel A. Blasiole; DeWitt LLP

(57) ABSTRACT

Cell-based DNA sensors, compositions comprising the cell-based DNA sensors, and methods of detecting DNA and cells. The cell-based DNA sensors include competent cells that include genetic circuits. Each genetic circuit includes homology arms separated by an interstitial region that comprises at least one element of a reporter switch and/or a kill switch. The compositions include one or more cell-based DNA sensors. The cell-based DNA sensors can be used to detect DNA and cells by the genetic circuits undergoing homologous recombination with target regions of target DNA to activate or deactivate the reporter switch and/or kill switch.

19 Claims, 37 Drawing Sheets
(37 of 37 Drawing Sheet(s) Filed in Color)

Specification includes a Sequence Listing.

(56) References Cited

OTHER PUBLICATIONS

Benders GA, Noskov VN, Denisova EA, et al. Cloning whole bacterial genomes in yeast. Nucleic Acids Res. 2010;38(8):2558-2569.
Benoist et al. In vivo sequence requirements of the SV40 early promoter region, (1981) *Nature* (London) 290:304.
Berg, S. et al. ilastik: interactive machine learning for (bio)image analysis. Nat. Methods 16, 1226-1232 (2019).
Bitter et al. Expression and Secretion Vectors for Yeast, (1987) *Methods in Enzymology*, 153:516-544.
Burian, J. et al. High-throughput retrieval of target sequences from complex clone libraries using CRISPRi. Nat. Biotechnol. 2022 1-5 (2022). doi:10.1038/s41587-022-01531-8.
Carrasco, B., Serrano, E., Martín-González, A., Moreno-Herrero, F. & Alonso, J. C. Bacillus subtilis MutS modulates RecA-mediated DNA strand exchange between divergent DNA sequences. Front. Microbiol. (2019).doi: 10.3389/fmicb.2019.00237.
Cheng, Y.- Y., Papadopoulos, J. M., Falbel, T., Burton, B. M. & Venturelli, O. S. Donor-recipient interactions drive dynamics of horizontal gene transfer via natural competence. bioRxiv 2020.10.19.342733 (2020). doi:10.1101/2020.10.19.342733.
Cooper, R. M. et al. Engineered bacteria detect tumor DNA in vivo. *bioRxiv* 2021.09.10.459858 (2021). doi:10.1101/2021.09.10.459858.
Foecking et al. Powerful and versatile enhancer-promoter unit for mammalian expression vectors, (1980) *Gene* 45:101.
Glick and Whitney. Factors affecting the expression of foreign proteins in *Escherichia coli, J. Ind. Microbiol.* 1:277 (1987).
Hamer et al. Regulation in vivo of a cloned mammalian gene: cadmium induces the transcription of a mouse metallothionein gene in SV40 vectors, (1982) *J. Mol. Appl. Genet.* 1:273.
Henikoff & Henikoff (1989) Proc. Natl. Acad. Sci. USA 89:10915.
Ibáñez de Aldecoa, A. L., Zafra, O. & González-Pastor, J. E. Mechanisms and regulation of extracellular DNA release and its biological roles in microbial communities. *Front. Microbiol.* 8, 1390 (2017).
Itaya, M., Fujita, K., Kuroki, A et al. Bottom-up genome assembly using the Bacillus subtilis genome vector. Nat Methods 5, 41-43 (2008).
Johnston et al. Isolation of the yeast regulatory gene GAL4 and analysis of its dosage effects on the galactose/melibiose regulon, (1982) *PNAS* (USA) 79:6971.
Johnston, C., Martin, B., Fichant, G., Polard, P., and Claverys, J. P. (2014). Bacterial transformation: distribution, shared mechanisms and divergent control. *Nat. Rev. Microbiol.* 12, 181-196.
Khasanov FK, Zvingila DJ, Zainullin AA, Prozorov AA, Bashkirov VI. Homologous recombination between plasmid and chromosomal DNA in Bacillus subtilis requires approximately 70 bp of homology. Mol Gen Genet. Sep. 1992;234(3):494-7.
Levskaya, A. et al. Engineering *Escherichia coli* to see light. Nature 438, 441-442 (2005).
Liu, F., Li, J., Zhang, T., Chen, J. & Ho, C. L. Engineered Spore-Forming Bacillus as a Microbial Vessel for Long-Term DNA Data Storage. ACS Synth. Biol. (2022).
Doi: 10.1021/ACSSYNBIO.2C00291/SUPPL_FILE/SB2C00291_SI_001.PDF.
Liu, Y., Wan, X. & Wang, B. Engineered CRISPRa enables programmable eukaryote-like gene activation in bacteria. Nat Commun 10, 3693 (2019).
Lorenz, M. G., Gerjets, D. & Wackernagel, W. Release of transforming plasmid and chromosomal DNA from two cultured soil bacteria. Arch. Microbiol. 156, 319-326 (1991).
Maamar, H. & Dubnau, D. Bistability in the Bacillus subtilis K-state (competence) system requires a positive feedback loop. Mol. Microbiol. (2005). doi: 10.1111/j.1365-2958.2005.04592.x.
Matsui, K., Ishii, N. & Kawabata, Z. Release of extracellular transformable plasmid DNA from *Escherichia coli* cocultivated with algae. Appl. Environ. Microbiol. 69, 2399-2404 (2003).
Mitsuhiro Itaya, Shinya Kaneko, Integration of stable extracellular DNA released from *Escherichia coli* into the Bacillus subtilis genome vector by culture mix method, Nucleic Acids Research, vol. 38, Issue 8, May 1, 2010, pp. 2551-2557.
McKnight. Functional relationships between transcriptional control signals of the thymidine kinase gene of herpes simplex virus, (1982) *Cell* 31:355.
Needleman & Wunsch, A general method applicable to the search for similarities in the amino acid sequence of two proteins, J. Mol. Biol. 48:443 (1970).
Orlandi et al. Cloning immunoglobulin variable domains for expression by the polymerase chain reaction, (1989) *PNAS* (USA) 86:3833).
Overkamp, W. et al. Benchmarking various green fluorescent protein variants in Bacillus subtilis, *Streptococcus pneumoniae*, and Lactococcus lactis for live cell imaging. Appl. Environ. Microbiol. 79, 6481-6490 (2013).
Pearson & Lipman, Improved tools for biological sequence comparison, Proc. Nat'l. Acad. Sci. USA 85:2444 (1988).
Rahmer, R., Heravi, K. M. & Altenbuchner, J. Construction of a super-competent Bacillus subtilis 168 using the PmtlA-comKS inducible cassette. Front. Microbiol. 6, 1431 (2015).
Rasmussen, M. D., Martinussen, J., Defoor, E. M. C. & Poulsen, G. B. A counter-selectable marker for Bacillus. *Microb. Cell Factories* 2006 51 5, 1-1 (2006).
Reyrat, J M et al. "Counterselectable markers: untapped tools for bacterial genetics and pathogenesis." Infection and immunity vol. 66,9 (1998): 4011-7.
Sheth, R. U. & Wang, H. H. DNA-based memory devices for recording cellular events. Nature Reviews Genetics (2018). doi:10.1038/s41576-018-0052-8.
Silver et al. Amino terminus of the yeast GAL4 gene product is sufficient for nuclear localization, (1984) *PNAS* (USA) 81:5951.
Smith & Waterman, Comparison of Biosequences, Adv. Appl. Math. 2:482 (1981).
Tam, N. K. M. et al. The intestinal life cycle of Bacillus subtilis and close relatives. J. Bacteriol. (2006). doi:10.1128/JB.188.7.2692-2700.2006.
Zhang, X. et al. Stress-induced, highly efficient, donor cell-dependent cell-to-cell natural transformation in Bacillus subtilis. J. Bacteriol. 200, e00267-18 (2018).
Zhang, X.-Z. & Zhang, Y.- H. P. Simple, fast and high-efficiency transformation system for directed evolution of cellulase in Bacillus subtilis. *Microb. Biotechnol.* 4,98-105 (2011).
Beauregard, Pascale B et al. "Bacillus subtilis biofilm induction by plant polysaccharides." Proceedings of the National Academy of Sciences of the United States of America vol. 110,17 (2013): E1621-30.
Beyer, Dieter et al. "New class of bacterial phenylalanyl-tRNA synthetase inhibitors with high potency and broad-spectrum activity." Antimicrobial agents and chemotherapy vol. 48,2 (2004): 525-32.
Bongers, Roger S et al. "Development and characterization of a subtilin-regulated expression system in Bacillus subtilis: strict control of gene expression by addition of subtilin." Applied and environmental microbiology vol. 71, 12 (2005): 8818-24.
Borrero, Juan et al. "Modified lactic acid bacteria detect and inhibit multiresistant enterococci." ACS synthetic biology vol. 4,3 (2015): 299-306.
Bourdeau, Raymond W et al. "Acoustic reporter genes for noninvasive imaging of microorganisms in mammalian hosts." Nature vol. 553,7686 (2018): 86-90.
Brans, Alain et al. "New integrative method to generate Bacillus subtilis recombinant strains free of selection markers." Applied and environmental microbiology vol. 70, 12 (2004): 7241-50.
Brophy, Jennifer A N, and Christopher A Voigt. "Principles of genetic circuit design." Nature methods vol. 11,5 (2014): 508-20.
Bustin, Stephen, and Jim Huggett. "qPCR primer design revisited." Biomolecular detection and quantification vol. 14 19-28. Nov. 22, 2017.
Castillo-Hair, Sebastian M et al. "Optogenetic control of Bacillus subtilis gene expression." Nature communications vol. 10,1 3099. Jul. 15, 2019.

(56) References Cited

OTHER PUBLICATIONS

Chan, Clement T Y et al. "'Deadman' and 'Passcode' microbial kill switches for bacterial containment." Nature chemical biology vol. 12,2 (2016): 82-6.
Chiu, Charles Y, and Steven A Miller. "Clinical metagenomics." Nature reviews. Genetics vol. 20,6 (2019): 341-355.
Clark, Ryan L et al. "Design of synthetic human gut microbiome assembly and butyrate production." Nature communications vol. 12,1 3254. May 31, 2021.
Danino, Tal et al. "A synchronized quorum of genetic clocks." Nature vol. 463,7279 (2010): 326-30.
Dong, H., Zhang, D. "Current development in genetic engineering strategies of Bacillus species." Microb Cell Fact 13, 63 (2014).
Du, Pei et al. "De novo design of an intercellular signaling toolbox for multi-channel cell-cell communication and biological computation." Nature communications vol. 11,1 4226. Aug. 24, 2020.
Dubnau, D. "Genetic competence in Bacillus subtilis." Microbiological reviews vol. 55,3 (1991): 395-424.
East-Seletsky, Alexandra et al. "Two distinct RNase activities of CRISPR-C2c2 enable guide-RNA processing and RNA detection." Nature vol. 538,7624 (2016): 270-273.
Fàbrega, Anna, and Jordi Vila. "*Salmonella enterica* serovar Typhimurium skills to succeed in the host: virulence and regulation." Clinical microbiology reviews vol. 26,2 (2013): 308-41.
Fabret, Céline et al. "A new mutation delivery system for genome-scale approaches in Bacillus subtilis." Molecular microbiology vol. 46,1 (2002): 25-36.
Giordano, Nicole et al. "Cysteine Desulfurase IscS2 Plays a Role in Oxygen Resistance in Clostridium difficile." Infection and immunity vol. 86,8 e00326-18. Jul. 23, 2018.
Gomes, A.L.C., Johns, N.I., Yang, A. et al. "Genome and sequence determinants governing the expression of horizontally acquired DNA in bacteria." ISME J 14, 2347-2357 (2020).
González, Lina M et al. "Resilient living materials built by printing bacterial spores." Nature chemical biology vol. 16,2 (2020): 126-133.
Gootenberg, Jonathan S et al. "Nucleic acid detection with CRISPR-Cas13a/C2c2." Science (New York, N.Y.) vol. 356,6336 (2017): 438-442.
Gu, Wei et al. "Clinical Metagenomic Next-Generation Sequencing for Pathogen Detection." Annual review of pathology vol. 14 (2019): 319-338.
Guan, Chengran et al. "Development of an efficient autoinducible expression system by promoter engineering in Bacillus subtilis." Microbial cell factories vol. 15 66. Apr. 25, 2016.
Guiziou, Sarah et al. "A part toolbox to tune genetic expression in Bacillus subtilis." Nucleic acids research vol. 44,15 (2016): 7495-508.
Hemmi, H et al. "A Toll-like receptor recognizes bacterial DNA." Nature vol. 408,6813 (2000): 740-5.
Ibekwe, A M, and C M Grieve. "Detection and quantification of *Escherichia coli* O157:H7 in environmental samples by real-time PCR." Journal of applied microbiology vol. 94,3 (2003): 421-31.
Iqbal, S S et al. "A review of molecular recognition technologies for detection of biological threat agents." Biosensors & bioelectronics vol. 15,11-12 (2000): 549-78.
Itaya, M. "Effective Cloning of Unmarked DNA Fragments in the Bacillus subtilis 168 Genome." Bioscience, biotechnology, and biochemistry vol. 63,3 (1999): 602-604.
Itaya, Mitsuhiro, and Shinya Kaneko. "Integration of stable extracellular DNA released from *Escherichia coli* into the Bacillus subtilis genome vector by culture mix method." Nucleic acids research vol. 38,8 (2010): 2551-7.
Ji, Minghua et al. "Engineering Bacillus subtilis ATCC 6051a for the production of recombinant catalases." Journal of industrial microbiology & biotechnology vol. 48,5-6 (2021): kuab024.
Jung, Byeong Yeal et al. "Development of a rapid immunochromatographic strip for detection of *Escherichia coli* 0157." Journal of food protection vol. 68,10 (2005): 2140-3.
Kim, L et al. "A xylose-inducible Bacillus subtilis integration vector and its application." Gene vol. 181, 1-2 (1996): 71-6.
Kleina, L G, and J H Miller. "Genetic studies of the lac repressor. XIII. Extensive amino acid replacements generated by the use of natural and synthetic nonsense suppressors." Journal of molecular biology vol. 212,2 (1990): 295-318.
Konkol, Melissa A et al. "Plasmid-encoded ComI inhibits competence in the ancestral 3610 strain of Bacillus subtilis." Journal of bacteriology vol. 195,18 (2013): 4085-93.
Krieg, Arthur M. "CpG motifs in bacterial DNA and their immune effects." Annual review of immunology vol. 20 (2002): 709-60.
Kurushima, Jun et al. "Unbiased homeologous recombination during pneumococcal transformation allows for multiple chromosomal integration events." eLife vol. 9 e58771. Sep. 23, 2020.
Law, Jodi Woan-Fei et al. "Rapid methods for the detection of foodborne bacterial pathogens: principles, applications, advantages and limitations." Frontiers in microbiology vol. 5 770. Jan. 12, 2015.
Liao, Michael J et al. "Rock-paper-scissors: Engineered population dynamics increase genetic stability." Science (New York, N.Y.) vol. 365,6457 (2019): 1045-1049.
Lobo, Susana A L et al. "*Staphylococcus aureus* haem biosynthesis: characterisation of the enzymes involved in final steps of the pathway." Molecular microbiology vol. 97,3 (2015): 472-87.
Marchand, Nicholas, and Cynthia H Collins. "Peptide-based communication system enables *Escherichia coli* to Bacillus megaterium interspecies signaling." Biotechnology and bioengineering vol. 110,11 (2013): 3003-12.
Marchand, Nicholas, and Cynthia H Collins. "Synthetic Quorum Sensing and Cell-Cell Communication in Gram-Positive Bacillus megaterium." ACS synthetic biology vol. 5,7 (2016): 597-606.
Mascher, Thorsten et al. "Antibiotic-inducible promoter regulated by the cell envelope stress-sensing two-component system LiaRS of Bacillus subtilis." Antimicrobial agents and chemotherapy vol. 48,8 (2004): 2888-96.
McBride, Mary T et al. "Autonomous detection of aerosolized Bacillus anthracis and Yersinia pestis." Analytical chemistry vol. 75,20 (2003): 5293-9.
McClelland, M et al. "Complete genome sequence of *Salmonella enterica* serovar Typhimurium LT2." Nature vol. 413,6858 (2001): 852-6.
Miller, M B, and B L Bassler. "Quorum sensing in bacteria." Annual review of microbiology vol. 55 (2001): 165-99.
Morens, David M, and Anthony S Fauci. "Emerging Pandemic Diseases: How We Got to COVID-19." Cell vol. 182,5 (2020): 1077-1092.
Nißler, Robert et al. "Remote near infrared identification of pathogens with multiplexed nanosensors." Nature communications vol. 11,1 5995. Nov. 25, 2020.
Ortiz, Monica E, and Drew Endy. "Engineered cell-cell communication via DNA messaging." Journal of biological engineering vol. 6,1 16. Sep. 7, 2012.
Papagiannopoulou, Christina et al. "Fast Pathogen Identification Using Single-Cell Matrix-Assisted Laser Desorption/Ionization-Aerosol Time-of-Flight Mass Spectrometry Data and Deep Learning Methods." Analytical chemistry vol. 92,11 (2020): 7523-7531.
Peters, Jason M et al. "Enabling genetic analysis of diverse bacteria with Mobile-CRISPRi." Nature microbiology vol. 4,2 (2019): 244-250.
Popp, Philipp F et al. "The Bacillus BioBrick Box 2.0: expanding the genetic toolbox for the standardized work with Bacillus subtilis." Scientific reports vol. 7,1 15058. Nov. 8, 2017.
Prindle, Arthur et al. "Ion channels enable electrical communication in bacterial communities." Nature vol. 527,7576 (2015): 59-63.
Ragheb, Mark N et al. "Mfd regulates RNA polymerase association with hard-to-transcribe regions in vivo, especially those with structured RNAs." Proceedings of the National Academy of Sciences of the United States of America vol. 118,1 (2021): e2008498118.
Renda, Brian A et al. "Engineering reduced evolutionary potential for synthetic biology." Molecular bioSystems vol. 10,7 (2014): 1668-78.

(56) References Cited

OTHER PUBLICATIONS

Rupnik, Maja et al. "Clostridium difficile infection: new developments in epidemiology and pathogenesis." Nature reviews. Microbiology vol. 7,7 (2009):526-36.
Saeidi, Nazanin et al. "Engineering microbes to sense and eradicate Pseudomonas aeruginosa, a human pathogen." Molecular systems biology vol. 7 521. Aug. 16, 2011.
Schindelin, Johannes et al. "Fiji: an open-source platform for biological-image analysis." Nature methods vol. 9,7 676-82. Jun. 28, 2012.
Scott, Spencer R, and Jeff Hasty. "Quorum Sensing Communication Modules for Microbial Consortia." ACS synthetic biology vol. 5,9 (2016): 969-77.
Serrano, Ester et al. "Recombination proteins differently control the acquisition of homeologous DNA during Bacillus subtilis natural chromosomal transformation." Environmental microbiology vol. 23,1 (2021): 512-524.
Sexton, John T, and Jeffrey J Tabor. "Multiplexing cell-cell communication." Molecular systems biology vol. 16,7 (2020): e9618.
Silvaggi, Jessica M et al. "Small untranslated RNA antitoxin in Bacillus subtilis." Journal of bacteriology vol. 187,19 (2005): 6641-50.
Soni, Isha et al. "Draft Genome Sequence of Methicillin-Sensitive *Staphylococcus aureus* ATCC 29213." Genome announcements vol. 3,5 e01095-15. Sep. 24, 2015.
Stabler, Richard A et al. "Comparative genome and phenotypic analysis of Clostridium difficile 027 strains provides insight into the evolution of a hypervirulent bacterium." Genome biology vol. 10,9 (2009): R102.
Tack, Drew S et al. "The genotype-phenotype landscape of an allosteric protein." Molecular systems biology vol. 17,3 (2021): e10179.
Tong, Steven Y C et al. "*Staphylococcus aureus* infections: epidemiology, pathophysiology, clinical manifestations, and management." Clinical microbiology reviews vol. 28,3 (2015): 603-61.
Tucker, S C, and J E Galán. "Complex function for SicA, a *Salmonella enterica* serovar typhimurium type III secretion-associated chaperone." Journal of bacteriology vol. 182,8 (2000): 2262-8.
Wang, Yang et al. "Bacillus subtilis genome editing using ssDNA with short homology regions." Nucleic acids research vol. 40,12 (2012): e91.
Xi, H et al. "Purine catabolismin *Escherichia coli* and function of xanthine dehydrogenase in purine salvage." Journal of bacteriology vol. 182,19 (2000): 5332-41.
You, Lingchong et al. "Programmed population control by cell-cell communication and regulated killing." Nature vol. 428,6985 (2004): 868-71.
Zhang, Xiao-Zhou et al. "mazF, a novel counter-selectable marker for unmarked chromosomal manipulation in Bacillus subtilis." Nucleic acids research vol. 34,9 e71. May 19, 2006.
Zhang, Xiao-Zhou, and Y-H Percival Zhang. "Simple, fast and high-efficiency transformation system for directed evolution of cellulase in Bacillus subtilis." Microbial biotechnology vol. 4,1 (2011): 98-105.
Zhou, Chaoyang et al. "pheS * , an effective host-genotype-independent counter-selectable marker for marker-free chromosome deletion in Bacillus amyloliquefaciens." Applied microbiology and biotechnology vol. 101,1 (2017): 217-227.
Zou, Yiping et al. "Nucleic acid purification from plants, animals and microbes in under 30 seconds." PLoS biology vol. 15,11 e2003916. Nov. 21, 2017.

* cited by examiner

Fluorescent colonies
Recombination: 12

+gDNA

Fluorescent colonies
*txpA* deletion: 6
Non-fluorescent colonies
*lacI* mutation: 6

-gDNA

| Toxin x | 2nd repressor y | Promoter $P_y$ |
|---|---|---|
| *txpA* | *xylR* | $P_{xylA}$ |
| *mazF* | *cI* | $P_R$ |
| *hewl* | CRISPRi | $P_{const}$ |

SEQUENCE LISTING

```
Sequence total quantity: 24
SEQ ID NO: 1            moltype = DNA  length = 107
FEATURE                 Location/Qualifiers
source                  1..107
                        mol_type = other DNA
                        organism = synthetic construct
SEQUENCE: 1
tgtaaataca gttctggatt gcgagaaaac gaagtaaaag gatatccggc ctgaattcag  60
gccggattca ctggtagcga ccggcgctca ggatcctaac tcacatt                107

SEQ ID NO: 2            moltype = DNA  length = 107
FEATURE                 Location/Qualifiers
source                  1..107
                        mol_type = other DNA
                        organism = synthetic construct
SEQUENCE: 2
tgcctcaagc tagagagtcg aattcctgca gccctggcag gttatgtgtt taacaactca  60
tatttcttaa tcttgcgata gagcgtagca atgccgatgc ccagttc                107

SEQ ID NO: 3            moltype = DNA  length = 107
FEATURE                 Location/Qualifiers
source                  1..107
                        mol_type = other DNA
                        organism = synthetic construct
SEQUENCE: 3
aactaccctt taataggagg gtcctcgtgt agacactttt cctttacagt aatgtaaata  60
ggatgagtgt ctttttttct aagcatgaat aataatgtta aaagaga                107

SEQ ID NO: 4            moltype = DNA  length = 108
FEATURE                 Location/Qualifiers
source                  1..108
                        mol_type = other DNA
                        organism = synthetic construct
SEQUENCE: 4
ctgaatttga ttgcgagtga gatatttatg ccagccagcc agacgcagac gcgccgagac  60
agaacttaat gggcccgcta acagcgcgat ttgctggtga cccaatgc               108

SEQ ID NO: 5            moltype = DNA  length = 809
FEATURE                 Location/Qualifiers
source                  1..809
                        mol_type = other DNA
                        organism = synthetic construct
SEQUENCE: 5
ctcgagggta aatgtgagca ctcacaattc attttgcaaa agttgttgac tttatctaca  60
aggtgtggca taatgtgtgt aattgtgagc ggataacaat taagcttaca taaggaggaa  120
ctactatgtc gacctatgaa tctctaatgg tcatgatcgg ctttgccaat ttaataggcg  180
ggattatgac atgggtaata tctcttttaa cattattatt catgcttaga aaaaaagaca  240
ctcatcctat ttacattact gtaaaggaaa agtgtctaca cgaggaccct cctattaaag  300
ggtagtttct tttttaaaag ctagagtgct gccacactct ggcttttata ttttagcatt  360
tctcatgaaa gtaacacaca ttaacaagtg gtaatgtggt aatgtggtac caactataag  420
cttacgccag tagttgcaat acttttgctt ggcaccatta taacatgaat atatattgat  480
tatataatta tttgtatctt ttatttgtta cttttttttat ctatgagttc aaaatgacct  540
gatcatagaa gccttaaccc tttttctttt attaaaaacc ctcggattat gaaagtgtta  600
tggtacaata tggtttagta taaatgaata ttggctttca acatctcaag ggcggtctgg  660
ctcactccct catgaaaggg ggtgatgcac gtgtcaacat ttcaagcatt aatgcttatg  720
cttgctttcg ggtcatttat aattgccctg ttgacttata taaagaagaa atagacccac  780
cccttgagct cggcaaagta aaagggtaa                                    809

SEQ ID NO: 6            moltype = DNA  length = 720
FEATURE                 Location/Qualifiers
```

```
source                  1..720
                        mol_type = other DNA
                        organism = synthetic construct
SEQUENCE: 6
atggtttcta aaggtgaaga attgtttaca ggtgttgttc caattttggt tgaattggat  60
ggtgatgtta atggtcataa attttctgtt tctggtgaag gtgaaggtga tgctacatac  120
ggtaaattga cattgaaatt tatttgtaca actggtaaat tgccagttcc ttggccaaca  180
ttggttacaa catttgctta tggtttgcaa tgttttgctc gttatccaga tcacatgaaa  240
caacatgatt tctttaaatc tgctatgcca gaaggttatg ttcaagaacg tacaatcttt  300
ttcaaggatg atggtaatta taagacacgt gctgaggtta agtttgaagg tgatacattg  360
gttaatcgta tcgaattgaa gggtatcgat tttaaagaag atggtaatat cttgggtcat  420
aaattggaat ataattataa ttctcataat gtttatatca tggctgataa acaaaagaac  480
ggtattaaag ttaattttaa aattcgtcat aatattgaag atggttctgt tcaattggct  540
gatcattatc aacaaaatac accaattggt gatggtccag ttttgttgcc agataatcat  600
tatttgtcta cacaatctaa attgtctaaa gatccaaatg aaaaacgtga tcacatggtt  660
ttgttggaat ttgttacagc tgctggtatt acacatggta tggatgaatt gtataaataa  720

SEQ ID NO: 7            moltype = DNA  length = 714
FEATURE                 Location/Qualifiers
source                  1..714
                        mol_type = other DNA
                        organism = synthetic construct
SEQUENCE: 7
atggttagca aaggcgaaga ggataaatatg gcgatcatca aagaatttat gcgctttaaa  60
gttcatatgg aaggcagcgt taatggccac gaatttgaaa ttgaaggcga aggtgaaggc  120
agaccgtatg aaggcacaca aacagcaaaa ctgaaagtta caaaaggcgg accgctgccg  180
tttgcatggg atattctgtc accgcaattt atgtatggca gcaaagcata tgttaaacat  240
ccggcagata tcccggatta tctgaaactg tcatttccgg aaggctttaa atgggaacgc  300
gtcatgaatt ttgaagatgg cggagttgtt acagtcacac aagattcatc actgcaagat  360
ggcgaattta tctataaagt caaactgcgt ggcacgaact ttccgtcaga tggccctgtt  420
atgcagaaaa aaacaatggg ctgggaagca tcaagcgaaa gaatgtatcc ggaagatggt  480
gcactgaaag gcgaaattaa acaacgcctg aaacttaaag acggtggaca ttatgatgcg  540
gaagtcaaaa caacgtataa agcgaaaaaa cctgttcaac tgcctggcgc atataacgtt  600
aacattaaac tggatatcac gagccataac gaagattata caatcgtcga acagtatgaa  660
agagcagaag gacgccattc aacaggcgga atggatgaac tgtataaata ctag        714

SEQ ID NO: 8            moltype = DNA  length = 705
FEATURE                 Location/Qualifiers
source                  1..705
                        mol_type = other DNA
                        organism = synthetic construct
SEQUENCE: 8
atgagcgaac tgatcaaaga aaacatgcat atgaaactgt acatggaagg cacagtcgat  60
aaccatcact ttaaatgcac atcagaaggc gaaggcaaac cgtatgaagg cacacaaaca  120
atgagaatca aagttgttga aggcggaccg ctgccgtttg catttgatat tctggcaaca  180
tcatttctgt atggcagcaa aacgtttatc aatcatacac aaggcatccc ggattttttt  240
aaacaatcat ttccggaagg ctttacatgg gaacgcgtta caacatatga agatggcgga  300
gttctgacag caacacaaga tacatcattg caagatggct gcctgatcta taatgtcaaa  360
attagaggcg tcaactttac aagcaatggc cctgttatgc agaaaaaaac actgggctgg  420
gaagcattta cagaaacact gtatccggct gatggcggac tggaaggcag aaacgatatg  480
gcactgaaac tggttggcgg atcacatctg attgcaaaca tcaaaacaac gtaccgctca  540
aaaaaaccgg caaaaaatct gaaaatgcct ggcgtctatt atgtcgatta tagactggaa  600
cgcatcaaag aagcgaacaa cgaaacatat gtcgaacaac atgaagttgc agttgcgaga  660
tattgcgatc tgccgtcaaa actgggccat aaactgaatt actag                  705

SEQ ID NO: 9            moltype = DNA  length = 464
FEATURE                 Location/Qualifiers
source                  1..464
                        mol_type = other DNA
                        organism = synthetic construct
SEQUENCE: 9
caattaccat cgaatgcacc attaacggga tgccttttca gcttcacgcc gcaccaggca  60
cgccgctctc ggaattactc cgcgaacaag gactgctaag tgtcaaacaa gggtgctgcg  120
tgggtgaatg tggtgcctgt acggtgttgg tcgacggcac agcaatagac agttgcttat  180
accttgccgc ctgggctgaa ggaaaagaga tccgcacgct ggaaggtgaa gcgaaaggcg  240
gaaaactttc tcatgttcag caggcttatg cgaaatccgg cgcagtgcag tgcgggtttt  300
gtacgcctgg cctgattatg gctaccacgg caatgctggc gaaaccacgc gagaagccat  360
taaccattac ggaaattcgt cgcggactgg cgggaaatct ttgtcgctgc acggggtatc  420
agatgattgt aaatacagtt ctggattgcg agaaaacgaa gtaa                  464

SEQ ID NO: 10           moltype = DNA  length = 497
FEATURE                 Location/Qualifiers
source                  1..497
                        mol_type = other DNA
                        organism = synthetic construct
SEQUENCE: 10
ttatgtgttt aacaactcat atttcttaat cttgcgatag agcgtagcaa tgccgatgcc  60
cagttcatca gcaacttgct tcttgctgtt atgacgtgaa agcgcctcgc ggatcatttg  120
cttttccatc tcctccagcg ccgtgccgcc cgcatcatcg agtgacaggt gcgcctcact  180
```

```
gacctctgtt acatcacttt gctccgttgt gccattattc agcagatttg gcggcaatag  240
cgtgctgtcg ataacttcac ctgaaggaac cacgttaacc agatattcca tcaaattgct  300
taactcgcgc aggtttccgg gccaacgatg cttacgcaat atttcgacga catcgggagc  360
aatgccagga taaaccgatc ccagacgacg ggtatgcaga tgtaaaaagt aatgcaccaa  420
tagttcaata tcttcctgac gttcacgcag cggtggcaga gttatcggga taacattaag  480
tcggtagaag agatctt                                                 497

SEQ ID NO: 11          moltype = DNA  length = 1000
FEATURE                Location/Qualifiers
source                 1..1000
                       mol_type = other DNA
                       organism = synthetic construct
SEQUENCE: 11
atgacgcgaa actggagatc cactccccgc gcggtgttcg tttcgtcccg attaatggct  60
ttcacaccgg gccgggcaaa gtgtctcttg agcatgacga aatcctcgtc gcctttcatt  120
ttccgccaca gccgaaagaa cacgcgggca gcgcgcattt taaatatgcc atgcgcgacg  180
caatggatat ttcaacgatt ggctgcgccg cacattgccg actggataac ggcaatttca  240
gcgaattacg cctggcattt ggtgttgccg cgccaacgcc gattcgctgc caacatgccg  300
aacagactgc acaaaatgcg ccattaaacc tgcaaacgct ggaagctatc agcgaatctg  360
tcctgcaaga tgtcgccccg cgttcttcat ggcgggccag taaagagttt cgtctgcatc  420
tcatccagac gatgaccaaa aaagtgatta gcgaagccgt cgccgcggcg gggggaaaat  480
tgcaatgaat cacagcgaaa caattaccat cgaatgcacc attaacggga tgccttttca  540
gcttcacgcc gcaccaggca cgccgctctc ggaattactc cgcgaacaag gactgctaag  600
tgtcaaacaa gggtgctgcg tgggtgaatg tggtgcctgt acggtgttgg tcgacggcac  660
agcaatagac agttgcttat accttgccgc ctgggctgaa ggaaaagaga tccgcacgct  720
ggaaggtgaa gcgaaaggcg gaaaactttc tcatgttcag caggcttatg cgaaatccgg  780
cgcagtgcag tgcgggtttt gtacgcctgg cctgattatg gctaccacgg caatgctggc  840
gaaaccacgc gagaagccat taaccattac ggaaattcgt cgcggactgg cgggaaatct  900
ttgtcgctgc acggggtatc agatgattgt aaatacagtt ctggattgcg agaaaacgaa  960
gtaaaaggat atccggcctg aattcaggcc ggattcactg                        1000

SEQ ID NO: 12          moltype = DNA  length = 1000
FEATURE                Location/Qualifiers
source                 1..1000
                       mol_type = other DNA
                       organism = synthetic construct
SEQUENCE: 12
aggttatgtg tttaacaact catatttctt aatcttgcga tagagcgtag caatgccgat  60
gcccagttca tcagcaactt gcttcttgct gttatgacgt gaaagcgcct cgcggatcat  120
ttgcttttcc atctcctcca gcgccgtgcc gcccgcatca tcgagtgaca ggtgcgcctc  180
actgacctct gttacatcac tttgctccgt tgtgccatta ttcagcagat ttggcggcaa  240
tagcgtgctg tcgataactt cacctgaagg aaccacgtta accagatatt ccatcaaatt  300
gcttaactcg cgcaggtttc cgggccaacg atgcttacgc aatatttcga cgacatcggg  360
agcaatgcca ggataaaccg atcccagacg acgggtatgc agatgtaaaa agtaatgcac  420
caatagttca atatcttcct gacgttcacg cagcggtggc agagttatcg ggataacatt  480
aagtcggtag aagagatctt cgcggaattt accttcggca atgaactggg ccaaattctg  540
attagttgca gaaatgatgc gaatgtcgac ttgtattggg ctactggcac caatcggcag  600
aatttcacgt gcctcaatag cgcgcagtaa tttagcctgc aacattaatg gcatatcacc  660
tatttcatcg agaaacagcg tgcccgtatt cgccgcctga atcaaccctg ttttaccgtt  720
ggcagaagcg ccagtaaatg cacctttaac ataaccgaac agttcgctct ccagaagctg  780
ctccggaatc gcggcacagt tgatagcaat aaagggttta ttccgtcttc cgctcaactt  840
atggattgca cgggcgacga cttctttacc cgtgccgctt tcaccaacca ccataacgct  900
ggatgggctg ggtgcaatac ggctaatgag tcgttttaat tgccgcataa cacggcactc  960
gccaaccaat tgttcaatat gcggttcatc aggtgcattt                        1000

SEQ ID NO: 13          moltype = DNA  length = 1500
FEATURE                Location/Qualifiers
source                 1..1500
                       mol_type = other DNA
                       organism = synthetic construct
SEQUENCE: 13
cgtaacgcgg tgaagatggc taccggtgtt gcaatcaata cactgccgct gacgccaaaa  60
cggttatatg aagagttcca tctggcagga ttgatttgag gataacatca tgtttgattt  120
tgcttcttac catcgcgcag caacccttgc cgatgccatc aacctgctgg ctgacaaccc  180
gcaggccaaa ctgctcgccg gtggcactga cgtactgatt cagctccacc atcacaatga  240
ccgttatcgc catattgttg atattcataa tctggcggag ctgcggggaa ttacgctggc  300
ggaagatggc tcgctacgta tcggctctgc aacgacattt acccagctaa tagaagatcc  360
tataactcaa cgtcatctcc cggcgttatg tgctgcggcc acgtccattg ctggaccgca  420
gatccgtaac gtcgctacct acggtggaaa tatttgcaac ggtgccacca gcgcagattc  480
tgccacgcca acgctaattt atgacgcgaa actggagatc cactccccgc gcggtgttcg  540
tttcgtcccg attaatggct ttcacaccgg gccgggcaaa gtgtctcttg agcatgacga  600
aatcctcgtc gcctttcatt ttccgccaca gccgaaagaa cacgcgggca gcgcgcattt  660
taaatatgcc atgcgcgacg caatggatat ttcaacgatt ggctgcgccg cacattgccg  720
actggataac ggcaatttca gcgaattacg cctggcattt ggtgttgccg cgccaacgcc  780
gattcgctgc caacatgccg aacagactgc acaaaatgcg ccattaaacc tgcaaacgct  840
ggaagctatc agcgaatctg tcctgcaaga tgtcgccccg cgttcttcat ggcgggccag  900
taaagagttt cgtctgcatc tcatccagac gatgaccaaa aaagtgatta gcgaagccgt  960
cgccgcggcg gggggaaaat tgcaatgaat cacagcgaaa caattaccat cgaatgcacc  1020
attaacggga tgccttttca gcttcacgcc gcaccaggca cgccgctctc ggaattactc  1080
```

```
cgcgaacaag gactgctaag tgtcaaacaa gggtgctgcg tgggtgaatg tggtgcctgt  1140
acggtgttgg tcgacggcac agcaatagac agttgcttat accttgccgc ctgggctgaa  1200
ggaaaagaga tccgcacgct ggaaggtgaa gcgaaaggcg gaaaactttc tcatgttcag  1260
caggcttatg cgaaatccgg cgcagtgcag tgcgggtttt gtacgcctgg cctgattatg  1320
gctaccacgg caatgctggc gaaaccacgc gagaagccat taaccattac ggaaattcgt  1380
cgcggactgg cgggaaatct ttgtcgctgc acggggtatc agatgattgt aaatacagtt  1440
ctggattgcg agaaaacgaa gtaaaaggat atccggcctg aattcaggcc ggattcactg  1500

SEQ ID NO: 14           moltype = DNA  length = 1500
FEATURE                 Location/Qualifiers
source                  1..1500
                        mol_type = other DNA
                        organism = synthetic construct
SEQUENCE: 14
aggttatgtg tttaacaact catatttctt aatcttgcga tagagcgtag caatgccgat  60
gcccagttca tcagcaactt gcttcttgct gttatgacgt gaaagcgcct cgcggatcat  120
ttgcttttcc atctcctcca gcgccgtgcc gcccgcatca tcgagtgaca ggtgcgcctc  180
actgacctct gttacatcac tttgctccgt tgtgccatta ttcagcagat ttggcggcaa  240
tagcgtgctg tcgataactt cacctgaagg aaccacgtta accagatatt ccatcaaatt  300
gcttaactcg cgcaggtttc cgggccaacg atgcttacgc aatatttcga cgacatcggg  360
agcaatgcca ggataaaccg atcccagacg acgggtatgc agatgtaaaa agtaatgcac  420
caatagttca atatcttcct gacgttcacg cagcggtggc agagttatcg ggataacatt  480
aagtcggtag aagagatctt cgcggaattt accttcggca atgaactggg ccaaattctg  540
attagttgca gaaatgatgc gaatgtcgac ttgtattggg ctactggcac caatcggcag  600
aatttcacgt gcctcaatag cgcgcagtaa tttagcctgc aacattaatg gcatatcacc  660
tatttcatcg agaaacagcg tgcccgtatt cgccgcctga atcaaccctg ttttaccgtt  720
ggcagaagcg ccagtaaatg cacctttaac ataaccgaac agttcgctct ccagaagctg  780
ctccggaatc gcggcacagt tgatagcaat aaagggttta ttccgtcttc cgctcaactt  840
atggattgca cgggcgacga cttctttacc cgtgccgctt tcaccaacca ccataacgct  900
ggatgggctg ggtgcaatac ggctaatgag tcgttttaat tgccgcataa cacggcactc  960
gccaaccaat tgttcaatat gcggttcatc aggtgcattt gctacagaaa aactggtatg  1020
cgattggtga aacgccatta aaaataattg tcggccctga atgttatgca attgaccaat  1080
gattaattca cttttatcgt cccatgaaac aatatgctgc atatgtccat gggtaaaatt  1140
actctcaaat gttaatggtc tgaaacggat aggtttccca ataatattat tttgcacaac  1200
accaagtgtt tttaaggcag tctgattaac aaactgaacc cgattttcat catctacaac  1260
taatacgccc tgatccatat tatcgatcat ggtcgcaaat attttactga tgttatctcc  1320
tggcccctga tcctccagaa gtttcgaaac aaaaatggtg gatatatggc gaacataatc  1380
agaaaattcg cgtaaattat cactgatatg ctcttgttgc tcgtgggtaa cggcaatcaa  1440
acttatcacc ccaacacaac gatcctgtaa aatgacaggc gtacccagaa atgctttttc  1500

SEQ ID NO: 15           moltype = DNA  length = 2000
FEATURE                 Location/Qualifiers
source                  1..2000
                        mol_type = other DNA
                        organism = synthetic construct
SEQUENCE: 15
ccctgataaa aggccatatc gtgctggttg aacgaccgga agagccgtta atgtcgttaa  60
aagatttggc gatggacgct ttctaccacc ctgaacgcgg cgggcagctc tctgctgaaa  120
gctccatcaa aaccaccact aacccaccgg cgtttggctg tacctttgtt gatctgacgg  180
tcgatattgc gctgtgcaaa gtcaccatca accgcatcct caacgttcat gattcagggc  240
atattcttaa tccactgctg gcagaaggtc aggtacacgg cggaatggga atgggcattg  300
gctgggcgct atttgaagag atgatcatcg atgctaaaag cggcgtggtc cgtaacccca  360
atctgctgga ttacaaaatg ccgaccatgc cggatctgcc acaactggaa agcgcgttcg  420
tcgaaatcaa tgagccgcaa tccgcatacg gacataagtc actgggtgag ccaccaataa  480
ttcctgttgc cgctgctatt cgtaacgcgg tgaagatggc taccggtgtt gcaatcaata  540
cactgccgct gacgccaaaa cggttatatg aagagttcca tctggcagga ttgatttgag  600
gataacatca tgtttgattt tgcttcttac catcgcgcag caacccttgc cgatgccatc  660
aacctgctgg ctgacaaccc gcaggccaaa ctgctcgccg gtggcactga cgtactgatt  720
cagctccacc atcacaatga ccgttatcgc catattgttg atattcataa tctggcggag  780
ctgcggggaa ttacgctggc ggaagatggc tcgctacgta tcggctctgc aacgacattt  840
acccagctaa tagaagatcc tataactcaa cgtcatctcc cggcgttatg tgctgcggcc  900
acgtccattg ctggaccgca gatccgtaac gtcgctacct acggtggaaa tatttgcaac  960
ggtgccacca gcgcagattc tgccacgcca acgctaattt atgacgcgaa actggagatc  1020
cactccccgc gcggtgttcg tttcgtcccg attaatggct ttcacaccgg gccgggcaaa  1080
gtgtctcttg agcatgacga aatcctcgtc gcctttcatt ttccgccaca gccgaaagaa  1140
cacgcgggca gcgcgcattt taaatatgcc atgcgcgacg caatggatat ttcaacgatt  1200
ggctgcgccg cacattgccg actggataac ggcaatttca gcgaattacg cctggcattt  1260
ggtgttgccg cgccaacgcc gattcgctgc caacatgccg aacagactgc acaaaatgcg  1320
ccattaaacc tgcaaacgct ggaagctatc agcgaatctg tcctgcaaga tgtcgccccg  1380
cgttcttcat ggcgggccag taaagagttt cgtctgcatc tcatccagac gatgaccaaa  1440
aaagtgatta gcgaagccgt cgccgcggcg gggggaaaat tgcaatgaat cacagcgaaa  1500
caattaccat cgaatgcacc attaacggga tgccttttca gcttcacgcc gcaccaggca  1560
cgccgctctc ggaattactc cgcgaacaag gactgctaag tgtcaaacaa gggtgctgcg  1620
tgggtgaatg tggtgcctgt acggtgttgg tcgacggcac agcaatagac agttgcttat  1680
accttgccgc ctgggctgaa ggaaaagaga tccgcacgct ggaaggtgaa gcgaaaggcg  1740
gaaaactttc tcatgttcag caggcttatg cgaaatccgg cgcagtgcag tgcgggtttt  1800
gtacgcctgg cctgattatg gctaccacgg caatgctggc gaaaccacgc gagaagccat  1860
taaccattac ggaaattcgt cgcggactgg cgggaaatct ttgtcgctgc acggggtatc  1920
agatgattgt aaatacagtt ctggattgcg agaaaacgaa gtaaaaggat atccggcctg  1980
```

-continued

```
aattcaggcc ggattcactg                                              2000

SEQ ID NO: 16          moltype = DNA  length = 2000
FEATURE                Location/Qualifiers
source                 1..2000
                       mol_type = other DNA
                       organism = synthetic construct
SEQUENCE: 16
aggttatgtg tttaacaact catatttctt aatcttgcga tagagcgtag caatgccgat  60
gcccagttca tcagcaactt gcttcttgct gttatgacgt gaaagcgcct cgcggatcat  120
ttgcttttcc atctcctcca gcgccgtgcc gcccgcatca tcgagtgaca ggtgcgcctc  180
actgacctct gttacatcac tttgctccgt tgtgccatta ttcagcagat ttggcggcaa  240
tagcgtgctg tcgataactt cacctgaagg aaccacgtta accagatatt ccatcaaatt  300
gcttaactcg cgcaggtttc cggccaacg atgcttacgc aatatttcga cgacatcggg  360
agcaatgcca ggataaaccg atcccagacg acgggtatgc agatgtaaaa agtaatgcac  420
caatagttca atatcttcct gacgttcacg cagcggtggc agagttatcg ggataacatt  480
aagtcggtag aagagatctt cgcggaattt accttcggca atgaactggg ccaaattctg  540
attagttgca gaaatgatgc gaatgtcgac ttgtattggg ctactggcac caatcggcag  600
aatttcacgt gcctcaatag cgcgcagtaa tttagcctgc aacattaatg gcatatcacc  660
tatttcatcg agaaacagcg tgcccgtatt cgccgcctga atcaaccctg ttttaccgtt  720
ggcagaagcg ccagtaaatg cacctttaac ataaccgaac agttcgctct ccagaagctg  780
ctccggaatc gcggcacagt tgatagcaat aaagggttta ttccgtcttc cgctcaactt  840
atggattgca cgggcgacga cttctttacc cgtgccgctt tcaccaacca ccataacgct  900
ggatgggctg ggtgcaatac ggctaatgag tcgttttaat tgccgcataa cacggcactc  960
gccaaccaat tgttcaatat gcggttcatc aggtgcattt gctacagaaa aactggtatg  1020
cgattggtga aacgccatta aaaataattg tcggccctga atgttatgca attgaccaat  1080
gattaattca cttttatcgt cccatgaaac aatatgctgc atatgtccat gggtaaaatt  1140
actctcaaat gttaatggtc tgaaacggat aggtttccca ataatattat tttgcacaac  1200
accaagtgtt tttaaggcag tctgattaac aaactgaacc cgattttcat catctacaac  1260
taatacgccc tgatccatat tatcgatcat ggtcgcaaat attttactga tgttatctcc  1320
tggcccctga tcctccagaa gtttcgaaac aaaaatggtg gatatatggc gaacataatc  1380
agaaaattcg cgtaaattat cactgatatg ctcttgttgc tcgtgggtaa cggcaatcaa  1440
acttatcacc ccaacacaac gatcctgtaa aatgacaggc gtacccagaa atgctttttc  1500
gcggcaattt tctttactat cgcaaccttc gcaaagggga tcgaagcgag actgtgtcac  1560
aactttttca gttttcgttt ccaggacgtg gcggagcagg cgtgagttgc cgctcaactg  1620
gcgaccaaga aacttcccat acgcgcccgt tccggcaacg cgacacaagt tttcatcaac  1680
gatctcaacc tcaagctgca aaacgctggc aagcattctg gcaaaacgct gaattgtcgg  1740
ttgaatttgc atcaatactg actgcgtagt agcaagctcc atagctttac cttccagact  1800
tacttaaaag tcgatcattg aagacgttga tggttcacag atcatgatga tattaactca  1860
ggcgaaattg gctttgataa aaacataaga tttttatcat tttctaatga aattatggaa  1920
gagatatcac atttctatat caatatgaga attacggcgg tgagtttatc aaactgaaga  1980
gagatagcct gcccctttat                                              2000

SEQ ID NO: 17          moltype = DNA  length = 2500
FEATURE                Location/Qualifiers
source                 1..2500
                       mol_type = other DNA
                       organism = synthetic construct
SEQUENCE: 17
aggagatgct aatccgctca cgggcaaacg tatttacagc gcagggttgc cggagtgtct  60
tgaaaaaggc cggaaaatct ttgaatggga aaaacgccgt gcagaatgcc agaaccagca  120
aggcaatttg cgccgcggcg ttggcgtcgc ctgttttagc tacacctcta acacctggcc  180
tgtcggcgta gaaatagcag gcgcgcgcct tctgatgaat caggatggaa ccatcaacgt  240
gcaaagcggc gcgacggaaa tcggtcaggg tgccgacacc gtcttctcgc aaatggtggc  300
agaaaccgtg ggggttccgg tcagcgacgt tcgcgttatt tcaactcaag ataccgacgt  360
tacgccgttc gatcccggcg catttgcctc acgccagagc tatgttgccg cgcctgcgct  420
gcgcagtgcg gcactattat taaaagagaa aatcatcgct cacgccgcag tcatgctaca  480
tcagtcagcg atgaatctga ccctgataaa aggccatatc gtgctggttg aacgaccgga  540
agagccgtta atgtcgttaa aagatttggc gatggacgct ttctaccacc ctgaacgcgg  600
cgggcagctc tctgctgaaa gctccatcaa aaccaccact aacccaccgg cgtttggctg  660
tacctttgtt gatctgacgg tcgatattgc gctgtgcaaa gtcaccatca accgcatcct  720
caacgttcat gattcagggc atattcttaa tccactgctg gcagaaggtc aggtacacgg  780
cggaatggga atgggcattg gctgggcgct atttgaagag atgatcatcg atgctaaaag  840
cggcgtggtc cgtaacccca atctgctgga ttacaaaatg ccgaccatgc cggatctgcc  900
acaactggaa agcgcgttcg tcgaaatcaa tgagccgcaa tccgcatacg gacataagtc  960
actgggtgag ccaccaataa ttcctgttgc cgctgctatt cgtaacgcgg tgaagatggc  1020
taccggtgtt gcaatcaata cactgccgct gacgccaaaa cggttatatg aagagttcca  1080
tctggcagga ttgatttgag gataacatca tgtttgattt tgcttcttac catcgcgcag  1140
caacccttgc cgatgccatc aacctgctgg ctgacaaccc gcaggccaaa ctgctcgccg  1200
gtggcactga cgtactgatt cagctccacc atcacaatga ccgttatcgc catattgttg  1260
atattcataa tctggcggag ctgcggggaa ttacgctggc ggaagatggc tcgctacgta  1320
tcggctctgc aacgacattt acccagctaa tagaagatcc tataactcaa cgtcatctcc  1380
cggcgttatg tgctgcggcc acgtccattg ctggaccgca gatccgtaac gtcgctacct  1440
acggtggaaa tatttgcaac ggtgccacca gcgcagattc tgccacgcca acgctaattt  1500
atgacgcgaa actggagatc cactccccgc gcggtgttcg tttcgtcccg attaatggct  1560
ttcacaccgg gccgggcaaa gtgtctcttg agcatgacga aatcctcgtc gcctttcatt  1620
ttccgccaca gccgaaagaa cacgcgggca gcgcgcattt taaatatgcc atgcgcgacg  1680
caatggatat ttcaacgatt ggctgcgccg cacattgccg actggataac ggcaatttca  1740
gcgaattacg cctggcattt ggtgttgccg cgccaacgcc gattcgctgc caacatgccg  1800
```

```
aacagactgc acaaaatgcg ccattaaacc tgcaaacgct ggaagctatc agcgaatctg  1860
tcctgcaaga tgtcgccccg cgttcttcat ggcgggccag taaagagttt cgtctgcatc  1920
tcatccagac gatgaccaaa aaagtgatta gcgaagccgt cgccgcggcg gggggaaaat  1980
tgcaatgaat cacagcgaaa caattaccat cgaatgcacc attaacggga tgccttttca  2040
gcttcacgcc gcaccaggca cgccgctctc ggaattactc cgcgaacaag gactgctaag  2100
tgtcaaacaa gggtgctgcg tgggtgaatg tggtgcctgt acggtgttgg tcgacggcac  2160
agcaatagac agttgcttat accttgccgc ctgggctgaa ggaaaagaga tccgcacgct  2220
ggaaggtgaa gcgaaaggcg gaaaactttc tcatgttcag caggcttatg cgaaatccgg  2280
cgcagtgcag tgcgggtttt gtacgcctgg cctgattatg gctaccacgg caatgctggc  2340
gaaaccacgc gagaagccat taaccattac ggaaattcgt cgcggactgg cgggaaatct  2400
ttgtcgctgc acggggtatc agatgattgt aaatacagtt ctggattgcg agaaaacgaa  2460
gtaaaaggat atccggcctg aattcaggcc ggattcactg                        2500

SEQ ID NO: 18           moltype = DNA  length = 2500
FEATURE                 Location/Qualifiers
source                  1..2500
                        mol_type = other DNA
                        organism = synthetic construct
SEQUENCE: 18
aggttatgtg tttaacaact catatttctt aatcttgcga tagagcgtag caatgccgat  60
gcccagttca tcagcaactt gcttcttgct gttatgacgt gaaagcgcct cgcggatcat  120
ttgcttttcc atctcctcca gcgccgtgcc gcccgcatca tcgagtgaca ggtgcgcctc  180
actgacctct gttacatcac tttgctccgt tgtgccatta ttcagcagat ttggcggcaa  240
tagcgtgctg tcgataactt cacctgaagg aaccacgtta accagatatt ccatcaaatt  300
gcttaactcg cgcaggtttc cgggccaacg atgcttacgc aatatttcga cgacatcggg  360
agcaatgcca ggataaaccg atcccagacg acgggtatgc agatgtaaaa agtaatgcac  420
caatagttca atatcttcct gacgttcacg cagcggtggc agagttatcg ggataacatt  480
aagtcggtag aagagatctt cgcggaattt accttcggca atgaactggg ccaaattctg  540
attagttgca gaaatgatgc gaatgtcgac ttgtattggg ctactggcac caatcggcag  600
aatttcacgt gcctcaatag cgcgcagtaa tttagcctgc aacattaatg gcatatcacc  660
tatttcatcg agaaacagcg tgcccgtatt cgccgcctga atcaaccctg ttttaccgtt  720
ggcagaagcg ccagtaaatg cacctttaac ataaccgaac agttcgctct ccagaagctg  780
ctccggaatc gcggcacagt tgatagcaat aaagggttta ttccgtcttc cgctcaactt  840
atggattgca cgggcgacga cttctttacc cgtgccgctt tcaccaacca ccataacgct  900
ggatgggctg ggtgcaatac ggctaatgag tcgttttaat tgccgcataa cacggcactc  960
gccaaccaat tgttcaatat gcggttcatc aggtgcattt gctacagaaa aactggtatg  1020
cgattggtga aacgccatta aaaataattg tcggccctga atgttatgca attgaccaat  1080
gattaattca cttttatcgt cccatgaaac aatatgctgc atatgtccat gggtaaaatt  1140
actctcaaat gttaatggtc tgaaacggat aggtttccca ataatattat tttgcacaac  1200
accaagtgtt tttaaggcag tctgattaac aaactgaacc cgattttcat catctacaac  1260
taatacgccc tgatccatat tatcgatcat ggtcgcaaat attttactga tgttatctcc  1320
tggcccctga tcctccagaa gtttcgaaac aaaaatggtg gatatatggc gaacataatc  1380
agaaaattcg cgtaaattat cactgatatg ctcttgttgc tcgtgggtaa cggcaatcaa  1440
acttatcacc ccaacacaac gatcctgtaa aatgacaggc gtacccagaa atgctttttc  1500
gcggcaattt tctttactat cgcaaccttc gcaaagggga tcgaagcgag actgtgtcac  1560
aactttttca gttttcgttt ccaggacgtg gcggagcagg cgtgagttgc cgctcaactg  1620
gcgaccaaga aacttcccat acgcgcccgt tccggcaacg cgacacaagt tttcatcaac  1680
gatctcaacc tcaagctgca aaacgctggc aagcattctg gcaaaacgct gaattgtcgg  1740
ttgaatttgc atcaatactg actgcgtagt agcaagctcc atagctttac cttccagact  1800
tacttaaaag tcgatcattg aagacgttga tggttcacag atcatgatga tattaactca  1860
ggcgaaattg gctttgataa aaacataaga tttttatcat tttctaatga aattatggaa  1920
gagatatcac atttctatat caatatgaga attacggcgg tgagtttatc aaactgaaga  1980
gagatagcct gccccttat cttatttctg atacttagca gcaaataaat aacgcgataa  2040
aaaaagccaa acgttttcgt attttacaaa caaccagaag ctggcatcaa tttgtgatca  2100
accccacaca ttatccgtca aattagtctt ttgcagccgc gcggataatt ctggcacact  2160
tattgttagt cccaggtata gctgtgaaaa caccaatcac tttggcaagt cacagtgaaa  2220
taaaccactt tgcctgtcat tccactaccg ggactttatg atgaaaactg ttaatgagct  2280
gattaaggat atcaattcgc tgacctctca ccttcacgag aaagattttt tgttaacgtg  2340
ggaacagacg ccagatgaac tgaaacaagt actggacgtt gccgcagcat taaaagcact  2400
gcgtgctgaa aacatctcaa ccaaagtctt taatagtgga ttaggtattt ccgtattccg  2460
cgacaactcc acccgtaccc gcttctctta tgcttccgcg                        2500

SEQ ID NO: 19           moltype = DNA  length = 2500
FEATURE                 Location/Qualifiers
source                  1..2500
                        mol_type = other DNA
                        organism = synthetic construct
SEQUENCE: 19
acgtagcagc aggggtatca acgtttgcat ttcaaggtgc cgggcttccc gtcctacgct  60
ggtaccctgc tcttgcgtta atttttggtg gcacatatca agcgcctcaa cagccttcgc  120
cgccgctttg tcaacaaggt gcgtaagatt gctgcgggtt aacggatcta acgtacagcc  180
aaagttatgt tcaatgcagc tggcaatata gggcatcacc tcctgcataa caagattcgt  240
cgataattta cttaattcac cgccagtgtt atttttgata atatctaaca gctgcttttc  300
caggttttcc agcttcgctt ccgctttctt tgtttctggc agccatggcc caaaagctga  360
cttttctttc aggccatctt ttatgatttg cgcggtatac tctgccccca ccttcatcag  420
tagcgtcttc gcctcaggag aatcactggt ggcgttgagc gctgaacgaa agagcccggc  480
aaactccatt atcgctttct taccggcgac attatttgaa ttggtaaaaa cttcttttaa  540
cgcctcagcg tctttcccgc atttaaacaa tgcatccaga ctcgcctgtt tgatcagcgc  600
gggaaaatct tccagttgcg ggcctttaat ttcccctgac agcgtcgctg tggcactttc  660
```

```
tctgactgcg gaaagattcg ccgcaagatt cgtggcctgc gttttgatct cggtctgcat  720
acctggcatt atgacggggg gctgagtcct tacacttgta accattatta atatcctctt  780
ctgttatcct tgcaggaagc ttttggcggt ttccaggctg ctacttatcg tactgctcag  840
cacttttacc aggttgtcgt acaatgaatt ggcattgcta tatttttgcg tcagcgtctg  900
taatgtggtt ttcatatttt cttcctgcgc tttaaaaccc gactgccagg cttgatattt  960
ggcgttatcc atttcgagtt ttgagtcttt tcccggcgcg cctaaaccat caatatcctg  1020
aaccattttt tgtaatggcg tcagatcaac ggtgacgaca taaccggatc cataagattt  1080
caggcagcta ttcggtaaat tcaattcact gagccactgt ctcgcttccg cttcagtggc  1140
tactttaacg ccgctgcctg actgcgctgg aaataaaacg gtattactgt ttatttgatt  1200
atatttattg actaaactgt ttaaatcatt tttgagtgag gtaacatcta gcttaacggt  1260
attaccgtcc ttacctggta ataaccagcc tcccattttg gaaagaatat cactgaaggc  1320
ctgataaaaa tcggtataga ctgcgacaac gttttcataa acgcccagat agctgtcacc  1380
tatcgccgat atattttggg aaaccatatc ccaaatctca gcatcagaaa tggttgttct  1440
cggctgcgcc ataggcgaag cgctaaataa ggccgacgtc ggcgcagaaa acgcgctccg  1500
caggttctca ttttgttctg cggataatga cacgccggac ttcgccagcg cattcaggct  1560
gctggtcaac tgctggcgcg ccagcgtgcg ctcgtcatta ttctcttcag agatcggtgg  1620
cgttgactgc agcgtctgct gtgcctggtg gattttagta gccgcctgcg ataatgaaat  1680
gatatctgta ccgcgatgtt ctgtggtaga cggtaccacg gcagtctcga cgtgctcgct  1740
cgccgaggga gtctgcggcc gttcggcaac gatccccgga tgaggagaag cggaataatt  1800
ttgaatatta agcataatat ccccagttcg ccatcaggag cgcgattaaa tcacacccat  1860
gatggcgtat agatgacctt tcagattaag cgcgaatatt gcctgcgata gcagcgagtg  1920
cggatgcttt cgactggtta atgctctcca ttgttttcag catttcctga atcaggctgg  1980
tcgatttacg tgaactttca cggcttcgt ccgatgcggt gctggcaacc cggttattca  2040
cctggctaat ttgctgctcg gaacgttcct gagtagcggc gtactgcccg gacgcccctg  2100
caataccacc gaccgtgacc gagttcttca taatcagatc gcccgtcatc tgcatcttgc  2160
gcgcatcgat tcgggtcata tccatggtat tctgctcaag acgaatatcg gattcgacag  2220
actcaagacg tttcgacaga atagcctgat gttcagggga gatttgttta ttactgtctt  2280
taatacccag actttccgtg gcgctggttc cggcattaga tttaagcgtc gcatcattaa  2340
gatttttcgt cgcatcggta ccggttttct tcatatttaa cgatttcaga gaatcgacgc  2400
cttcagcacc gagtttgacg ctattctgcc cgttcagcac gtttttaata ctgtggcttt  2460
cagtggtcag tttatcgatc ttcgcggcat tatgtttaag                        2500

SEQ ID NO: 20          moltype = DNA  length = 2500
FEATURE                Location/Qualifiers
source                 1..2500
                       mol_type = other DNA
                       organism = synthetic construct
SEQUENCE: 20
cgcgcctctt tcattctgca gccccttata ttccagtttg gcgcccacgc cagtgatccc  60
caactgaagc gcgctctggg aaatactacc ggacaacgca ttcatccctt cgcgcatcat  120
ggagcttgcc gtcgttttag ctgcatcaaa actgactaat gacaacttac cagacagttt  180
gctatcagcc tggttcaacg tcagcattaa cgtattcgcg gcagccaaca gcgcaacggc  240
actggaagac attccgctaa tatcaaaaaa ctttccgact tctgcctgct gctcgcgtaa  300
ctgggtttgc acaacctcat tcgctttagt cgtgacatta tttgccagag cattcaaatc  360
ctgattcatg tcggtatttt gaatactggc ttttaaaaag gacgtgatcg ttccgggggt  420
ttgcgttaat accccctggcg caggcgcgct cagtgtagga ctcaacccca ggtcactgac  480
tttactgctg ctaataccaa tactattcag aatatcttta gcgctaacgg attgcgaagc  540
tgtctgtgaa ctattctcaa cagaatgatt atttaaataa gcggcgggat ttattcccac  600
attactaatt aacatatttt tctcccttta ttttggcagt ttttatgcgc gactctggcg  660
cagaataaaa cgcgaagcat ccgcattttg ctgtaccgca gaagacatgg ctttttgcag  720
ttccgccgtt accttctggt tttcaccaaa tatttctacg gattgtttaa gccactgctg  780
aatctgatcc atggcaaaac gggcgagcat aaaatcagca agcgcctcgc tggcattttt  840
aataaatacg ccctcggcaa caccaccggc tgactgggct gcggtattcg tgacttccat  900
gcccaacgcc actttattta gggtattacc taccagctct ttacttaagg cattcgtttg  960
caggcccatc ttgctaccca cattacccag accgctagta atacgttgca tcccctgggt  1020
aaagagtttg ctgccgtttt gcgccaactg tttcagcacg ttaggcacca acttcttaat  1080
cgtttcgccc atcatttgc tcagcgcgtt acccagtttc gccgccgcgc ctttcccgac  1140
aactgcgacc accacaatga ccgccaccat ggcaatagcg gcgacaatcg caccaacaat  1200
gctgccggcc atctctgccg ttttcttatc gacgcctaat ccttccagcg ctttggtaat  1260
cgccttgcca atcagctcca ttaacggctt cagcacatgc tccataatcg ggtttagcgc  1320
ctgctgaata aacgacactc ccgtcgccgc cttcacaatt tcatcggcca ccattaccgc  1380
aagtcccacc gcagccagcg ccagactcgc ccccaccggta aaaacagcgg ccacaacgct  1440
gacaatggtt agcagcgcgc cgaggacttt cccgatacat cccataatgc ggttcgtttc  1500
ctcggctttg cgcgtctctt cctggaattc agccgatttc ttttccatct ccgcctgacg  1560
cccttcctgc aaggcgttga aaagcgcaag atcgttttgc aggctttctt ccgtattttt  1620
gcccacaatc tcaataaaca tggccatgag catagtgagg cgggcgacat ttgacagatt  1680
atcctgctca ccctgggaaa cctgattctg agaggcggca ttagccgttc cctggaattt  1740
ggtcagaatg ttatccgctt tctcggcttt cgctttggcg tctgtgcctg ctttaaccgt  1800
cgcatccgtg gccttatcta aggcctttc cgcctctgtc gcttctttc cggcctgttc  1860
taccgcggct tcagcttgtg catagccggg gtcagccggg tccagcgatt gcaatttatt  1920
ttgcgcctgc gtcagttttt tggtcgcagc gtcataaaca ctcttggcgg tatccgtctt  1980
tttgatactg gcttcataga gatccgtcgc ctcctgagcc tctcccagag ccgtctggaa  2040
ttctttcgat acctgaatcc ccatctcttt ttgtgactca atcatcgcct gccataccgc  2100
cagacgagac tccagttgag acagcgaaac atcgcccagt agggtcatta acttgccaag  2160
cagtaatgtc aattgccctt cgctggagag tttttcccgg gcggcgtccg taggcggctt  2220
tagacccacc gtattaatag cgctctcgcc ggactttgtt ccggctttaa ggtcgcccgc  2280
tttcgttgcc accacatctt taaaagcttt atccgccgct tttaaaaagt ccgtgttctt  2340
acgaacgcct tcaaaagccg cctcagcgag gcgcggattt tgggtatatc cgctacggct  2400
aatgctactt gcgtcattta ccataattat tcctttctt gttcactgtg ctgctctgtc  2460
```

```
tccgccgttt ttagcgcctc cagatagacc aacgcttttg                       2500

SEQ ID NO: 21          moltype = DNA  length = 2218
FEATURE                Location/Qualifiers
source                 1..2218
                       mol_type = other DNA
                       organism = synthetic construct
SEQUENCE: 21
ctatcgtgtc atgtaatctt gcatccgatc ttgcaacgct gtaaatgttt cgaagccatc  60
ctcttctaag aagtgccctc catcttccac gattcgcaag ttcccctcta atgcattcat  120
taaacgctgg gtttctttat atgaaacgta tttgtcattt ttagaactca atccgtaaaa  180
attgtcaact ttctttttaa tattatcgta atcaatggtt acattactta aatcaatatc  240
taaatctata ttttctgcat cttctttaaa gcccgctata ctaaaaaagc cttcaatcgg  300
ctgatcaatc atttcaatat attttaaagc tgtgattgaa cctaaaccat gtgttacaaa  360
atatgtatcc tttttgcgta cattaatttg tttcgtcata gcttcaatcc actgatccac  420
tgtcttcgct tcaggggatt caaaattaaa taatgttacg tcatatcctt ctaaagttaa  480
gttatgctcc aaccactgat accaatgatt tctactattt ccatgcatag aatgtacaat  540
aattacatct gtcatctcat tctctccttt caacttacta cttcttttct atttttaaaa  600
aaatgactga ttacctataa ttgtaaaata aaaacacctt aattagaaat gttatatcgc  660
aaagtgacat ttctaattaa agtgtattgt catcatttca atatcattca aaaacagcta  720
aacctttgtc tctgcttcaa tttcacaaaa ataattcccg ctgaaagtat ctatatttac  780
acattacttc caccattata taacttaaaa atgactatat ttcatcaaac attatctaaa  840
ggcgtcgcac ctacaccaac accatccaac aattaactta caactctgcg attacttctt  900
cagcagcaac tttaccttgt gtaatacaat caggtagtcc aaccgcttca aaagatgcac  960
cagttactct aagtcgtgga tatgtttgtt taatatgtgc ttgaatctgt ctaatttgtt  1020
gaatatgacc gacatggtac tgtggcatac ttttcggcaa acgattgaca attgtaaatt  1080
caggatcacc tttaaatgtc atcatttgac ttaaatctct acgtacaatc gatactaatt  1140
cattatctgt atgatcatca accacagtat cacctggttt acctacatac gcacgaatca  1200
aaaccttacc ttctggtgta gtaaatggcc atttttttcga tgtccaagta catgcggtaa  1260
tgtctgtatc actcgttctc gcaatcacga agccagtacc atcataagta ttttcaatgt  1320
ctttttcatc aaatgccaat acaacagttg caacagtcgt actatccatc gttttaaagt  1380
aatcaaatgc tggatcttgt ccgaaccaat tcaaaaagac ttgatgcggt gttgtcacta  1440
ataccccatc gaatacatct tcttgttgat tactgtaaac aattttatat tgcttttgag  1500
atgtaataat atcatccact gacgtattgt agcgtattgt cacaccttta tttttcacat  1560
cttgttctaa tgcttcaata aatgagctta aaccatgctt aaattgtttg aattgtcctt  1620
ttggtgcgcc aggatataat tgtctttgtt tcagacgctt atttttctca tccttcatac  1680
cttttatcag acttccgaat gcctcttctt tttctttaaa attaggaaac gtactcatca  1740
aacttaattt atcaatatcg gtaccataaa taccacccat taaaggctca attaagttct  1800
caagtacctc attacctaat cttgctctga aaaatgcacc aacagaaatg tcaccatctt  1860
gcatttgtat aggcttttttg attaaatcta atcctgctct taatttacca agtggcgata  1920
ttaattttgt agtaacaaat ggtttaatat ctgttggaat acccataatt gaaccacctg  1980
gaatcggata taatttattt ttcgcaaaaa tatatgattg tccagtcgta tttgtaacaa  2040
tatcttgttc taatccaata tctttcgcta attctgtcat aatcgttttt ctacctaaat  2100
aagattcagg ccctagttca atcatataac catctttacg atacgattga atctttcccc  2160
ccggacgatt cgatgcttca aagatggtta catcaatatt aggatcttgc tgttttaa    2218

SEQ ID NO: 22          moltype = DNA  length = 2775
FEATURE                Location/Qualifiers
source                 1..2775
                       mol_type = other DNA
                       organism = synthetic construct
SEQUENCE: 22
gacttgattt catcaacaat tgcaccgata aataatggat gtgtattcgg catttttgga  60
cgataataat tcgcaccaat atcatcgcaa acaactttac attcataatc attgtcataa  120
agcacctcta aatgctcaca tacaaaacct actggcgtat atataaagtt tttatactga  180
tgtttttcat ataaatcacg tgttaaatct tgtacatctg gccctaacca aggtgtacct  240
gtattacctt cagattgcca accaatcgcg atatgttcaa tattagattg ttctttaatt  300
aaaagcgcag tatgttctag ttcttgtgga tatggatcat tattcttttc gattaaacct  360
tttggcaaac tatgtgccga aacaactaat accgtgtctt tatgttcctc ttccggtatt  420
tgagctaatg tttcgttgac tttattcgtc caatattcaa taaatttagg ttgttcataa  480
taatgtttca catgtgtaag ttgaatacca tattttgcag cttcttcatc agcacgtttg  540
tcatatgatc ctactgaaaa tgaagaataa tgtggtgcta gtactaccgt gattgcttca  600
gtaataccat cattgtgcat ttgttcaacc gcatcttcga taaatggtga aatgtgtttt  660
aatcctaagt atagtttaaa ttcaacatct gcatatgctt tatttaatgc tgaaactagt  720
gcatcagctt ggtcatctgt tgtacctgct aatggtgata aaccacctat aaattcatat  780
ctatctttca aatcttgaag ttcttcttca gatggacgtt taccatgtct aatatctgta  840
taatatggct ctatgtcact ttctttataa ggtgtgccat aagccataac taataacccc  900
attttttttag tcattgataa taccttcctt taaatgaatt atctttcatg tgcttcaatg  960
taatactatg attatctttg tgtatatgtg tgtacgaatt cgcttacttt acgtaacgtc  1020
tctggttgca cttctgggaa aacaccgtgt cctaaattaa agatgtgttt accgttctcc  1080
ataccttgat ctaatattgg tttcaatctc tcttcaatga cattccatgg tgctaataaa  1140
attgatggat ctaaattccc ttgtaatgtt ttagtaacgc ctaattgttg agcctgatta  1200
atagacgttc tccaatctag gcctaataca tcaatcggta aatcattcca ttcattgatt  1260
aaatgactgg cacctacacc gaataaaatt accggcacat catgtttttc tttaacctca  1320
ctgattaatc gaatcatatg tggtttaatg taacgtctgt aatcctcgac atttaatgca  1380
cctacccatg aatcgaaaat ttgaatcaat tcggcacctg cttcgacttg agctgttaca  1440
tatttaacag atacatcaac taaatgattc attaaagcaa accatgttgc ttcatctcta  1500
tacatcatcg cttttgtaaa attgtaattt ttcgatggtc cgccttcaat catatatgac  1560
gctaatgtaa atggtgcccc agtaaatcct attagcggca catttaactt ttcttctgtt  1620
```

```
aaaagtttaa ttgtatctaa tacatatggt acatctcgtt cggggtctat ttgagaaagt  1680
ttctcaacat cttgaattgt tttgatagga ttatgaatca ctggaccaat acccgattta  1740
atttctacat cgacaccaat tggctttaat ggtgtcataa tatctttgta taaaattgct  1800
gcatctgtat gataattatc aactggtaaa tgtgttacat aagcgcacaa ctccggctga  1860
tgtgtaatat cgaatagtga atatttttct ttcaattttc gatattctgg ttgcgaacgg  1920
ccagcttgtc gcataaacca aacaggtgta tgtgatgttt cttcaccttt gatcattttt  1980
aaaattgtat tgtttttatt atgcaccata aaggcctcct aaattaaaat cattcttatc  2040
tatattatca tatcgctcat tcgttcgtat tttcaataaa taaatgtcat aaaactgaca  2100
tttaatcata gaactattta ttgtaaattt aaattctaaa gtccattatt ttgtatcatt  2160
acttctaaat atctcgcaag attcattata gtaattttaa tcaattatta atagtggtaa  2220
tgactagttt atcatcgtat aataaataaa aacataaggg ggacctttca tatgaagaaa  2280
ctatatacat cttatggcac ttatggattt ttacatcaaa taaaaatcaa taacccgacc  2340
catcaactat tccaattttc agcatcagat acttcagtta tttttgaaga aactgatggt  2400
gagactgttt taaaatcacc ttcaatatat gaagttatta aagaaattgg tgaattcagt  2460
gaacatcatt tctattgtgc aatcttcatt ccttcaacag aagatcatgc atatcaactt  2520
gaaaagaaac tgattagtgt agacgataat ttcagaaact ttggtggctt taaaagctat  2580
cgtttgttaa gacctgctaa aggtacaaca tataaaattt atttcggatt tgctgatcga  2640
catgcatacg aagactttaa gcaatctgat gcctttaatg accatttttc aaaagacgca  2700
ttaagtcatt actttggttc aagcggacaa cattcaagtt attttgaaag atatctatac  2760
ccaataaaag aatag                                                  2775

SEQ ID NO: 23          moltype = DNA  length = 2222
FEATURE                Location/Qualifiers
source                 1..2222
                       mol_type = other DNA
                       organism = synthetic construct
SEQUENCE: 23
atgaagcaat atatagtcat tgggtgtggg agatttggaa gttcagttgc gtctactatg  60
catcttttag gacatcaagt aatggcaata gacaaaaatg aagattcagt tcaaagtata  120
tctgacaagg taacccattc acttatagtg gatgttactg atgagcaagc gttaaggtca  180
ttaggtttag gtaactttga tgtagcagta gttgcaatag gttctgatat aagggcatct  240
ataatggcga ctcttatagc caaagaaatg ggtgtagagt tgataaatatg taaggcaaag  300
gatgaattac aagctaaagt gctttataaa attggcgcag atagagttgt atttccagaa  360
agagatatgg gagtaagagt tgcacacaat ttagtttcgg ataatatatt agaccatatt  420
gaacttgacc cagagtattc aattgttgaa atcgtaactc caaatagttg ggttggcaag  480
acacttatag agcttgaatt aagagctaga tatgagataa ctgtacttgc tataaaaaca  540
ggtaaaaata taaatgttac accttctcca gatgaggaac ttacagccgg aagtatccta  600
gttataatcg gtcaaaatac tagtataaca gcgataacat ctggaaataa ggggataatt  660
agaagaagat aatttactat ttaatatata tttaattgca atgaaagtaa agagtatcat  720
ataattatga atagttatat gatactattt ttatttaatc gaaggtagta tttatttgta  780
agattagata aagagaagtt aaattaaaag taaggaggct gtgctaatat aaaaatttat  840
aagttattag catttagata aaatgattac aaatataaac agtaaggata atgaaaagtt  900
aaagtataca agagcactat taaaatcaaa gaataggaat aaagagtcaa agttcataat  960
agaaggatac agaatagtaa tgcttgcact tgaatgtatg gcaaaccttg attatgtatt  1020
tatcaatgaa gaatttgaaa ataagaaaga acatgtaaaa ctattagaag atttggataa  1080
aaaaaacaca aagatataca agactactaa taaaaacttt aaagaattag tggatacaga  1140
aaatactcaa ggaataatag gtgtagtttc atttaagaaa aaaaaattaa gtgaaagtat  1200
aaataaaaaa gataaatttg tattgatttt agatagaata caagacccag gaaatatggg  1260
gactataata aggactgctg attctgctgg agtagatgcc ataatagcac taaagggatg  1320
tgtcgatata tacaacccaa aagtaattag gtctactatg ggttctattt ttgatatgaa  1380
tataattgat gcttcacaag atgaaactgt ggacatgctt aaatcattgg attttaatat  1440
agtttcaagt tacttaaata cagaaaattt ttatgacaaa atagattatg gttcaaaagt  1500
agcattggtg ataggaaacg aagcaaatgg aataaatgaa gaacttgtat caaagtctga  1560
tattttggtt aagataccta tatatggtaa agccgagtcg ttaaatgctg cgataagctc  1620
tgctatactg atgtatgaaa taaaaaaata cttaatttaa tgtattgtaa taaatataat  1680
gtcatgttat aatcttgaat taaatagtag agtatcaaaa atagtcaata tatattaaaa  1740
aaataattaa attaattata tattagatgt atatcatata aaaaatgatt gagttgatta  1800
tgtattagat atatattata taaaaaataa ttgagttaat tatgcattag atgtatatta  1860
tataaaaaat aattgagtta attatgcatt agatatatat tatataaaaa ataattaaat  1920
taattatgta ttggatatat attaaaaata gtcacataat ttgaatggaa atgatataat  1980
actaaaataa acaatataat attgtaaatg caatgaaaga ggaaagtatt ttgattaaac  2040
ttagtaaaga gataaacacc taggctggga gtgttttcta agaggtcatg agaagttccc  2100
tctggagtaa cagagctgaa attttacagt aggctttgac gtcaaaaacg cgttaagttt  2160
gttagaggtg gtttgatgat ttttaaattg ttaaactact agggtggtac cgcgaaacta  2220
ta                                                                2222

SEQ ID NO: 24          moltype = DNA  length = 2530
FEATURE                Location/Qualifiers
source                 1..2530
                       mol_type = other DNA
                       organism = synthetic construct
SEQUENCE: 24
tagacaggga ttgaggggct ttttttatac aaaaaaacga aagggtgata tgtgtgcaag  60
aaaaattact tgctttacgt gaagcagctt tggctgaaat aaaagaagca caaagcatag  120
aaagtgtaga aagtttaaga gttaagtact taggaaaaaa aggtgagata actgccatac  180
ttaaagaaat gggtaaatta tctgctgaag aaagaccagt agttggtaag gttgccaatg  240
aggtaagaga aaacattgaa cttagcataa attctaaaaa agaagaaata aatgctattg  300
aaaaagaaag aaaattaaaa gaggaagtga tagatgttac tcaaccagga aaagttttaa  360
aggttgggaa gaagcatcca ataactcaaa ttatagatga agtaacagat atatttatcg  420
```

-continued

```
gaatgggatt ctctatagca gaagggccag aagttgagac tgttgaaaac aactttgacg  480
cattaaacgc tcctaaagac catccatcaa gagatatgag cgatacattc tatatcaatg  540
atggggtatt acttagaact caaacatctc cagttcaagt aagaactatg agaagtcaag  600
agttaccaat aaaagtaatt gcaccaggta gatgttttag gtcagactcg ccagatgcta  660
cacactcacc aatgttccat cagatagaag ggcttgttgt tggaaaagat gttactatgg  720
cagaatttaa aggaactatg gatatcttcg ttgaaaaatt gtttggttct gatatcaaaa  780
ctaagtttag acctcacaac ttcccattta cagaaccaag tgcagaggtt gatgttactt  840
gtttcaaatg tggtggtaaa ggttgcccaa tgtgtaaata tgaaggttgg atagaaatat  900
taggttcagg tatggttcat ccaaatgtgc ttagaaattg tggaatagac ccagaagttt  960
acagtggatt tgcatttgga gttggggttg aaagacttgc aatgcttaaa tacgaaatag  1020
atgatattag attattattc gaaaatgata tgagattctt aaatcaattt taattaggag  1080
ggtatgtaga tgttagtatc tttaaaatgg cttagagact atgttgatat agacatggat  1140
gtaaaagagt tcgctgataa aatgacaatg acaggaacta aagttgaaac aatagattat  1200
tatggtgaag aaatagaaaa tatattggtt ggaaagattt tagaaataaa acaacatcca  1260
aatgctgata agttggttgt aactaaagta gatattggag ataaagttgt tcaaatagtt  1320
acaggagcta caaatatatc agaaggagat tatattccag tagctgtaaa tggttctaag  1380
ttacctggag gagttgaaat caaacagact gatttcagag gtgaattatc agatggtatg  1440
atgtgttcag cagctgaact aggtatagat gaacattaca ttgaggagta taaaagaggt  1500
ggtatatata ttttagacca cgaagattct tatgaattag gaaaagatat aaaagatgtt  1560
ttaggattaa aagatgcttt aatagatttt gaattaactt caaacagacc tgattgtaaa  1620
tgcatgatgg gtatagctag agaagcagct gcaactatag gaacaaaagt aaaatatcct  1680
gaaatcgaag taaaagaaag tgacgaagag atagatttca aagttgagat agataatcca  1740
gatttatgta gaagatatgt tgctagaatg gttacagatg taaaaataga accttctcca  1800
tattggatgc aaagaagact tacagaagca ggagtaagac ctataagtaa catagtcgat  1860
ataacaaact tcgtaatgtt agagcttggt caaccacttc atgcttttga tataaatcaa  1920
gtagagactg gaagaatagt agtaagaaat gctaaagatg gagagaaact tgtaacatta  1980
gatgatgttg agagaacatt agataaagat atgctagtta taacaaatgg agaaaaatca  2040
cttggtttag ctggtgtaat gggtggtgct aactcagaaa taacttctaa tacgaagact  2100
gtactttttg aaagtgccaa tttcaaacca gaaaacataa gaatgacagc taaaaaagtt  2160
ggtattaggt cagaagcatc ttcaagaaat gaaaaagact tagaccctaa tcttgcagag  2220
atagcagcaa atagagctgc acaacttgtt gaaatgttag gagcaggaaa agttttaaaa  2280
ggtgttgtag atgtatatcc aaataaacca gaacctaaaa aattggtagt aaatcctcaa  2340
agaattaacc acctattagg tgtagatgta ccaatggagc agtttgtagg aattttagaa  2400
tcattagagt ttaaatgtaa tttggtagct aatgataaat tagaaataga tgtaccaagc  2460
tttagaacag atatggaaca agaagctgat gtatgggaag aaatagctag aatttatgga  2520
tttgagaata                                                         2530
```

CELL-BASED DNA SENSORS AND METHODS OF USING SAME

STATEMENT REGARDING FEDERALLY SPONSORED RESEARCH

This invention was made with government support under HR-0011-18-2-0002 awarded by the DOD/DARPA. The government has certain rights in the invention.

SEQUENCE LISTING

The instant application contains a Sequence Listing which has been electronically submitted in XML format and is hereby incorporated by reference in its entirety. The XLM copy was created on Dec. 2, 2022, is named Seq_List-P210411US02.xml and is 54,692 bytes in size.

FIELD OF THE INVENTION

The invention is directed to cell-based DNA sensors and methods of using same for detecting DNA and cells.

BACKGROUND

Chemical and electrical signaling in microbial communities play key roles in biofilm development, activation of virulence pathways, and symbioses with multicellular organisms[53]. These signals can be exploited to control the collective growth or gene expression of the population or mediate interactions between constituent community members[5,55]. For example, circuits have been designed in engineered organisms to sense specific signals produced by pathogens for selective inhibition of growth[7,8]. However, there are limited well-characterized and orthogonal chemical signals systems for building communication networks between strains due to signal crosstalk[9,10]. In addition, there are challenges to engineering these chemical signals for inter-species communications[55,56]. Therefore, new versatile mechanisms are needed for sensing diverse species in microbial communities.

Towards this goal, sensing of bacterial pathogens is a critical and unsolved challenge, as new pathogens can emerge[57]. Current methods for pathogen detection include quantitative PCR (qPCR), immunology-based testing, selective culturing, and Next-Generation Sequencing (NGS)[58-59]. Further, diagnostic tools based on CRISPR-Cas nucleases have also been developed[60,61]. While qPCR is sensitive to the concentration of the target sequence, this method requires specialized equipment and trained personnel which may limit its broad deployment. Immunological detection methods have lower sensitivity and specificity than PCR-based techniques, but have a faster turnaround time. Due to these limitations, new cost-effective, sensitive, generalizable and easy to implement pathogen detection methods are needed.

SUMMARY OF THE INVENTION

The invention provides cell-based DNA sensors. One version of a cell-based DNA sensor comprises a competent cell that comprises a genetic circuit. The genetic circuit preferably comprises a pair of homology arms and at least one of a reporter switch and a kill switch. The pair of homology arms are preferably comprised in a DNA strand. The homology arms preferably comprise a first homology arm and a second homology arm. The first homology arm is preferably homologous to a first portion of a target DNA. The second homology arm is preferably homologous to a second portion of the target DNA. The first portion and the second portion in some versions are contiguous in the target DNA. The first homology arm and the second homology arm are preferably separated within the DNA strand by an interstitial region of the DNA strand. The reporter switch preferably comprises a reporter gene and a negative regulator of the reporter gene. The reporter gene preferably comprises a promoter and a coding sequence that are not comprised within the interstitial region of the DNA strand. The negative regulator of the reporter gene is preferably comprised within the interstitial region of the DNA strand. The kill switch preferably comprises one or more genetic elements effective to inhibit growth of the competent cell. At least one of the one or more genetic elements is preferably comprised within the interstitial region of the DNA strand.

The invention also provides compositions comprising one or more cell-based DNA sensors of the invention. One version of a composition of the invention comprises two or more cell-based DNA sensors. The pairs of homology arms in the two or more cell-based sensors are preferably each homologous to different target DNA sequences. Each of the two or more cell-based DNA sensors preferably comprises the reporter switch. The reporter genes in the two or more cell-based DNA sensors preferably express reporters that are each detectably different from each other.

The invention also provides methods of detecting target DNA with a cell-based DNA sensor of the invention. One version of such methods comprises culturing the DNA sensor in a culture medium comprising the target DNA for a time effective to transform the DNA sensor with the target DNA and detecting the transformed DNA sensor.

The invention also provides methods of detecting a target cell comprising target DNA with a cell-based DNA sensor of the invention. One version of such methods comprises culturing the DNA sensor in a culture medium with the target cell for a time effective to transform the DNA sensor with the target DNA and detecting the transformed DNA sensor.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Schematic of a synthetic genetic circuit constructed in *B. subtilis* that allows the recognition of specific extracellular DNA. The xylose-inducible master regulator of competence comK can induce *B. subtilis* to take up eDNA and undergo homologous recombination. The toxin-antitoxin system txpA-ratA and a distal fluorescent reporter gfp are regulated by the repressor lac. The target sequences are split into two and introduced to the flanking region of toxin and repressor as landing pad. In the presence of target DNA, homologous recombination can remove the toxin and the repressor, so a sub-population of transformed cells can express GFP. To select the transformed cells, IPTG can induce the toxin to kill the non-transformed cells, so the fluorescence can be enhanced by the growth of transformed cells. (FIG. 1B) Line plot of transformation efficiency versus transformation time for the *E. coli* DNA sensor in the presence (solid lines) or absence (dashed lines) of 100 ng/mL purified *E. coli* gDNA as input. The colonies on agar plate can be fluorescent (green) or not (blue), coming from background escape mutation or transformation. Transformation efficiency as output is optimal at 10 hr. Data points represent three biological replicates and lines are the average of the replicates. (FIG. 1C) Line plot of transformation efficiency versus homology length of *E. coli* xdhABC operon on each side of flanking region in the circuit in the presence (solid lines) or absence (dashed lines) of 100 ng/mL purified *E. coli* gDNA as input. The colonies on agar plate can be fluorescent (green) or not (blue). The transformation efficiency as output is above the background escape mutation when the homology length is equal or greater than 1 kbp and increases as the homology increases. Data points represent three biological replicates and lines are the average of replicates.

(FIG. 2A) Transformation efficiency of DNA sensors that can detect *E. coli* (EC sensor), *S. typhimurium* (ST sensor), *S. aureus* (SA sensor), or *C. difficile* (CD sensor) in the presence of 100 ng/mL extracted gDNA (triangles) or no gDNA (circles) at 10 hr. Bar represents the average of three biological replicates. (FIG. 2B) Schematic of experimental procedure for quantifying GFP expression after transformation. (FIG. 2C) Time-series measurements of GFP expression of EC sensor in liquid medium after the transformation of varying *E. coli* gDNA concentrations (ng/mL). A threshold of GFP 400 was used to determine the detection time for each gDNA concentration. Line is the average of four technical replicates and the shaded region represents one standard deviation from the average. Detection time versus gDNA concentration for (FIG. 2D) EC sensor, (FIG. 2E) ST sensor, (FIG. 2F) SA sensor, and (FIG. 2G) CD sensor. Horizontal line (pale color) is the background GFP fluorescence in the absence of gDNA. Unpaired t-test was performed to determine if the detection time with specific DNA concentration is different from the background fluorescence, and *, , and * denote p-values <0.05, 0.01 and 0.001, respectively. A straight line was fitted to the transformation efficiencies versus logarithmic gDNA concentrations with statistical differences. The slope of the fitted line was determined by the cell growth of *B. subtilis*, while the intercept was determined by the background escape mutation. The coefficient of determination $R^2$ shows the goodness of the fit. (FIG. 2H) Detection time of each DNA sensor after the transformation of 100 ng/mL gDNA of a given donor species or no gDNA representing the negative control (NC). Each sensor expressed GFP 3~4 hours earlier in the presence of gDNA from its target strain than gDNA from other strains. Data are the average of four technical replicates. (FIG. 2I) Nucleotide BLAST search of 5000 bp *S. aureus* hemEH in the NCBI database. Each circle represents a homolog found in species other than *S. aureus* and its coverage and identity similarity. A closely related human commensal strain *S. epidermidis* with high coverage and similarity was selected for specificity test using SA sensor. The region within dashed lines indicates *Staphylococcus* species that could be recognized by the SA sensor based on their high similarity of homologous sequences. (FIG. 2J) Comparison of colony numbers of SA sensor (with GFP expression) on selective agar plate after the transformation of 100 ng/mL *S. aureus* gDNA, 100 ng/mL *S. epidermidis* gDNA or no gDNA. Bar represents the average of three technical replicates. SA sensor can distinguish between *S. aureus* and closely related *S. epidermidis*. (FIG. 2K) Nucleotide BLAST search of 5000 bp *C. difficile* pheST in the NCBI database. Each circle represents a homolog found in species other than *C. difficile* and its coverage and identity similarity. A closely related human commensal strain *C. hiranonis* with high coverage and similarity was selected for specificity test using CD sensor. The region within dashed lines indicates *Clostridium* species that could be recognized by the CD sensor based on their high similarity of homologous sequences. (FIG. 2L) Comparison of colony numbers of CD sensor (with GFP expression) on selective agar plate after the transformation of 100 ng/mL *C. difficile* gDNA, 100 ng/mL *C. hiranonis* gDNA or no gDNA. Bar represents the average of three technical replicates. CD sensor can distinguish between *C. difficile* and closely related *C. hiranonis*.

(FIG. 3A) Schematic of experimental procedure using the living cell-based DNA sensors for multiplexed detection. *E. coli, S. typhimurium*, and *S. aureus* DNA sensors were labeled GFP (EC-G), RFP (ST-R) and BFP (SA-B) for detection, respectively. Three sensors and gDNA extracted from different strains were mixed into liquid medium for transformation.

Transformed cells were selected on agar and colonies expressing GFP, RFP and BFP can indicate the presence of target DNA. (FIG. 3B) Numbers of GFP, RFP, or BFP-expressing colonies on agar plate after the transformation of different combinations of gDNA extracted from *E. coli, S. typhimurium*, or *S. aureus*. Sensors can report the presence of target DNA for all 8 different combinations. Bar represents the average of three technical replicates. (FIG. 3C) Relative abundance of six species in a synthetic gut microbial community composed of *S. aureus* (SA), *S. typhimurium* (ST), *Bifidobacterium longum* (BL), *Bacteroides thetaiotaomicron* (BT), *Anaerostipes caccae* (AC), and *Clostridium asparagiforme* (CG) over two days of growth. The six bacteria were co-cultured in liquid medium anaerobically for 24 hours and cell culture was diluted in fresh medium once for species to continue their competition. 16S rRNA gene of each strain was PCR amplified and sequenced using NGS to determine the relative abundance over time. Bar represents the average of three technical replicates of 16S rRNA sequencing. *S. typhimurium* abundance remained similar while *S. aureus* abundance decreased over time. (FIG. 3D) Representative fluorescence images of transformed SA-G and ST-R sensors on selective agar plate after the transformation of gDNA extracted from the bacterial community in a mixture of SA-G and ST-R sensors. The numbers of green and red colonies indicate the abundance of *S. aureus* and *S. typhimurium* in gut microbial community, respectively. (FIG. 3E) Numbers of GFP or RFP-expressing colonies on agar plate after the transformation of gDNA extracted from the community at different time. Green colonies (SA-G) decreased over time while red colonies (ST-R) remained similar numbers. Bar represents the average of three technical replicates. (FIG. 3F) Fold change of *S. aureus* and *S. typhimurium* abundance compared to day 1 characterized by NGS (dashed line) or cell-based detection method (solid line). Measurements of *S. aureus* (orange) by the two methods were similar, while characterization of *S. typhimurium* (green) by the cell-based detection method had larger variability than NGS and the data at Day 1 were statistically different determined by Unpaired t-test (p-values=0.0015).

(FIG. 4A) Schematic of experimental design for the detection in the co-culture.

Sensor and target strain were co-cultured in liquid medium with or without selective antibiotics (ABX) to determine the effect of antibiotic for detection. Heat-killed target strain was also tested without the use of antibiotics in the co-culture. The cell culture was plated on IPTG and ABX (1 μg/mL erythromycin and 25 μg/mL lincomycin) agar plates to select for transformed *B. subtilis*. (FIG. 4B) Colony numbers of transformed EC, ST, SA, and CD sensors co-cultured with (1) target cell, (2) target cell and 100 μg/mL spectinomycin (spec), (3) target cell, spec, and 1 unit/mL DNase I, and (4) spec only. Spectinomycin can enhance the detection of *E. coli, S. typhimurium*, and *S. aureus*, but it is not required for *C. difficile* detection. Addition of DNase I in the co-culture reduced the numbers of transformed sensors significantly. (FIG. 4C) Colony number of transformed EC sensor co-cultured with *E. coli* using spectinomycin or co-cultured with heat-treated *E. coli*. Heat treatment of *E. coli* can significantly increase the number of transformed EC sensor. (FIG. 4D) Colony number of transformed EC-G and ST-R sensors co-cultured with heat-treated mice cecal samples spiked in with different amounts of *E. coli* and *S. typhimurium*. Both sensors can detect the presence of target strains in cecal samples. Unpaired t-test was performed to determine if the colony number is different from no cell condition, and *, , and * denote p-values <0.05, 0.01, and 0.001, respectively. Bar represents the average of three technical replicates.

(FIG. 5A) Plasmid constructed for the DNA detection via homologous recombination. The toxin-antitoxin system txpA-ratA is regulated by the repressor lacI, both of which are flanked by 2.5 kbp target DNA sequence on each side. The plasmid was integrated into the amyE locus on the *B. subtilis* PY79 genome by spectinomycin selection. (FIG. 5B) Plasmid constructed for the fluorescent reporter after DNA detection. The green fluorescent protein gfp(Sp) is regulated by the distal repressor lac. The plasmid was integrated into the ycgO locus on *B. subtilis* PY79 genome by chloramphenicol selection. The green fluorescent protein gfp(Sp) was codon-optimized for *Streptococcus pneumoniae* and displayed high fluorescence signal in *B. subtillis*[51]. (FIG. 5C) Modularity of the synthetic genetic circuit allows customized target DNA sequence as input and gene expression as output.

(FIGS. 6C and 6D) Sanger sequencing of transformed *E. coli* sensor confirmed the homologous recombination at the predicted region that removed the whole cassette of txpA-ratA and lacT. (FIG. 6E) Sanger sequencing of a GFP-expressing escape mutant shows deletion in the toxin txpA. The mutant can grow and express GFP in the presence of IPTG due to the non-functional toxin. (FIG. 6F) Sanger sequencing of a non-fluorescent escape mutant shows deletion of R195 and L196 in the repressor lacI, which has been shown to affect IPTG binding[52]. The mutant can grow but cannot express GFP in the presence of IPTG due to the non-functional LacI.

(FIG. 7A) Nucleotide BLAST search of 5000 bp *S. typhimurium* sipBCDA in the NCBI database. Each circle represents a homolog found in species other than *S. typhimurium* and its coverage and identity similarity. Homologs were found mostly in the *Salmonella enterica* (*S. enterica*) species but were rarely found in other species. (FIG. 7B) Nucleotide BLAST search of 5000 bp *E. coli* MG1655 xdhABC in the NCBI database. Each circle represents a homolog found in species other than *E. coli* and its coverage and identity similarity. Homologs were found in closely related *Shigella* and *Escherichia* species. Highly similar homologs were found in the closely related *Shigella* species.

(FIG. 11A) Colony number per 5 μL for transformed *B. subtilis* with or without 100 ng/mL target gDNA. (FIG. 11B) Colony number per $10^{-4}$ μL for total *B. subtilis* with or without 100 ng/mL target gDNA. Bar represents the average of three biological replicates. The transformation efficiency in FIG. 2A was calculated by the ratio of the density of transformed *B. subtilis* to the density of total *B. subtilis* shown here.

(FIG. 13A) Relative abundance of six species in a synthetic gut microbial community composed of *Bifidobacterium longum* (BL), *Bacteroides* thetaiotaomicron (BT), *Anaerostipes caccae* (AC), and *Clostridium asparagiforme* (CG). The four bacteria were co-cultured in liquid medium anaerobically for 24 hours and cell culture was diluted in fresh medium once for species to continue their competition. 16S rRNA gene of each strain was PCR amplified and sequenced using NGS to determine the relative abundance over time. (FIG. 13B) Numbers of GFP or RFP-expressing colonies on agar plate after the transformation of gDNA extracted from the community at different time in a mixture of SA-G and ST-R sensors. Bar represents the average of three technical replicates of 16S rRNA sequencing. Only a few colonies appeared on agar plates, indicating that sensors did not detect the gDNA of *S. aureus* or *S. typhimurium*. Bar represents the average of three technical replicates.

(FIG. 15A) Synthetic genetic circuit for repressor-based toxin expression. (CRISPRi is listed as a repressor in FIG. 15A for convenience but is properly categorized as a "negative regulator" using the terminology employed herein.) (FIG. 15B) Synthetic genetic circuit for activator-based toxin expression. (FIG. 15C) Synthetic genetic circuit for counter-selectable marker-based DNA detection. (FIG. 15D) Synthetic genetic circuit for selectable marker-based DNA detection. (FIG. 15E) Synthetic genetic circuit for autonomous DNA detection (toxin expresses as cell density increases). (FIGS. 15F and 15G) Synthetic genetic circuits with a negative regulator (inducible regulator) comprised within the interstitial region (FIG. 15F) and outside the interstitial region (FIG. 15G) (Y is a growth inhibitor gene, and X is a positive regulator of the growth inhibitor gene). (FIGS. 15H and 15I) Synthetic genetic circuits with a negative regulator (inducible regulator) comprised within the interstitial region (FIG. 15H) and outside the interstitial region (FIG. 15I).

DETAILED DESCRIPTION OF THE INVENTION

Figure 1A:
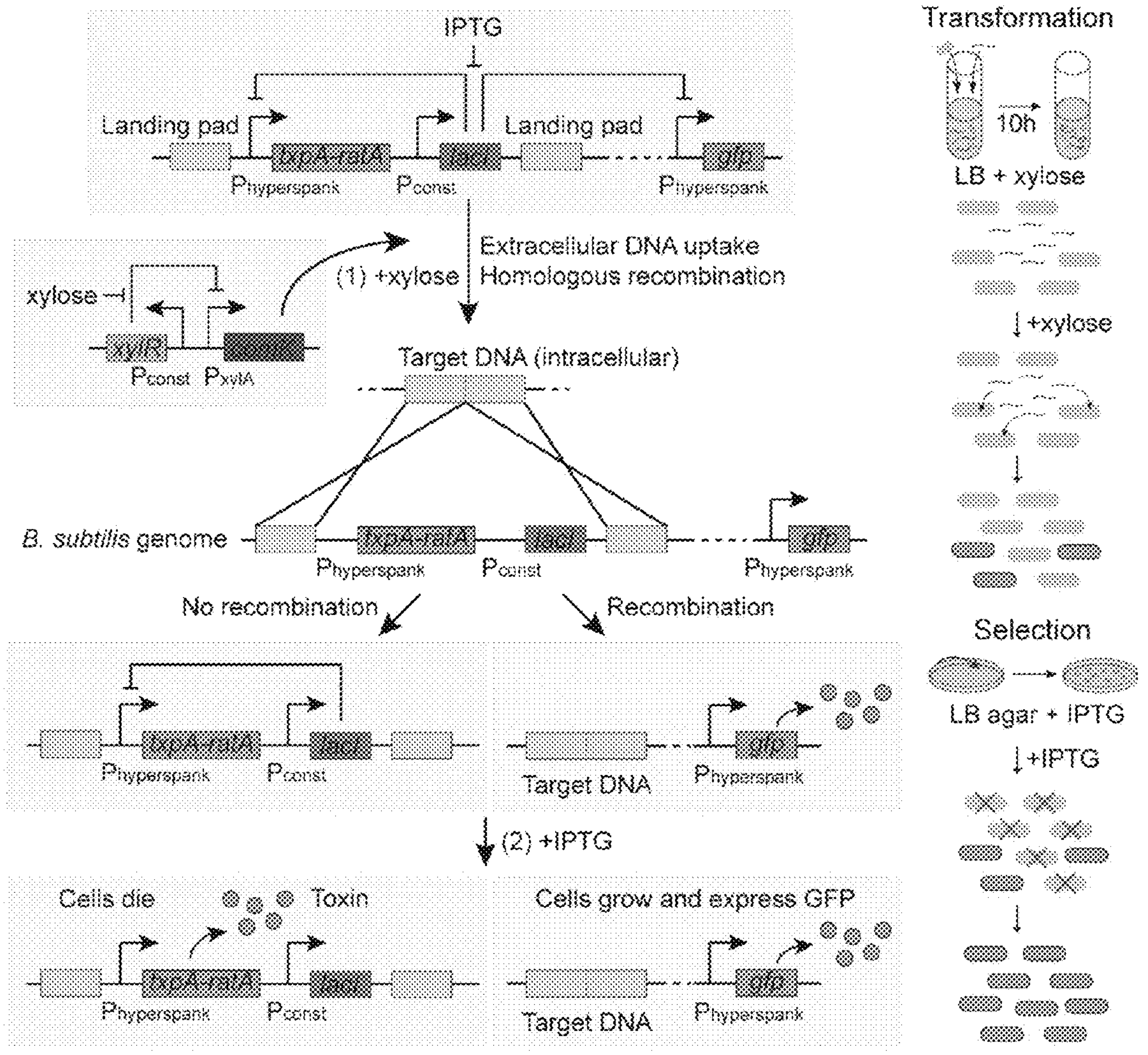
FIGS. 1A-1C. Construction and characterization of a living cell-based DNA sensor.
Figure 1B:
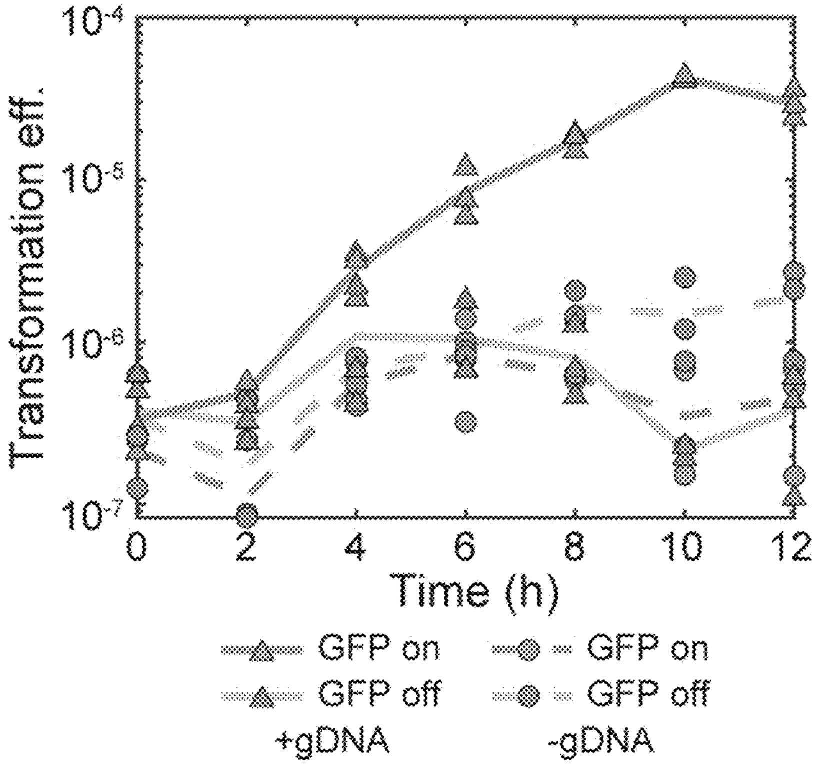

An aspect of the invention is directed to cell-based DNA sensors (also referred to herein as "DNA sensors"). The DNA sensors comprise competent cells. "Competent cell" refers to a cell capable of taking up extracellular DNA from its surrounding environment. The competent cells can be naturally competent cells or artificially competent cells.

Naturally competent cells are cells that, in their unmodified state, are capable of taking up external DNA. Naturally competent cells are not necessarily in a constant state of competence. Natural regulation of competence is common among naturally competent cells. *Streptococcus pneumoniae*, for example, is a naturally competent bacterium, but its competence at a given point in time is prompted by quorum sensing (detecting and responding to cell population density through gene expression). More than more than 80 species of bacteria are known to be naturally competent, including both Gram-positive and Gram-negative bacteria (Johnston, C., Martin, B., Fichant, G., Polard, P., and Claverys, J. P. (2014). Bacterial transformation: distribution, shared mechanisms and divergent control. *Nat. Rev. Microbiol.* 12, 181-196). Exemplary naturally competent cells include members of the *Bacillus* genus, such as *Bacillus subtilis*; members of the *Streptococcus* genus, such as *Streptococcus pneumoniae*; members of the *Neisseria* genus, including *Neisseria gonorrhoeae* and *Neisseria meningitidis*; members of the *Haemophilus* genus, such as *Haemophilus influenzae*; members of the *Helicobacter* genus, such as *Helicobacter pylori*; members of the *Acinetobacter* genus, such as *Acinetobacter baylyi*; members of the *Vibrio* genus, such as *Vibrio cholerae*; members of the *Thermus* genus, such as *Thermus thermophilus*; and *Synechococcus* sp., among others.

Naturally competent cells can be modified to increase competency. Such cells are still considered to be naturally competent in light of their competency in their natural, unmodified state. Naturally competent cells, for example can be modified to express genes that increase competence. An example of such a gene is comK. Other genes or modifications that increase competency are known in the art.

Artificially competent cells are cells that are not capable of taking up external DNA in their unmodified state but are modified to do so. Artificially competent cells include chemically competent cells and electrocompetent cells. Chemically competent cells are cells that are made competent with a chemical treatment. Comment treatments include a salt treatment followed by a heat-shock step. This process permeabilizes the cell membrane, allowing entry of DNA. Protocols using $CaCl_2$) or $MgCl_2$ are the most common method for making chemically competent cells, but other salts and chemicals can be used. These include dimethyl sulfoxide (DMSO), polyethylene glycol (PEG), and rubidium chloride (RbCl). Electrocompetent cells are made competent using an electrical pulse from an electroporator to create temporary pores (poration) in the cell membrane. An exemplary artificially competent cell is *Saccharomyces cerevisiae*, which can be artificially induced into competence and have stronger homologous recombination and may detect short DNA sequences.

The competent cells of the invention can be prokaryotic cells or eukaryotic cells. In exemplary versions of the invention, the competent cells are prokaryotic cells, such as naturally competent prokaryotic cells, such as *Bacillus subtilis.*

The competent cells of the invention can comprise a genetic circuit. A genetic circuit is a combination of genetic elements that enable a cell to perform a logical function. As used herein, "genetic element" refers to any sequence of DNA that confers a genetic function. Exemplary genetic elements, include genes, promoters, exons, introns, enhancers, silencers, 5' untranslated regions, 3' untranslated regions, open reading frames, coding regions, codons, terminators, etc. In the context of the present invention, an exemplary logical function is the detection of DNA.

The genetic circuits of the invention can comprise a pair of homology arms on a DNA strand. Each homology arm is a portion of DNA in the genetic circuit that has a sequence homologous to target DNA. The homology arms in each pair are configured to excise a portion of DNA from the DNA strand through homologous recombination with a target DNA. To perform this function, the homology arms are spaced apart on the DNA strand to form an interstitial region therebetween and together have homology to one or more homologous sequences in the target DNA. Homologous recombination of the homology arms with the target DNA thereby excises the interstitial region from the DNA strand. "Strand" in this context refers to a contiguous, connected sting of nucleic acid bases. The DNA strand can be a portion of the competent cell's chromosome or a portion of an extra-chromosomal DNA, such as a plasmid. In some versions, the homology arms are homologous to a single, continuous sequence in the target DNA (contiguous portions of the target DNA). In some versions, the homology arms are homologous to two separated sequences in the target DNA. The number of bases separating the homologous sequences in the target DNA can vary depending on the length of the homology arms, with longer homology arms permitting further separation (separation being defined as the number of bases between the homologous sequences). In various versions, the homologous sequences are contiguous or separated by 1, 2, 3, 4, 5, 6, 7, 8, 9, 10, 20, 50, 100, 250, 500, 1000, 2,500, 5,000, 7,500, 10,000 or more bases, or any range therebetween any two of the foregoing values.

The terms "homologous" and "homology," used herein with reference to sequences or portions of DNA, refer to having a sufficient length and sequence identity to be exchanged by homologous recombination in a competent cell of the invention.

Each homology arm in the genetic circuits of the invention preferably comprises a length of at least 0.025 kbp (kilobase pairs), such as at least 0.050 kbp, at least 0.070 kbp, at least 0.075 kbp, at least 0.1 kbp, at least 0.5 kbp, at least 1 kbp, at least 1.5 kbp, at least 2 kbp, or at least 2.5 kbp. Each homology arm in the genetic circuits of the invention can comprises a length up to 3 kbp, up to 5 kbp, up to 10 kbp, up to 25 kbp, up to 50 kbp, up to 75 kbp, up to 100 kbp, up to 250 kbp, up to 500 kbp, up to 750 kbp, up to 1,000 kbp, up to 1,250 kbp, up to 1,500 kbp, up to 1,750 kbp, up to 2,000 kbp, up to 2,250 kbp, up to 2,500 kbp, up to 2,750 kbp, up to 3,000 kbp, or more.

Each homology arm in the genetic circuits of the invention preferably comprises at least 75% sequence identity, at least 77% sequence identity, at least 80% sequence identity, at least 85% sequence identity, at least 90% sequence identity, at least 91% identity, at least 92% identity, at least 93% identity, at least 94% identity, at least 95% identity, at least 96% identity, at least 97% identity, at least 98% identity, at least 99% identity, or 100% identity, to a portion of a target DNA. Such sequence identity is preferably assessed over the entire length of the homology arm, such as a length as defined in the preceding paragraph.

The term "sequence identity" (or "identity"), in the context of percent sequence identity, refers to the percentage of bases (or residues) in two sequences that are the same when aligned for maximum correspondence, as measured using a sequence comparison or analysis algorithm such as those described herein. For example, if when properly aligned, the corresponding segments of two sequences have identical bases (or residues) at 5 positions out of 10, the two sequences have a 50% identity. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)). One example of an algorithm that is suitable for determining percent sequence identity and sequence similarity for purposes of defining homologs is the BLAST algorithm, which is described in Altschul et al., *J Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

The homology arm pairs in the genetic circuits are preferably spaced on the DNA strand such that the interstitial region has a length of at least 0.001 kbp, at least 0.01 kbp, at least 0.05 kbp, at least 0.1 kbp, at least 0.5 kbp, at least 1 kbp, at least 1.25 kbp, at least 1.5 kbp, at least 1.75 kbp, at least 2 kbp, at least 2.5 kbp, at least 3 kbp, at least 3.5 kbp, at least 4 kbp, at least 4.5 kbp, or at least 5 kbp. In various versions of the invention, the interstitial region has a length up to 5 kbp, up to 10 kbp, up to 15 kbp, up to 20 kbp, up to 25 kbp, up to 30 kbp, up to 35 kbp, up to 40 kbp, up to 45 kbp, up to 50 kbp, up to 55 kbp, up to 60 kbp, up to 65 kbp, up to 70 kbp, up to 75 kbp, up to 80 kbp, up to 85 kbp, up to 90 kbp, up to 95 kbp, up to 100 kbp, or more.

The genetic circuits of the invention can comprise genes. "Gene" as used herein refers to the combination of genetic elements effective for the expression of a gene product such as RNA (e.g., mRNA, microRNA, etc.) and/or a protein. Genes typically minimally include a promoter and a coding sequence. Genes can also include other genetic elements, including enhancers, silencers, etc.

The genetic circuits of the invention can comprise a reporter gene. A reporter gene is a gene that expresses a reporter. The reporter can be any detectable gene product, such as any protein or RNA (e.g., mRNA, microRNA, etc.). Depending on the reporter, the reporter can be detected by visual inspection, Western blotting, Northern blotting, and mRNA sequencing and quantitation, among other methods. Reporters and reporter genes are well known in the art. Examples of common reporters include fluorescent proteins (e.g., green fluorescent protein (GFP), yellow fluorescent protein (YFP), blue fluorescent protein (BFP), red fluorescent protein (RFP), etc.), enzymes or colorimetric reporter proteins (e.g., β-galactosidase, β-D-galactopyranoside (lacZ)), luminescent proteins (e.g., luciferase), and fluorescent RNA aptamers (Bai, J., Luo, Y., Wang, X. et al. A protein-independent fluorescent RNA aptamer reporter system for plant genetic engineering. Nat Commun 11, 3847 (2020)), among others.

The genetic circuits of the invention can comprise a growth inhibitor gene. A growth inhibitor gene is a gene that expresses a gene product that kills or otherwise inhibits the growth and proliferation of a cell in which it is expressed. Examples of growth inhibitor genes include toxin genes and counter-selectable marker genes. Toxin genes are genes that express a gene product that kills a cell in which it is expressed in a non-regulatable manner. Toxin genes are well-known in the art. Examples of common toxin genes include txpA[49], mazF[50], and hewl[51], among others. Counter-selectable marker genes are genes that express a gene product that kills a cell in which it is expressed in the presence or absence of a particular condition. In some cases, the condition is the presence or absence of a particular compound or chemical. Counter-selectable marker genes are well known in the art (see, e.g., Reyrat, J M et al. "Counterselectable markers: untapped tools for bacterial genetics and pathogenesis." Infection and immunity vol. 66, 9 (1998): 4011-7). Exemplary counter-selectable marker gene/chemical combinations include upp/5-fluorouracil[52], pheS*/p-chloro-phenylaanines[53], and ysbC/fluoro-orotate[54]. Counter-selectable maker genes are sometimes referred to as negative selectable marker genes.

The genetic circuits of the invention can comprise selectable marker genes. "Selectable marker gene" as used herein refers to a gene that confers a trait suitable for positive selection. Selectable marker genes are well known in the art. Selectable marker genes are often antibiotic resistance genes, which typically produce a protein that provides cells expressing the protein with resistance to an antibiotic. Normally, the genes confer resistance to antibiotics such as ampicillin, chloramphenicol, tetracycline, neomycin, or kanamycin, among others. Other common selectable marker genes are genes that are necessary for an organism to synthesize a particular compound required for survival or growth, e.g., for use in auxotrophic selection. Exemplary selectable marker/function combinations include neo/neomycin resistance[55] and lysA/lysine production[56], among others.

The genetic circuits of the invention can comprise negative regulators of genes. The term "negative regulator" used in reference to regulating a gene refers to any genetic element or combination of elements capable of negatively regulating a gene. "Negatively regulating" (and grammatical variants thereof) as used herein refers to inhibiting, reducing, or repressing expression of a gene or reducing the abundance of a gene product of a gene. The negative regulation of a gene can operate at any step of the expression of the gene, including the transcription of the gene to mRNA and/or the translation of the mRNA to a protein. The negative regulation can also or alternatively operate on the gene products themselves, including reducing the abundance of expressed mRNA or protein (e.g., by specific degradation). Exemplary systems or methods of negatively regulating a gene include siRNA, RNAi, and CRISPRi[59]. Exemplary proteins capable of negatively regulating a gene include repressors (otherwise known as repressor proteins). Repressors are proteins that repress the expression of a gene, typically by binding to an element of the gene, such as its promoter. Some repressors are inducible repressors. Inducible repressors are repressors that repress the expression of a gene in an inducible manner depending on the absence or presence of an inducer, whereby the inducer either activates repression or inhibits repression. A number of inducible repressor/promoter/inducer combinations are known in the art. These include lacI/$P_{hyperspank}$/IPTG[57], xylR/$P_{xyla}$/xylose[58], and cI/$P_R$ promoter/temperature increase[55], among others. A gene that expresses a repressor is referred to herein as a "repressor gene."

The genetic circuits of the invention can comprise positive regulators of genes. The term "positive regulator" used in reference to regulating a gene refers to any genetic element or combination of elements capable of positively regulating a gene. "Positively regulating" (and grammatical variants thereof) as used herein refers to stimulating expression of a gene or protecting the abundance of any gene product. The positive regulation of a gene can operate at any step of the expression of the gene, including the transcription of the gene to mRNA and/or the translation of the mRNA to a protein. The positive regulation can also or alternatively operate on the gene products themselves, including protecting or maintaining the abundance of expressed mRNA or protein (e.g., from specific degradation). Exemplary systems or methods of positively regulating a gene include CRISPRa (Liu, Y., Wan, X. & Wang, B. Engineered CRISPRa enables programmable eukaryote-like gene activation in bacteria. Nat Commun 10, 3693 (2019)). Exemplary proteins capable of negatively regulating a gene include activators (otherwise known activator proteins). Activators are proteins that activate the expression of a gene, typically by binding to an element of the gene, such as its promoter. Some activators are inducible activators. Inducible activators are activators that activate the expression of a gene in an inducible manner depending on the absence or presence of an inducer, whereby the inducer either stimulates activation or represses activation. A number of inducible activator/promoter/inducer combinations are known in the art. These include exemplary activator/promoter/inducer combinations include spaR/$P_{spaS}$/subtilin[60] liaR/$P_{liaI}$/bacitracin[61], and ccaR/$P_{cpcG2}$/green light[62], among others. A gene that expresses an activator is referred to herein as an "activator gene."

Quorum-sensing genes can also be employed as positive regulators of genes. Quorum sensing is a specific type of regulation of gene expression in bacteria that is dependent on population density. Quorum-sensing systems include two components: a regulator (autoinducer) and a regulatory receptor protein that interacts with the regulator. The regulator is typically of low-molecular-weight and readily diffuses through the cytoplasmic membrane. As the bacterial population reaches a critical density level, autoinducers accumulate to a threshold value, the regulatory receptor becomes activated, and activation (induction) of genes comprising response elements to the regulatory receptor protein occurs. A gene intending to be positively regulated according to the present invention can comprise or be modified to comprise a promoter sensitive to a regulatory receptor protein of a quorum-sensing system. Autoinducers produced in response to cell density thereby stimulate the regulatory receptor protein to activate expression of such a gene. See e.g., FIG. 15E. A gene that expresses a regulatory receptor protein of a quorum-sensing system is referred to herein as a "quorum-sensing gene."

The genetic circuits of the invention can comprise a reporter switch. A reporter switch is a combination of genetic elements configured to express a reporter from a reporter gene in response to a certain condition. The condition in the reporter switches of the present invention is preferably the presence of a target DNA.

In preferred versions of the invention, the reporter switch comprises a reporter gene in combination with a negative regulator of the reporter gene. The reporter gene preferably comprises a promoter and coding sequence that is not comprised within the interstitial region of the DNA strand. In some versions, no part of the reporter gene is comprised within the interstitial region of the DNA strand. "Not comprised within the interstitial region" as used herein with reference to a particular element means that no portion of that particular element is included within the interstitial region. The negative regulator of the reporter gene is preferably comprised within the interstitial region of the DNA strand. "Comprised within the interstitial region" as used herein with reference to a particular element means that at least some portion of the element is included within the interstitial region. In reporter switches comprising a reporter gene with a promoter and coding sequence not comprised within the interstitial region of the DNA strand and a negative regulator of the reporter gene comprised within the interstitial region of the DNA strand, the negative regulator of the reporter gene remains intact in the genetic circuit in the absence of target DNA and thereby inhibits expression of the reporter under such conditions. In the presence of target DNA, however, the negative regulator of the reporter gene is excised from the DNA strand, thereby permitting expression of the reporter gene for detection.

The genetic circuits of the invention can comprise a kill switch. The kill switch comprises one or more genetic elements configured to inhibit growth of the competent cell in response to a certain condition. "Inhibit growth of the competent cell" in this context refers to killing the cell or otherwise inhibiting its proliferation. The condition in the reporter switches of the present invention preferably comprises the absence of a target DNA. The condition may comprise other aspects, such as the presence or absence of an inducer. In preferred versions, at least one of the one or more genetic elements is comprised within the interstitial region of the DNA strand. In such a configuration, the kill switch remains intact in the absence of target DNA, thereby maintaining the ability to inhibit growth of the competent cell with the kill switch. In the presence of target DNA, however, the interstitial region and at least a portion of the kill switch is excised from the DNA strand, thereby removing the ability to inhibit growth of the cell with the kill switch and thereby permitting growth of the cell.

In some versions, the interstitial region comprises at least one of a growth inhibitor gene, a positive regulator of a growth inhibitor gene, and a negative regulator of a selectable marker gene. In such configurations, the interstitial region the growth inhibitor gene, the positive regulator of the growth inhibitor gene, and/or the negative regulator of the selectable marker gene remain(s) intact in the kill switch in the absence of target DNA, thereby maintaining the ability to inhibit growth of the competent cell with these elements. In the presence of target DNA, however, the growth inhibitor gene, the positive regulator of the growth inhibitor gene, and/or the negative regulator of the selectable marker gene comprised within the interstitial region is excised from the DNA strand, thereby removing the ability to inhibit growth of the cell and thereby permitting growth of the cell with these elements. In some versions, the growth inhibitor gene included in the interstitial region comprises at least one of a toxin gene and a counter-selectable marker gene. In some versions, the positive regulator of the growth inhibitor gene included in the interstitial region comprises at least one of a quorum-sensing gene and an activator gene. In some versions, the negative regulator of the selectable marker gene included in the interstitial region comprises a repressor gene.

Figure 14A:
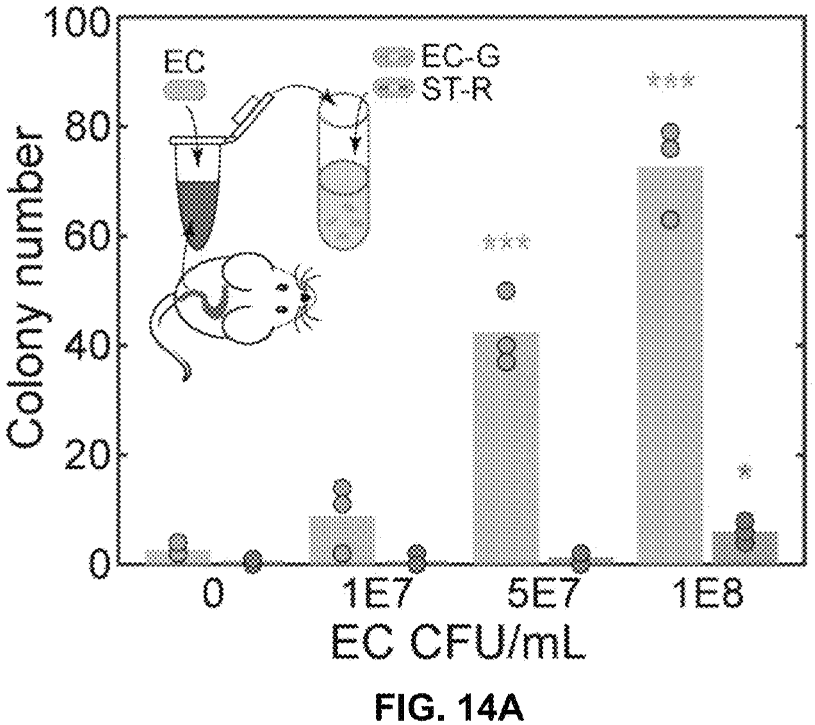
FIGS. 14A and 14B. Detection of *E. coli* or *S. typhimurium* in cecal samples using mixed EC-G and ST-R sensors. Colony number of transformed EC-G and ST-R sensors co-cultured with heat-treated cecal samples spiked in with different amounts of (FIG. 14A) *E. coli* or (FIG. 14B) *S. typhimurium*. High density ($10^8$ CFU/mL) of *E. coli* and *S. typhimurium* can lead to false positive results for ST-R and EC-G, respectively. Unpaired t-test was performed to determine if the colony number is different from no cell condition, and *, , and * denote p-values <0.05, 0.01, and 0.001, respectively. Bar represents the average of three technical replicates.

In some versions, the kill switch comprises a toxin gene comprised within the interstitial region and a repressor gene that expresses a repressor of the toxin gene. The repressor of the toxin gene preferably expresses an inducible repressor. An exemplary genetic circuit comprising such a kill switch is shown in FIGS. 1A and 14A. The repressor gene can be comprised within the interstitial region or elsewhere within the competent cell. In such configurations, the toxin gene and, optionally, the repressor of the toxin gene remain intact in the kill switch in the absence of target DNA, thereby maintaining the ability of the toxin gene to inhibit growth of the competent cell. In the presence of target DNA, however, the toxin gene and, optionally, the repressor of the toxin gene is/are excised from the DNA strand, thereby removing the ability of the toxin gene to inhibit growth of the cell and thereby permitting growth of the cell.

Figure 15A:
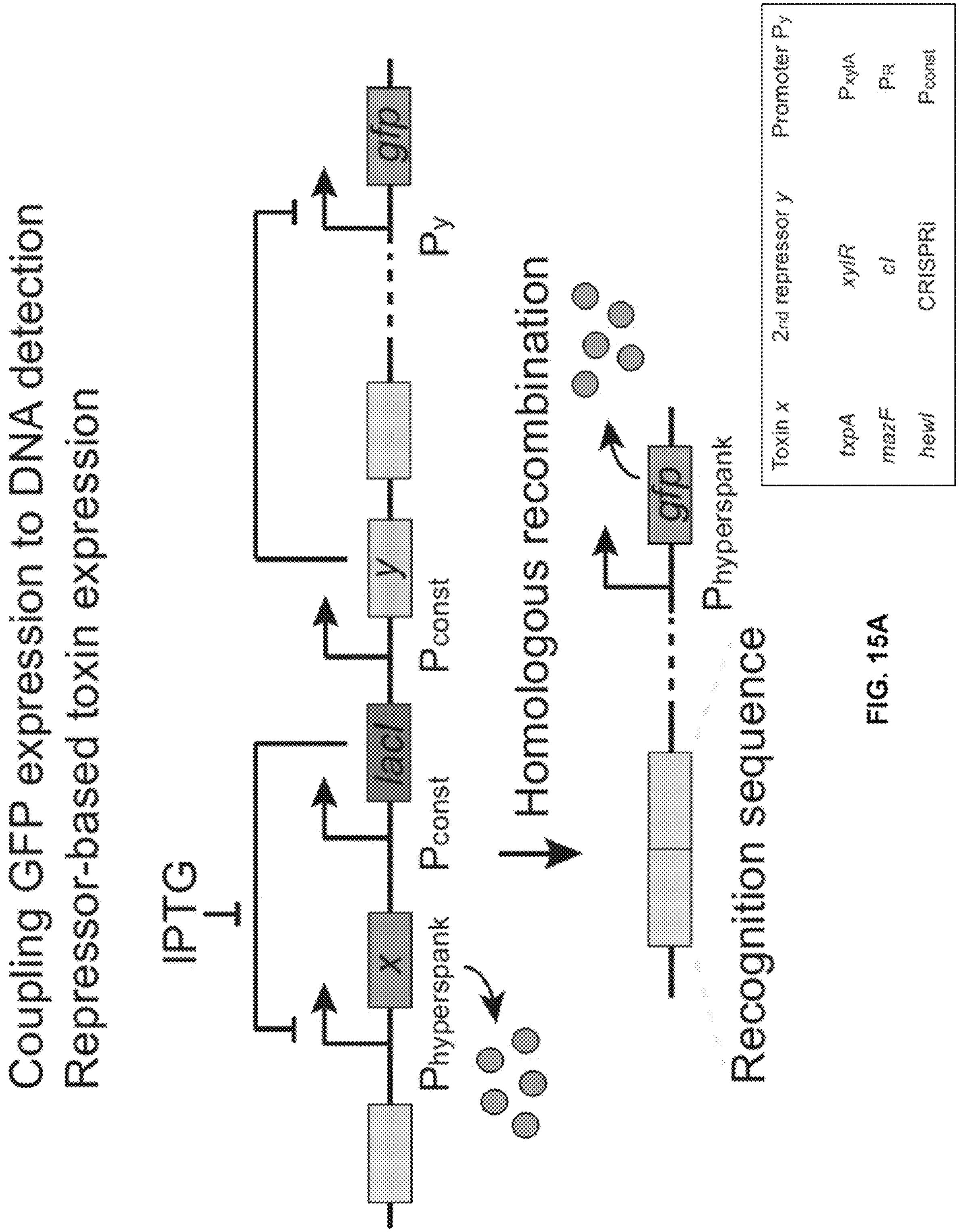
FIGS. 15A-15I. Additional exemplary synthetic genetic circuits coupling GFP expression and growth regulation to DNA detection.
Figure 15B:
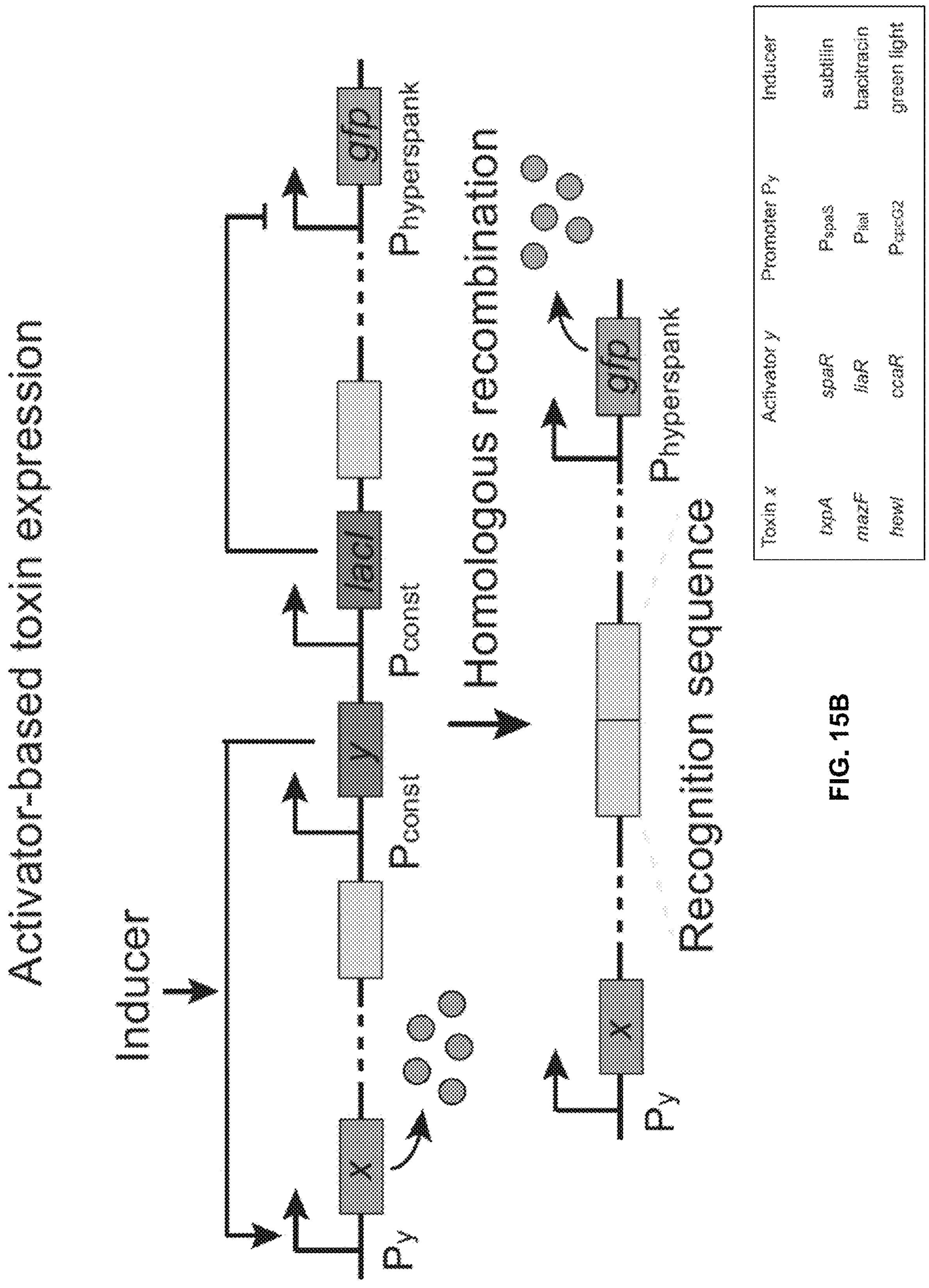
Figure 15C:
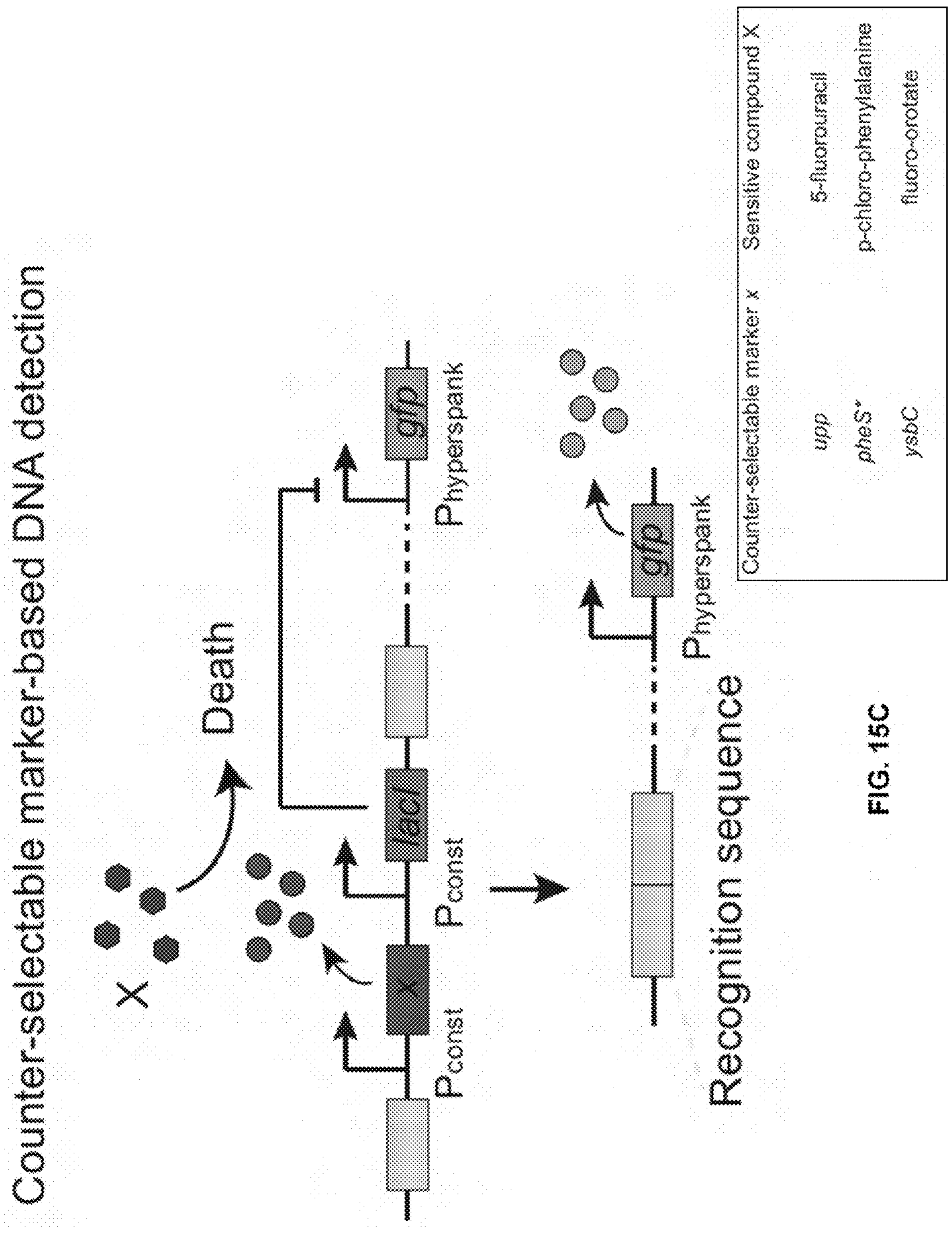
Figure 15D:
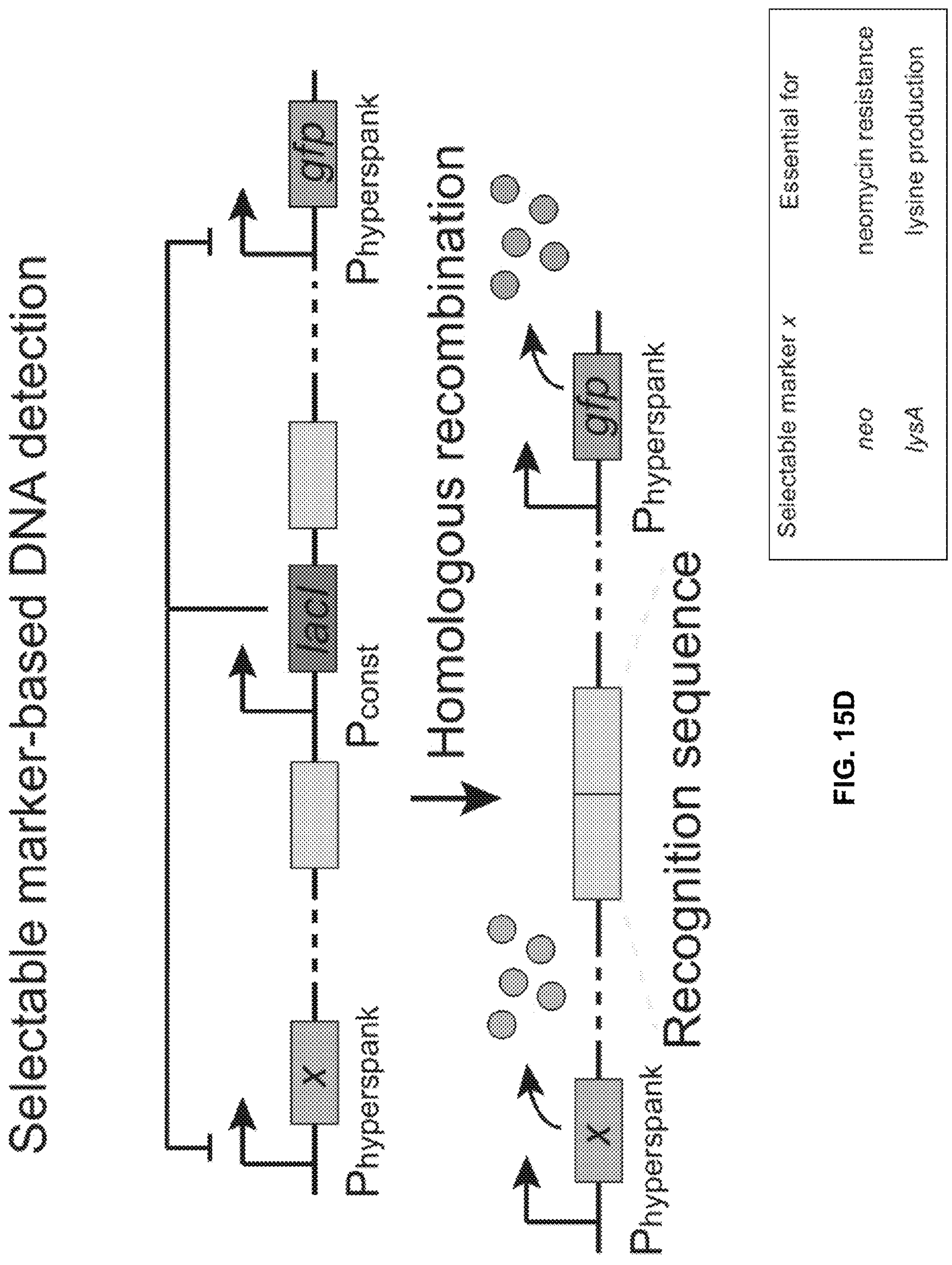
Figure 15E:
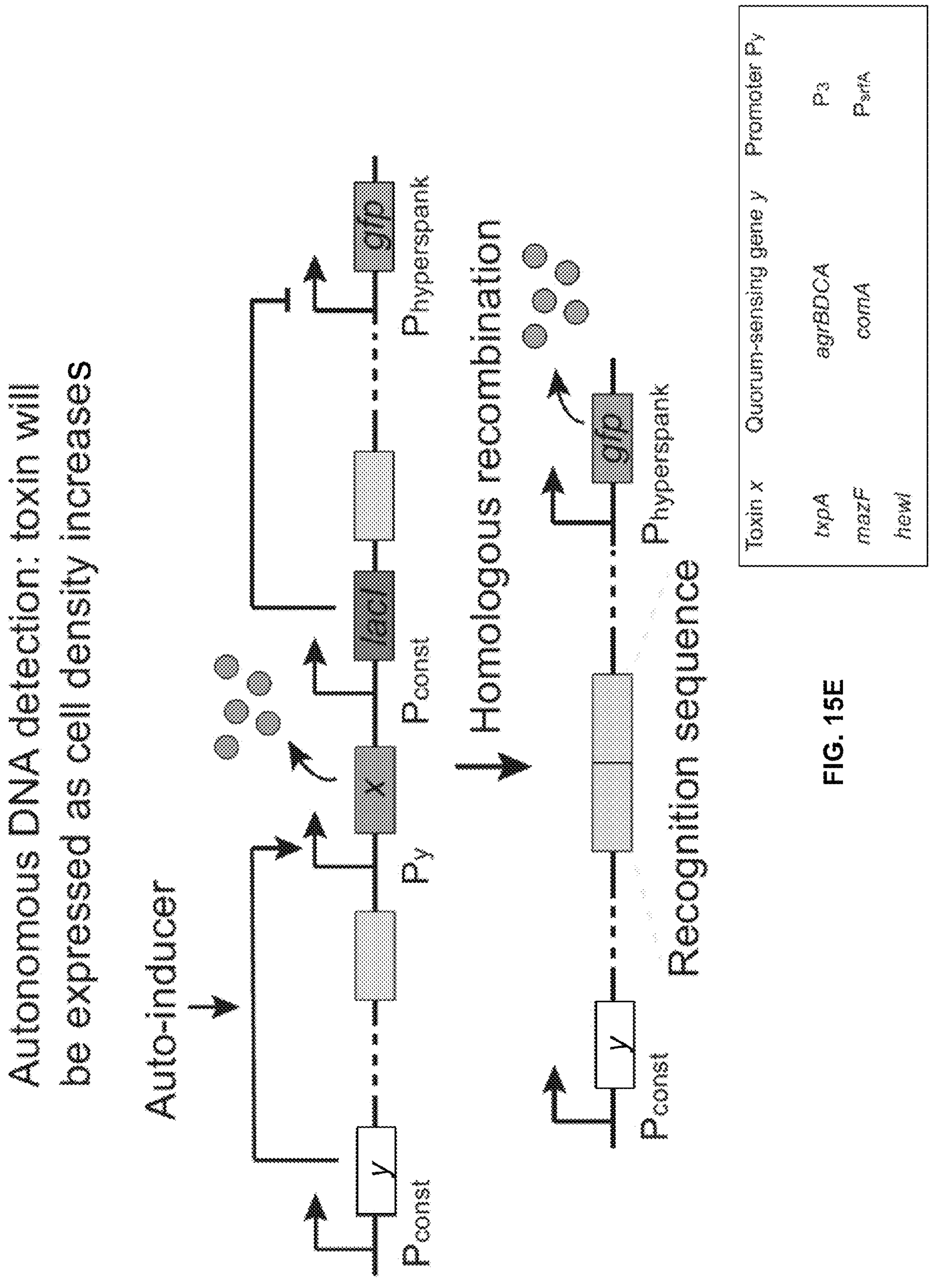

In some versions, the kill switch comprises a toxin gene and a positive regulator of the toxin gene, wherein one or both of the toxin gene and the positive regulator of the toxin gene is comprised within the interstitial region. An exemplary genetic circuit comprising such a kill switch is shown in FIGS. 15B and 15E. In such a configuration, the toxin gene and the positive regulator of the toxin gene remain intact in the kill switch in the absence of target DNA, thereby maintaining the ability of the toxin gene and the positive regulator of the toxin gene to inhibit growth of the competent cell. In the presence of target DNA, however, the toxin gene and/or the positive regulator of the toxin gene are/is excised from the DNA strand, thereby removing the ability of the toxin gene and the positive regulator of the toxin gene to inhibit growth of the cell and thereby permitting growth of the cell. In some versions, the positive regulator of the toxin gene comprises at least one of an activator gene that expresses an inducible activator of the toxin gene and a quorum-sensing gene that expresses regulatory receptor protein capable of activating the toxin gene.

In some versions, the kill switch comprises a counter-selectable marker gene comprised within the interstitial region. An exemplary genetic circuit comprising such a kill switch is shown in FIG. 15C. In such a configuration, the counter-selectable marker gene remains intact in the kill switch in the absence of target DNA, thereby maintaining the ability of the counter-selectable marker gene to inhibit growth of the competent cell. In the presence of target DNA, however, the counter-selectable marker gene is excised from the DNA strand, thereby removing the ability of the selectable marker gene to inhibit growth of the cell and thereby permitting growth of the cell.

In some versions, the kill switch comprises a selectable marker gene not comprised within the interstitial region of the DNA strand and a negative regulator of the selectable marker gene comprised within the interstitial region of the DNA strand. An exemplary genetic circuit with such a kill switch is shown in FIG. 15D. In such a configuration, the negative regulator of the selectable marker gene remains intact in the kill switch in the absence of target DNA, thereby maintaining the ability of the counter-selectable marker to inhibit growth of the competent cell. In the presence of target DNA, however, the negative regulator of the selectable marker gene is excised from the DNA strand, thereby removing the ability of the negative regulator of the selectable marker gene to inhibit growth of the cell and thereby permitting growth of the cell. In some versions, as shown in FIG. 15D, the negative regulator of the selectable marker gene is also the negative regulator of the reporter gene.

In some versions, the genetic circuit comprises a negative regulator that functions in both the reporter switch and the kill switch (FIGS. 15F-15II). The negative regulator is preferably inducible (shown is lacI, but others can be used). The reporter switch comprises a reporter gene (shown is gfp, but others can be used) with a promoter and a coding sequence that are not comprised within the interstitial region of the DNA strand, as well as the negative regulator, which negatively regulates the reporter gene.

Figure 15F:
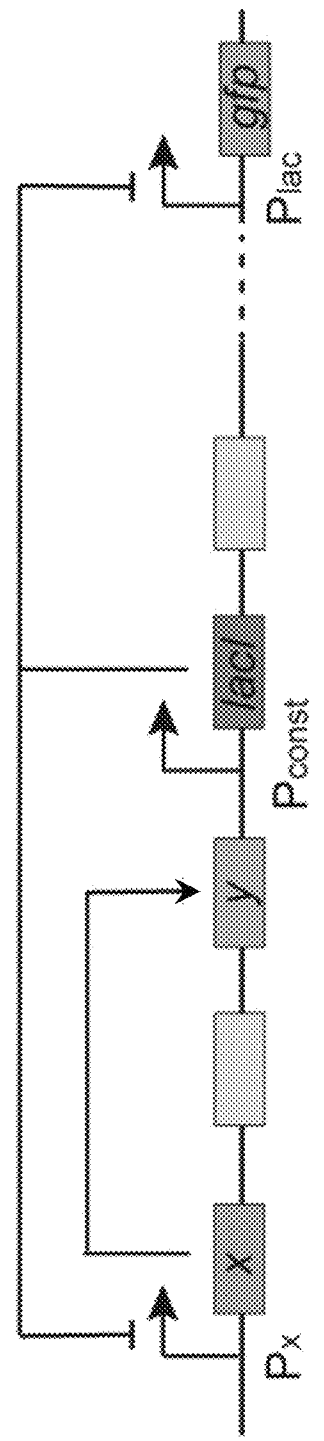
Figure 15G:
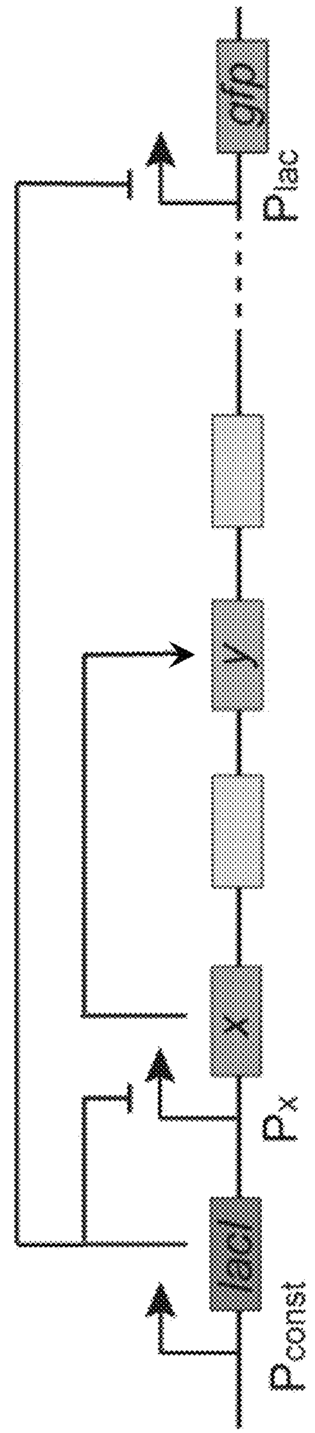
Figure 15H:
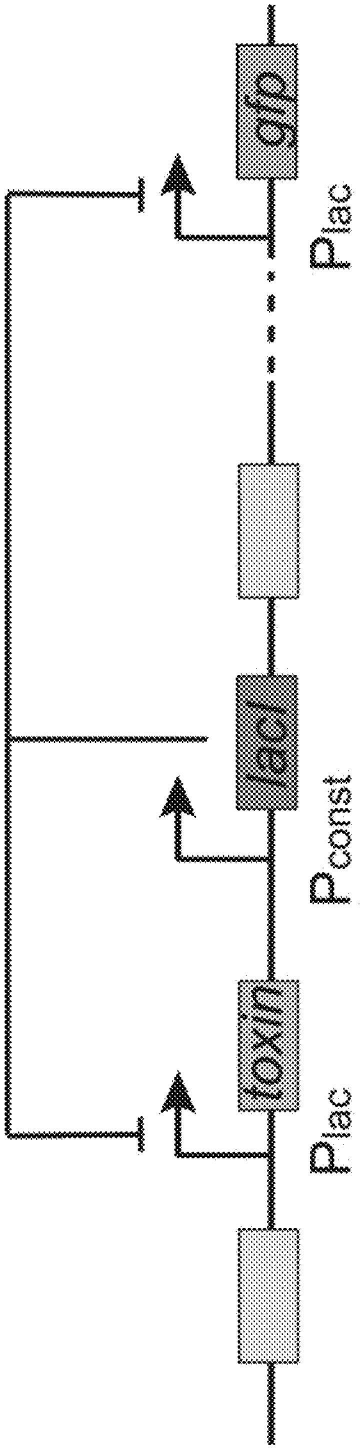
Figure 15I:
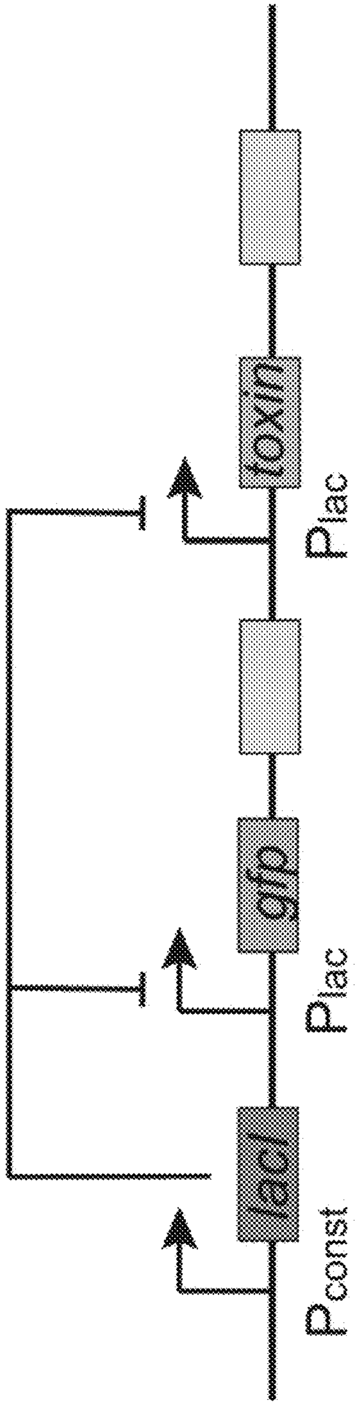

In FIGS. 15F and 15G, the kill switch comprises a growth inhibitor gene within the interstitial region, a positive regulator of the growth inhibitor gene (which can be inside or outside the interstitial region), and the negative regulator, which, in addition to negatively regulating the reporter gene, also negatively regulates the positive regulator of the growth inhibitor gene. In some versions, the negative regulator is comprised within the interstitial region (FIG. 15F). In other versions, the negative regulator is not comprised within the interstitial region (FIG. 15G). In the versions of FIGS. 15F and 15G, cells can be grown in the absence of inducer (such as IPTG) so that the positive regulator of the growth inhibitor gene is inhibited. After exposing to target DNA (or target cells), inducer can be added to stimulate expression of the positive regulator of the growth inhibitor gene and the reporter gene. If the growth inhibitor gene is present, the cells will die. If the growth inhibitor gene is not present, the cells will grow and the reporter will be expressed. In FIGS. 15H and 151, the kill switch in comprises a growth inhibitor gene (toxin as shown, but others can be used) within the interstitial region and the negative regulator, which, in addition to negatively regulating the reporter gene, also negatively regulates the growth inhibitor gene. In some versions, the first negative regulator is comprised within the interstitial region (FIG. 15H). In other versions, the first negative regulator is not comprised within the interstitial region (FIG. 15I). In the versions of FIGS. 15H and 15I, cells can be grown in the absence of inducer (such as IPTG) so that the growth inhibitor gene is inhibited. After exposing to target DNA (or target cells), inducer can be added to stimulate expression of the growth inhibitor gene and the reporter gene. If the growth inhibitor gene is present, the cells will die. If the growth inhibitor gene is not present, the cells will grow and the reporter will be expressed.

The target DNA detected with the DNA sensors of the invention can comprise any sequence. In some versions, the target DNA is native DNA. "Native DNA" as used herein is DNA that consists of native sequence, wherein "native sequence" refers to a natural DNA sequence (a sequence found in nature). In some versions, the target DNA is recombinant DNA. "Recombinant DNA" as used herein is DNA that comprises a recombinant sequence, wherein "recombinant sequence" refers to non-natural sequence (a sequence not found in nature.) In some versions, the portion(s) of the target DNA homologous to the pair of homology arms (referred to herein as the first and second portions of the target DNA) consists of native sequence. In some versions, the portion(s) of the target DNA homologous to the pair of homology arms (referred to herein as the first and second portions of the target DNA) comprises recombinant sequence. In some versions, the target DNA is cellular DNA. "Cellular DNA" refers to DNA presently or formerly comprised within a cell. Cellular DNA can comprise genomic DNA, chromosomal DNA, plasmid DNA, etc. In some versions, the target DNA is non-isolated cellular DNA. "Non-isolated cellular DNA" refers to cellular DNA that is not isolated, purified, released, or removed (e.g., by cell lysis) from the cell using chemical or physical treatment. Free cellular DNA present in a culture medium that has not been isolated, purified, released, or removed (e.g., by cell lysis) from the cell using chemical or physical treatment, for example, constitutes non-isolated cellular DNA. In some versions, the non-isolated cellular DNA is from eukaryotic cells. In some versions, the non-isolated DNA is from mammalian cells (e.g., cancer cells). In some versions, the non-isolated cellular DNA is from prokaryotic cells. In some versions, the non-isolated cellular DNA is from bacterial cells (referred to herein as non-isolated bacterial DNA).

The target DNA can be DNA from any target organism or target cell. Exemplary organisms comprise bacteria, viruses, fungi, and animals such as humans. For the purposes herein, viruses are considered to be organisms. "Target organism" and "target cell" refer to an organism or cell, respectively, in which target DNA is comprised or from which target DNA is derived.

Exemplary target bacteria include members of the genus *Bacillus*, such as *Bacillus anthracis* and *Bacillus cereus*; members of the genus *Bordetella*, such as *Bordetella pertussis*; members of the genus *Borrelia*, such as *Borrelia burgdorferi*; members of the genus *Brucella*, such as *Brucella abortus, Brucella canis, Brucella melitensis*, and *Brucella suis*; members of the genus *Campylobacter*, such as *Campylobacter jejuni*; members of the genus *Chlamydia*, such as *Chlamydia pneumoniae, Chlamydia trachomatis*, and *Chlamydophila psittaci*; members of the genus *Clostridium*, such as *Clostridium botulinum, Clostridium difficile, Clostridium perfringens*, and *Clostridium tetani*; members of the genus *Corynebacterium*, such as *Corynebacterium diphtheriae*; members of the genus *Clostridioides*, such as *Clostridioides difficile* and *Clostridioides mangenotii*; members of the genus *Enterococcus*, such as *Enterococcus faecalis* and *Enterococcus faecium*; members of the genus *Escherichia*, such as *Escherichia coli*; members of the genus *Francisella*, such as *Francisella tularensis*; members of the genus *Haemophilus*, such as *Haemophilus influenzae*; members of the genus *Helicobacter*, such as *Helicobacter pylori*; members of the genus *Legionella*, such as *Legionella pneumophila*; members of the genus Leptospira, such as *Leptospira interrogans*; members of the genus *Listeria*, such as *Listeria monocytogenes*; members of the genus *Mycobacterium*, such as *Mycobacterium leprae, Mycobacterium tuberculosis*, and *Mycobacterium ulcerans*; members of the genus *Mycoplasma*, such as *Mycoplasma pneumoniae*; members of the genus *Neisseria*, such as *Neisseria gonorrhoeae* and *Neisseria meningitidis*; members of the genus *Pseudomonas*, such as *Pseudomonas aeruginosa*; members of the genus *Rickettsia*, such as *Rickettsia rickettsii*; members of the genus *Salmonella*, such as *Salmonella typhi* and *Salmonella typhimurium*; members of the genus *Shigella*, such as *Shigella sonnei*; members of the genus *Staphylococcus*, such as *Staphylococcus aureus, Staphylococcus epidermidis*, and *Staphylococcus saprophyticus*; members of the genus *Streptococcus*, such as *Streptococcus agalactiae, Streptococcus pneumoniae*, and *Streptococcus pyogenes*; members of the genus *Treponema*, such as *Treponema pallidum*; members of the genus *Vibrio*, such as *Vibrio cholerae*; members of the genus *Yersinia*, such as *Yersinia pestis, Yersinia enterocolitica*, and *Yersinia pseudotuberculosis*, among others.

Exemplary target viruses include viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the family hepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as severe acute respiratory syndrome (SARS) viruses, including SARS-CoV-2; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Exemplary target fungi include fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause *pneumocystis* pneumonia; and fungi of the genus *Sporothrix*, such as *Sporothrix schenckii*, which cause sporotrichosis.

In some versions, the target DNA sequence is an antibiotic resistance gene or a regulator gene, wherein homologous recombination corrects the point mutation in the kill switch or the reporter to thereby activate the kill switch or reporter.

The DNA sensors of the invention can be comprised in compositions. In some versions, the compositions comprise one or more DNA sensors in a culture medium. The culture medium is preferably capable of supporting growth of the DNA sensor under certain conditions. Such conditions preferably include the presence of target DNA. In some versions, the compositions comprise one or more DNA sensors in combination with a target DNA. In some versions, the compositions comprise two or more DNA sensors, such as three or more, four or more, five or more, or six or more DNA sensors. The two or more DNA sensors can be configured to detect different target DNA sequences, such as from different target organisms or target cells, and express different reporters. In one exemplary configuration, the pairs of homology arms in the two or more cell-based sensors are each homologous to different target DNA sequences, and the reporter genes in the two or more cell-based DNA sensors express reporters that are each detectably different from each other. In some versions, the detectably different reporters comprise fluorescent reporters that emit fluorescence at different wavelengths. The compositions comprising the two or more DNA sensors can be used in multiplex detection methods.

The DNA sensors of the invention can be used in methods of detecting target DNA. The methods can comprise culturing the DNA sensor in a culture medium comprising the target DNA for a time effective to transform the DNA sensor with the target DNA and then detecting the transformed DNA sensor. "Transformation" (and grammatical variants) as used herein refers to the uptake of DNA into a cell. The genetic circuits of the transformed DNA sensors can then undergo homologous recombination with the transformed DNA, thereby excising the interstitial region from the DNA strand and altering the reporter switch (if present), the kill switch (if present), or both (if present). In some versions, the DNA sensor comprises a reporter switch, and detection of the target DNA occurs by detecting growth of the DNA sensor. In some versions, the DNA sensor comprises a kill switch, and detection of the target DNA occurs by detecting a reporter expressed from the reporter gene. In some versions, the DNA sensor comprises a reporter switch and a kill switch, and detection of the target DNA occurs by detecting a reporter expressed from the reporter gene and/or growth of the DNA sensor. It has been found that including both a reporter switch and a kill switch in a DNA sensor of the invention can enhance detection by amplifying the signal to noise (background) ratio of the reporter with respect to including a reporter switch alone.

It has been surprisingly found that target cells such as bacteria release sufficient DNA during culture to transform the DNA sensors of the invention and undergo homologous recombination for detection thereof without isolating, purifying, releasing, or removing (e.g., by cell lysis) target DNA from the target cell using chemical or physical treatment. Accordingly, some methods of the invention are directed to detecting a target cell comprising target DNA. Such methods can comprise culturing the DNA sensor in a culture medium with the target cell for a time effective to transform the DNA sensor with the target DNA and then detecting the transformed DNA sensor. In some methods, the culturing is performed without lysing the target cell. In some methods, the method is performed without isolating, purifying, releasing, or removing (e.g., by cell lysis) the target DNA from the target cell using chemical or physical treatment. In some methods, the target DNA is non-isolated cellular DNA. In some methods the target cell comprises a bacterium. In some methods, the target DNA is non-isolated bacterial DNA. In some methods, the cell-based DNA sensor comprises two or more cell-based DNA sensors, wherein: the pairs of homology arms the two or more cell-based sensors are each homologous to different target DNA sequences from different target cells; each of the two or more cell-based DNA sensors comprises the reporter switch; and the reporter genes in the two or more cell-based DNA sensors express reporters that are each detectably different from each other. In some methods, the two or more cell-based sensors comprise three or more cell-based sensors.

Aspects pertaining to homologous recombination such as homology length and sequence identity are known in the art.[66,67,68,69]

Unless the context indicates otherwise, any gene described herein as "expressing" or being one that "expresses" a particular gene product can constitutively express the gene product (e.g., via a constitutive promoter) or inducibly express the gene product (e.g., via an inducible promoter or a promoter sensitive to a regulatory protein, such as a repressor or an activator). The unmodified term "expresses" therefore encompasses but does not necessarily require constitutive expression. The phrases "expresses" and "configured to express" are used interchangeably herein.

Terms used herein pertaining to genetic manipulation are defined as follows.

Endogenous: As used herein with reference to a polynucleotide molecule and a particular cell, "endogenous" refers to a polynucleotide sequence or polypeptide that is in the cell and was not introduced into the cell using recombinant engineering techniques. For example, an endogenous gene is a gene that was present in a cell when the cell was originally isolated from nature.

Exogenous: As used herein with reference to a polynucleotide molecule or polypeptide in a particular cell, "exogenous" refers to any polynucleotide molecule or polypeptide that does not originate from that particular cell as found in nature. Thus, a non-naturally-occurring polynucleotide molecule or protein is considered to be exogenous to a cell once introduced into the cell. A polynucleotide molecule or protein that is naturally occurring also can be exogenous to a particular cell. For example, an entire coding sequence isolated from cell X is an exogenous polynucleotide with respect to cell Y once that coding sequence is introduced into cell Y. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Isolated: Except as otherwise defined herein, an "isolated" biological component (such as a polynucleotide molecule, polypeptide, or cell) has been substantially separated or purified away from other biological components in which the component naturally occurs, such as other chromosomal and extrachromosomal DNA and RNA and proteins. Polynucleotide molecules and polypeptides that have been "isolated" include polynucleotide molecules and polypeptides purified by standard purification methods. The term also includes polynucleotide molecules and polypeptides prepared by recombinant expression in a cell as well as chemically synthesized polynucleotide molecules and polypeptides.

Polynucleotide: Encompasses both RNA and DNA molecules including, without limitation, cDNA, genomic DNA, and mRNA. Polynucleotides also include synthetic polynucleotide molecules, such as those that are chemically synthesized or recombinantly produced. The polynucleotide can be double-stranded or single-stranded. Where single-stranded, the polynucleotide molecule can be the sense strand, the antisense strand, or both. In addition, the polynucleotide can be circular or linear.

Operably linked: A first polynucleotide sequence is operably linked with a second polynucleotide sequence when the first polynucleotide sequence is placed in a functional relationship with the second polynucleotide sequence. For instance, a promoter is operably linked to a coding sequence if the promoter affects the transcription or expression of the coding sequence. An origin of replication is operably linked to a coding sequence if the origin of replication controls the replication or copy number of the polynucleotide in the cell. Operably linked polynucleotides may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Recombinant cell: A cell that comprises a recombinant polynucleotide.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

A coding sequence can be operably linked to an appropriate expression control sequence (promoters, enhancers, and the like) to direct synthesis of the encoded gene product. Such promoters can be derived from microbial or viral sources, including CMV and SV40. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology,* 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus; Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In:

*Molecular Cloning: A Laboratory Manual,* $3^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Genet.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) PNAS (USA) 79:6971; Silver et al. (1984) *PNAS* (USA) 81:5951); and the IgG promoter (Orlandi et al. (1989) *PNAS* (USA) 86:3833).

Coding sequences can be operably linked to an inducible promoter. Inducible promoters are those wherein addition of an effector affects expression. Suitable effectors include proteins, metabolites, chemicals, or culture conditions capable of affecting expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-1 promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

In some versions, the promoter is a constitutive promoter. Suitable constitutive promoters are known in the art and include constitutive adenovirus major late promoter, a constitutive MPSV promoter, and a constitutive CMV promoter.

The elements of the genetic circuits of the invention can be integrated in the competent cell's chromosome or an extra-chromosomal DNA, such as a plasmid, or a combination thereof.

Polynucleotides encoding enzymes desired to be expressed in a cell may be codon-optimized for that particular type of cell. Codon optimization can be performed for any polynucleotide by "OPTIMUMGENE"-brand gene design system by GenScript (Piscataway, NJ).

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

Examples

Programming Bacteria for Multiplexed DNA Detection

SUMMARY

DNA is a universal and programmable signal of living organisms. Here we developed cell-based DNA sensors by engineering the naturally competent bacterium *Bacillus subtilis* (*B. subtilis*) to detect specific DNA sequences in the environment. The DNA sensor strains can identify diverse bacterial species including major human pathogens with high specificity and sensitivity. Multiplexed detection of genomic DNA from different species in complex samples can be achieved by coupling the sensing mechanism to orthogonal fluorescent reporters. We also demonstrate that the DNA sensors can detect the presence of species in the complex samples without requiring DNA extraction. The modularity of the living cell-based DNA sensing mechanism and simple detection procedure enables programmable DNA sensing for broad applications.

INTRODUCTION

Next-generation engineered bacteria hold tremendous promise for a wide range of applications in human health, environment and agriculture by sensing key environmental signals, performing computation on these signals to regulate a response that modulates specific environmental parameters[1]. Developing specific and selective sensors of key environmental signals is a critical feature of next-generation engineered bacteria. For example, bacteria have been engineered to detect physical and chemical signals such as light, ultrasound, and quorum-sensing molecules[2-4]. These signals can be exploited to control the collective growth or gene expression of the bacterial population or mediate interactions between constituent community members[4-6]. In addition, we can exploit their sensing ability to achieve real-time monitoring of natural environments. For example, synthetic genetic circuits have been designed in *Escherichia coli* (*E. coli*) to sense signals produced by pathogens and use this information to regulate the production of antimicrobials that inhibit the target pathogen[7,8]. However, there are limited well-characterized and orthogonal signals that can be exploited to sense different bacterial species in a microbial community[9,10].

DNA provides the blueprint for living organisms and is prevalent in natural environments[11]. Therefore, extracellular DNA (eDNA) could be exploited as a biomarker for identifying different species. Naturally competent bacteria have the ability to take up DNA from the environment and integrate imported sequences onto the genome based on sequence homology requirements. Horizontal gene transfer (HGT) via natural transformation has been shown to have a variety of benefits such as nutrient utilization, DNA repair, or acquisition of genes[12]. Since homologous recombination of imported DNA requires sequences of sufficient length and homology[13], natural transformation could be exploited to build a selective cell-based DNA sensor.

We constructed a living cell-based DNA sensor by engineering the naturally competent bacterium *B. subtilis*. This circuit controls *B. subtilis* growth and fluorescence reporter genes in response to specific input DNA sequences. We demonstrate that the cell-based DNA sensor is sensitive and highly specific to species harboring the target DNA sequence. In addition, we demonstrate that our cell-based DNA sensor can perform multiplexed DNA detection in complex samples. The cell-based DNA sensors can detect DNA released from pre-treated donor cells (i.e. crude samples). Our detailed characterization of the cell-based DNA sensors in vitro provides a foundation for future in vitro DNA detection and in situ sense-and-respond DNA applications.

Results

Construction of a Living DNA Sensor Strain

To build the living cell-based DNA sensor, we exploited the natural competence ability of the well-characterized soil bacterium *B. subtilis*[14]. The natural competence ability of *B. subtilis* enables uptake of environmental DNA and integration of specific sequences with sufficient homology into genome via homologous recombination[15]. The efficiency of homologous recombination depends stringently on the sequence percent identity and length[13,16], which can be exploited to build a highly specific DNA sensor.

To detect eDNA sequences in a programmable fashion, we constructed a synthetic genetic circuit in *B. subtilis* that implements a growth selection function based on the presence of target DNA sequence in the environment. The circuit consists of a xylose-inducible master regulator of competence comK[17] and IPTG-inducible toxin-antitoxin system txpA-ratA[18] and GFP regulated by the repressor LacI (FIGS. 1A and 5A-5C). The target sequences were introduced to the flanking regions (upstream and downstream) of txpA-ratA and lacI and referred to as landing pads for homologous recombination.

In the presence of xylose, ComK activates competence genes for DNA uptake and homologous recombination (FIG. 1A). Bistability and stochastic processes in the regulation of natural competence can yield a sub-population that can be transformed with extracellular DNA[19]. This naturally competent sub-population forms competence pili which bind to double stranded DNA outside the cell. The DNA is cleaved into single-stranded DNA (ssDNA) outside the cell membrane, and transported into the cell[12]. Inside the cell, RecA binds the ssDNA sequences and searches the *B. subtilis* genome for a region with sufficient homology. If the target DNA sequence is present, homologous recombination removes the toxin-antitoxin txpA-ratA and repressor lac. In the presence of the chemical inducer Isopropyl β-D-1-thiogalactopyranoside (IPTG), cell growth and GFP expression is enabled in the transformed sub-population. Growth of the non-transformed subpopulation is inhibited by the activity of TxpA, which blocks cell wall synthesis[18] (FIG. 1A).

We constructed a sensor for *E. coli* (EC sensor) by introducing the xdhABC operon onto the *B. subtilis* genome (landing pad region), which encodes genes for purine catabolism[20]. The xdhABC operon is a representative sequence that can detect a wide range of *E. coli* strains. This sequence is highly conserved such that 99% of 5000 *E. coli* genomes in the NCBI database contain this sequence with >95% coverage (the degree of alignment of the query sequence with a reference sequence) and >95% identity similarity (the percentage of bases that are identical to the target sequence within the aligned region).

Figure 1C:
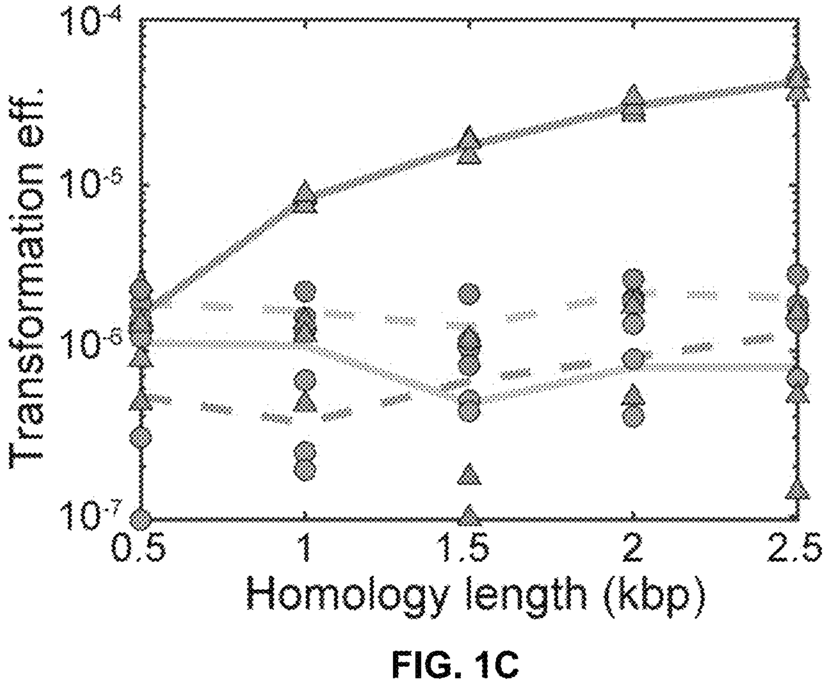
Figure 6A:
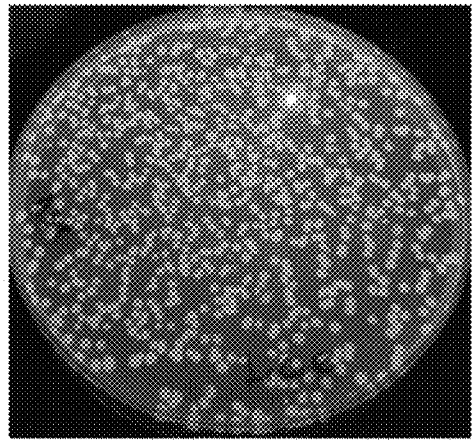
FIGS. 6A-6F. Sequencing of transformed *E. coli* sensor and escape mutants. Representative fluorescence images of colonies of *E. coli* DNA sensor on selective agar plate after the transformation of (FIG. 6A) 100 ng/mL purified *E. coli* gDNA or (FIG. 6B) no DNA. DNA of the circuit in *B. subtilis* genome was PCR amplified from different colonies and sequenced to confirm the homologous recombination for the transformed sensor (N=12) or mutations for the escape mutants (N=12).
Figure 6B:
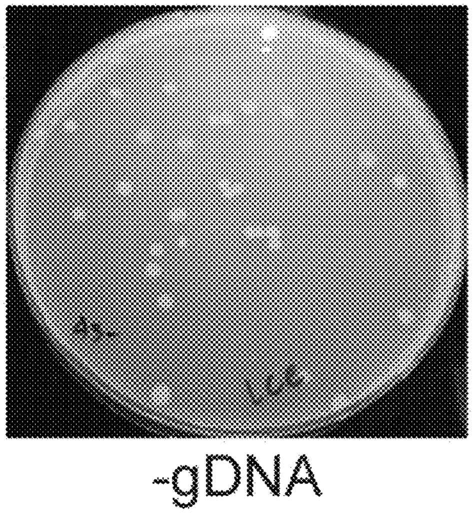
Figure 6C:
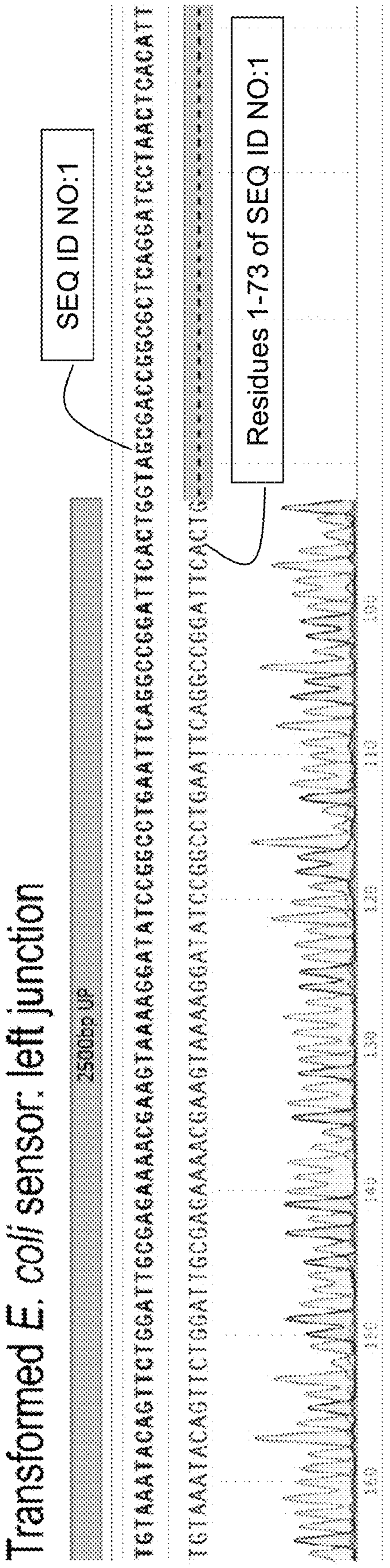
Figure 6D:
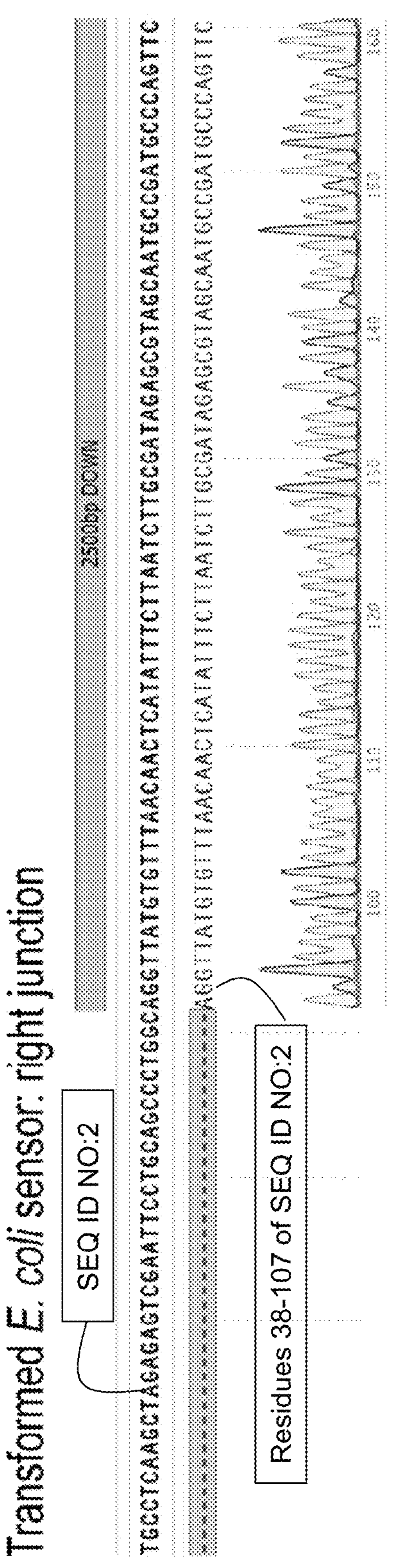
Figure 6E:
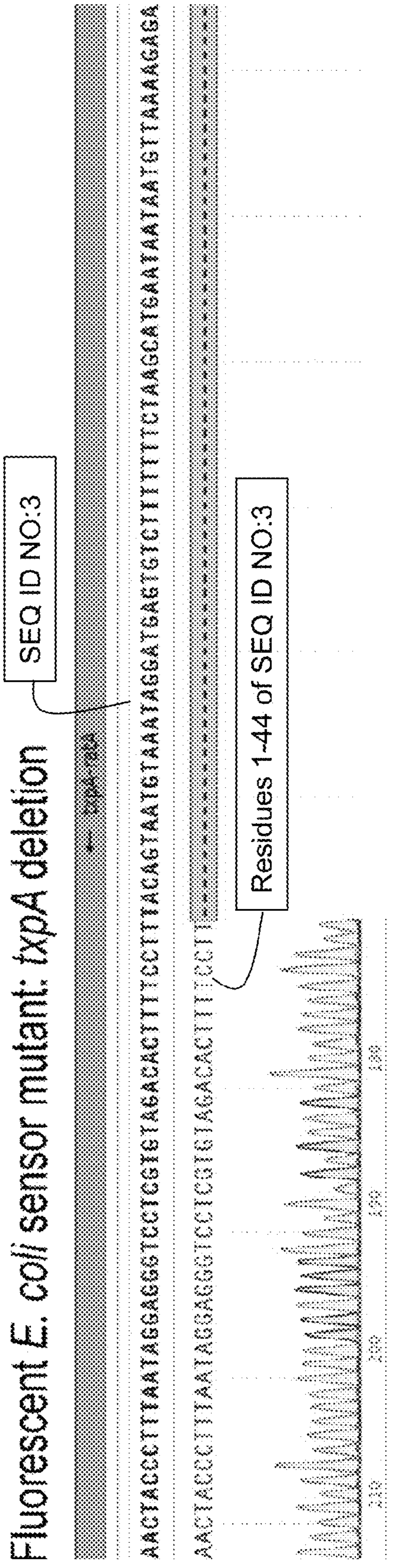
Figure 6F:
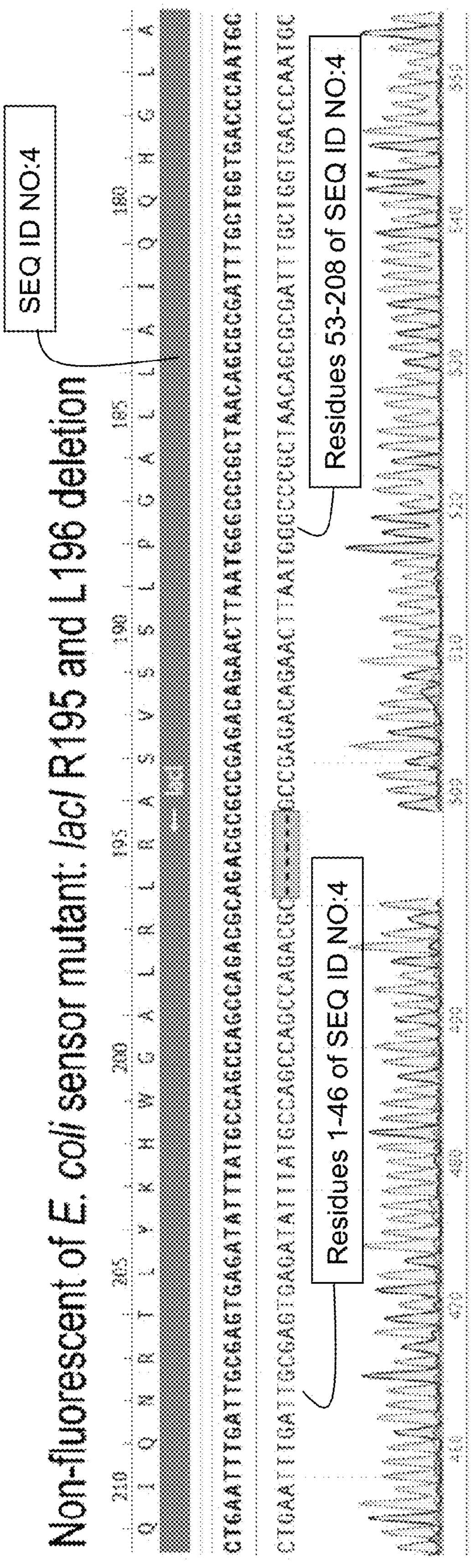

To characterize the homology length needed for robust DNA sensing, we varied the homology length of the xdhABC operon in each landing pad (0.5 to 2.5 kb). We performed time-series measurements of transformation efficiency (number of colonies for transformed *B. subtilis* cells divided by the number total *B. subtilis* colonies) with 100 ng/mL *E. coli* genomic DNA (gDNA). The transformation efficiency is defined as the ratio of the number of transformed *B. subtilis* to the total number of *B. subtilis* based on colony forming units (CFU). Transformation efficiency plateaued at approximately 10 hr and the colonies expressed GFP (FIG. 1*i*). In addition, transformation efficiency increased with homology length at 10 hr (FIG. 1C). A homology length of 1 kb or greater was required to robustly sense the target sequence over the background frequency of escape mutants ($10^{-7}$-$10^{-6}$ frequency) that displayed heterogenous GFP expression (FIGS. 6A and 6B). To achieve high performance of the DNA sensor (>$10^2$ increase in transformation efficiency above background), we used a landing pad homology length of 2.5 kb (transformation efficiency of 10-5-10-4). In the transformed sub-population, homologous recombination was confirmed by sequencing to occur at the expected location with the elimination of txpA-ratA and lac (FIGS. 6C and 6D). The moderate number of escape mutants that displayed growth in the absence of gDNA had mutations in txpA or lacI, which reduced the growth inhibitory activity of TxpA (FIGS. 6E and 6F). In sum, the synthetic genetic circuit enabled *B. subtilis* to sense specific DNA sequences present in the environment.

Building Living DNA Sensors to Sense Human Pathogens

Figure 5A:
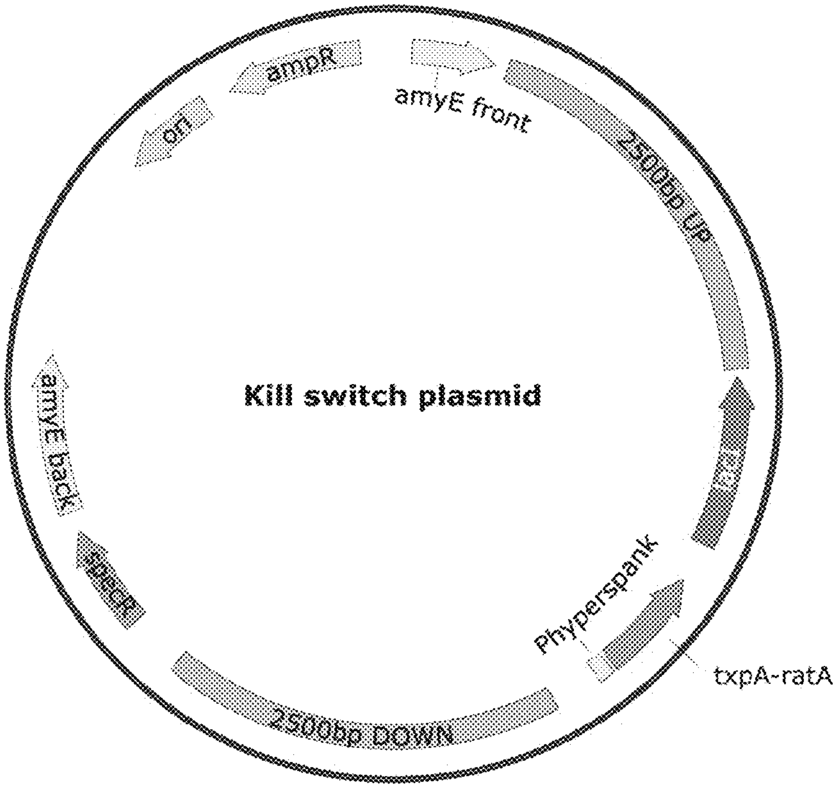
FIGS. 5A-5C. Plasmid maps for the construction of DNA-sensing *B. subtilis*.
Figure 5B:
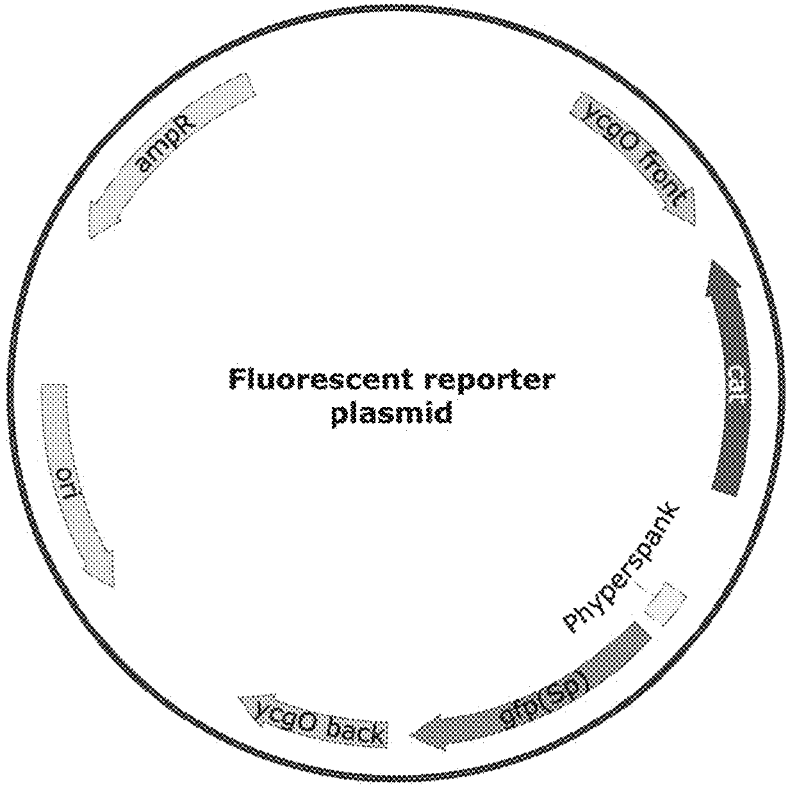
Figure 5C:
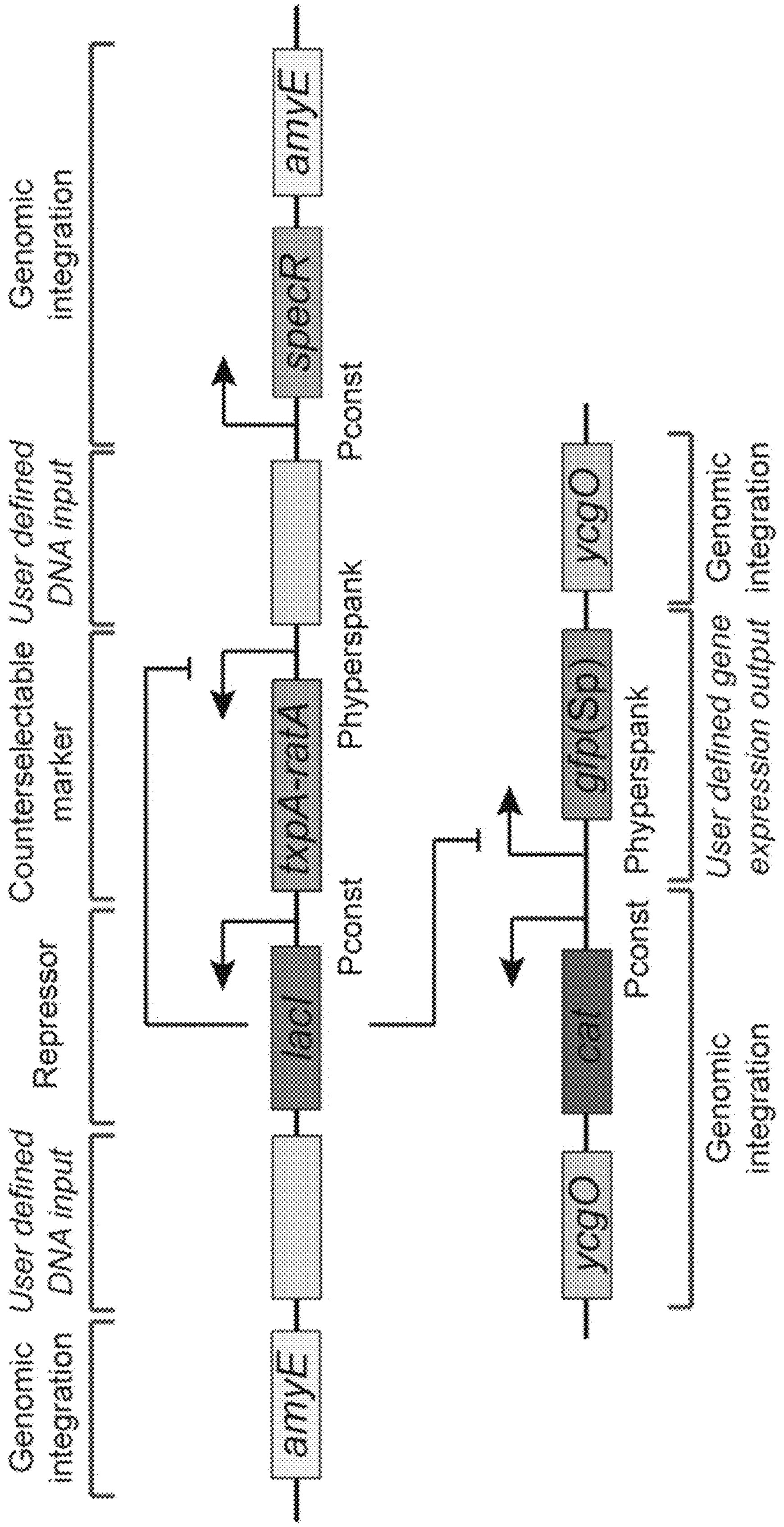

Exploiting the modularity of the DNA sensing circuit, we replaced the landing pad region with specific sequences targeting different bacterial strains (FIG. 5C). To this end, we constructed DNA sensors to detect sequences harbored in human intestinal pathogens *Salmonella typhimurium*[21] (*S. typhimurium*), *Clostridium difficile*[22] (*C. difficile*), or the skin pathogen *Staphylococcus aureus*[23] (*S. aureus*). We selected two 2.5 kb sequences in the pathogenicity island sipBCDA of *S. typhimurium* (ST sensor), the heme biosynthesis pathway hemEH in *S. aureus* (SA sensor), and the phenylalanyl-tRNA synthetase pheST in *C. difficile* (CD sensor)[24-26].

Figure 7A:
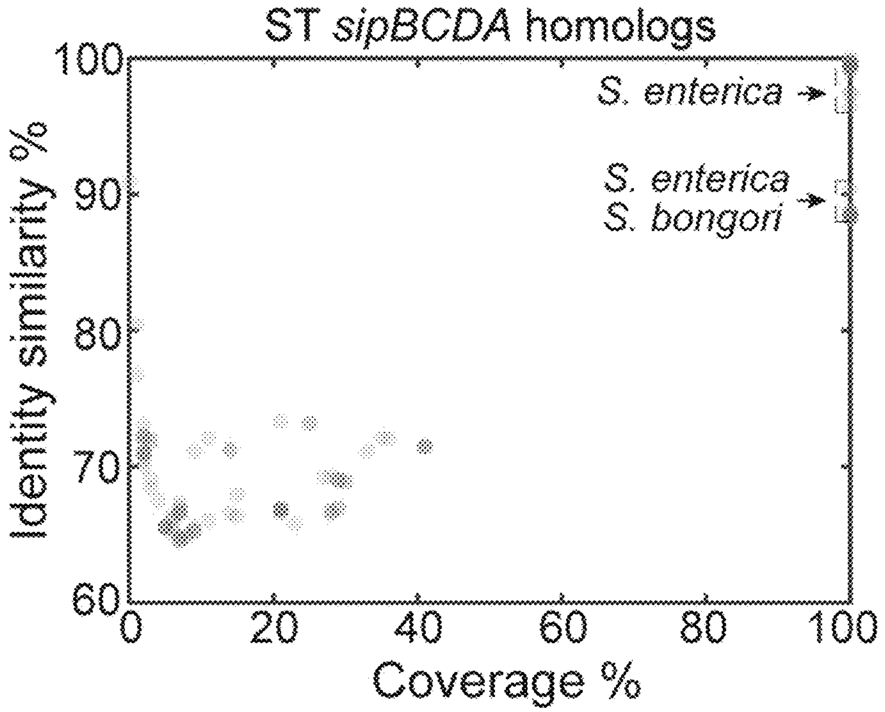
FIGS. 7A and 7B. Nucleotide BLAST search of homology sequences in EC sensor and ST sensor.
Figure 7B:
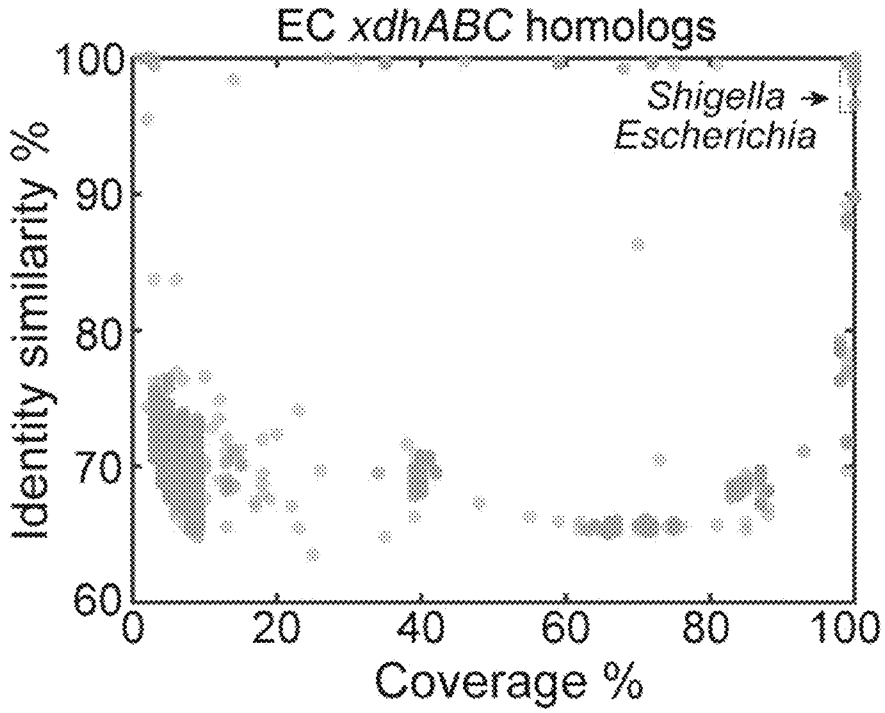
Figure 8A:
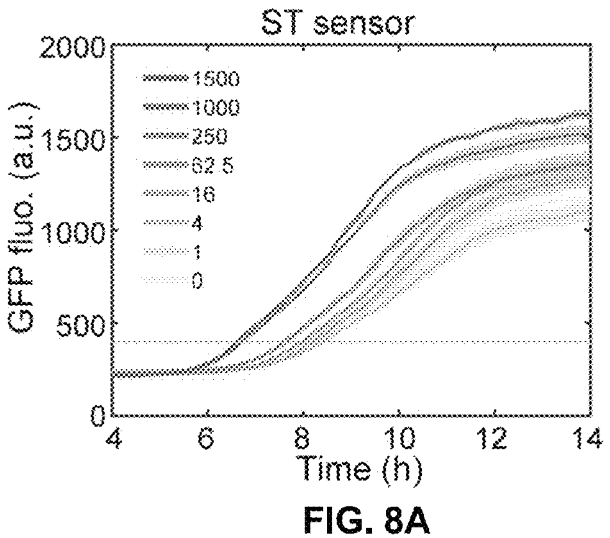
FIGS. 8A-8C. Time-series measurements of GFP expression of ST, SA, CD sensors in liquid medium after transformation. Time-series measurements of GFP expression of (FIG. 8A) ST sensor, (FIG. 8B) SA sensor, and (FIG. 8C) CD sensor in liquid medium after the transformation of varying target gDNA concentrations (ng/mL). A threshold of GFP 400 was used to determine the detection time for each gDNA concentration. Line is the average of four technical replicates and the shaded region represents one standard deviation from the average.
Figure 8B:
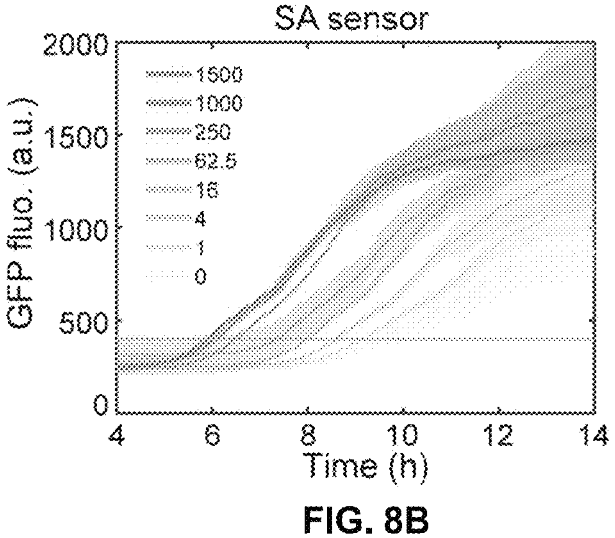
Figure 8C:
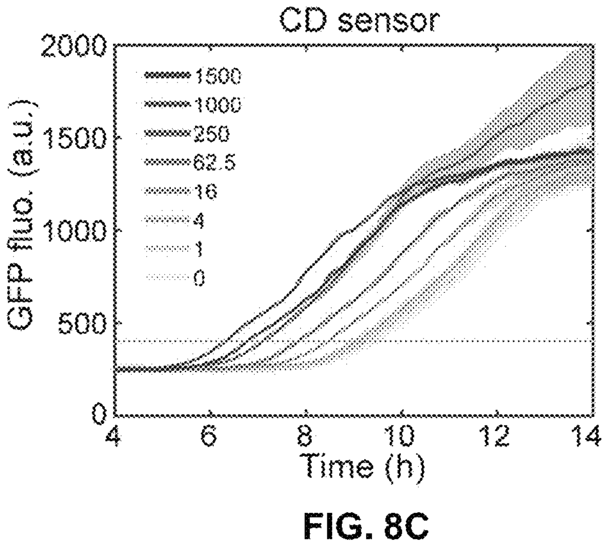
Figure 9A:
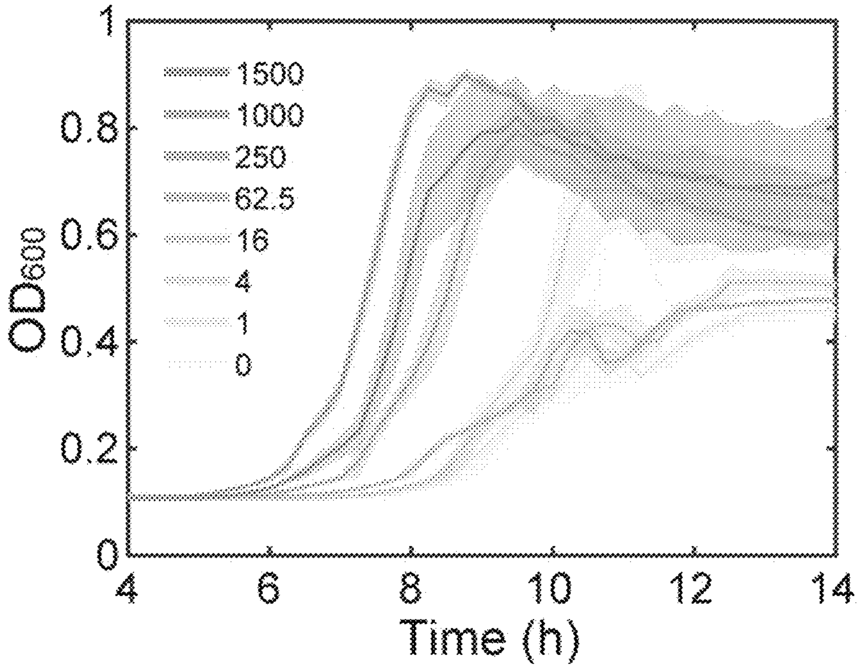
FIGS. 9A-9D. Time-series OD measurements of DNA sensors in liquid medium after transformation. Time-series measurements of OD600 absorbance of (FIG. 9A) EC sensor, (FIG. 9B) ST sensor, (FIG. 9C) SA sensor, and (FIG. 9D) CD sensor in liquid medium after the transformation of varying target gDNA concentrations (ng/mL). Line is the average of four technical replicates and the shaded region represents one standard deviation from the average. Cell growth correlated with DNA concentration during transformation.
Figure 9B:
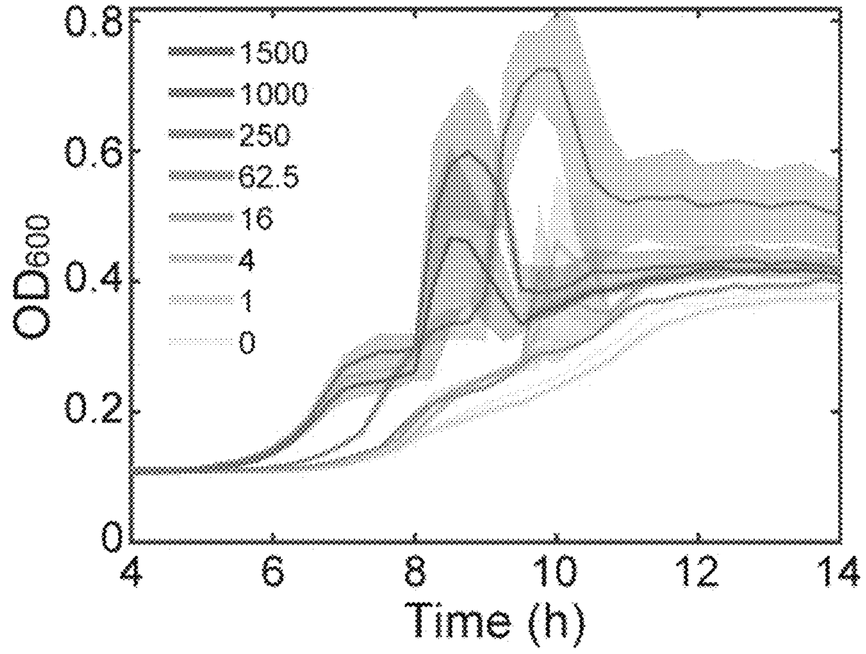
Figure 9C:
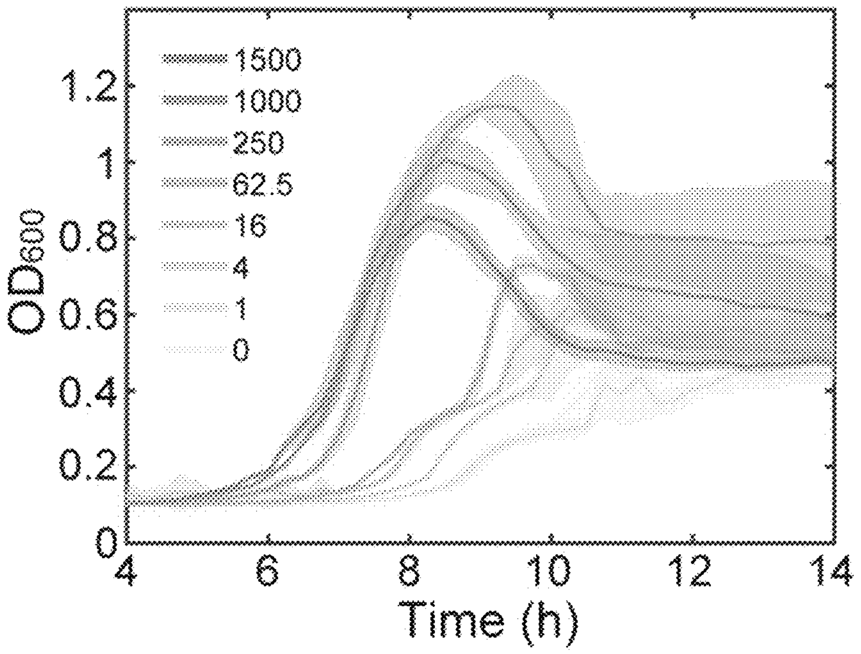
Figure 9D:
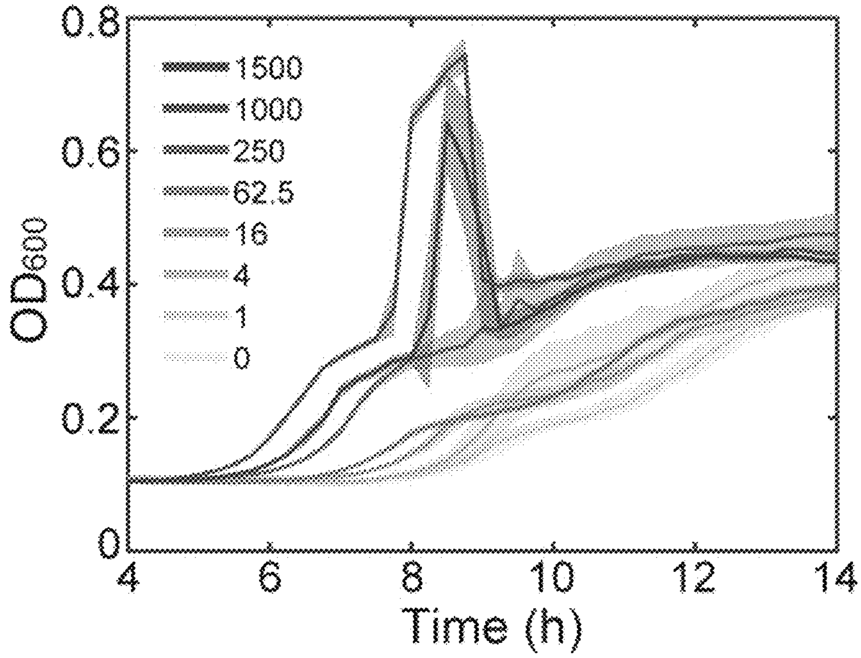
Figure 10A:
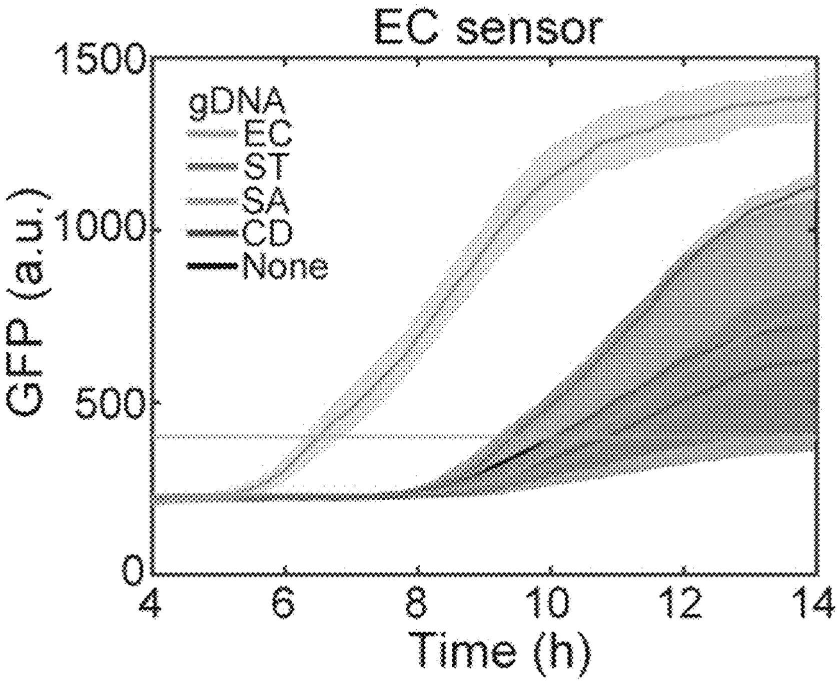
FIGS. 10A-10H. Orthogonality test of the four constructed DNA sensors. Time-series measurements of GFP expression of (FIG. 10A) EC sensor, (FIG. 10C) ST sensor, (FIG. 10E) SA sensor, and (FIG. 10G) CD sensor in liquid medium after the transformation of gDNA extracted from different strains or no gDNA. Line is the average of four technical replicates and the shaded region represents one standard deviation from the average. A threshold of GFP 400 was used to determine the detection time for the target gDNA and non-target gDNA or no gDNA for (FIG. 10B) EC sensor, (FIG. 10D) ST sensor, (FIG. 10F) SA sensor, and (FIG. 10H) CD sensor. Unpaired t-test was performed to determine if the detection time for the target gDNA is different from non-target gDNA or no gDNA. Based on the calculated p-values, sensors expressed GFP hours earlier only in the presence of target gDNA.
Figure 10B:
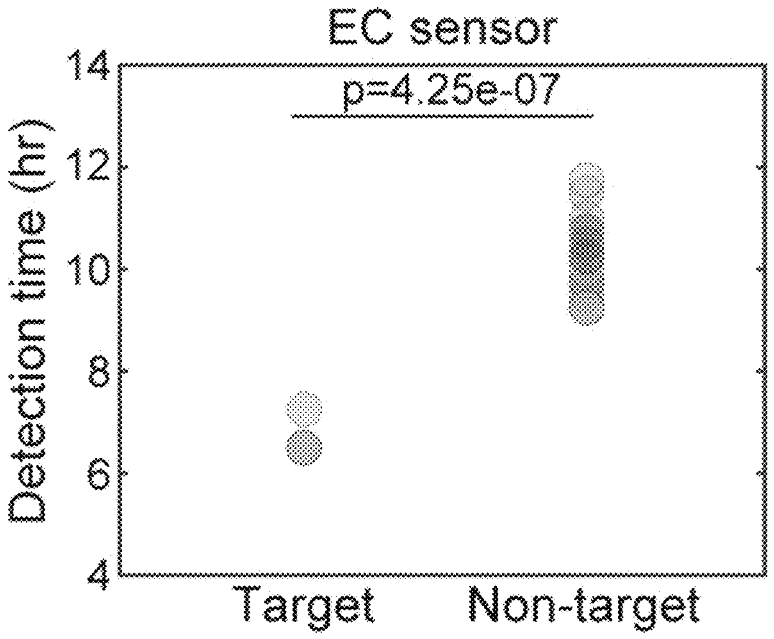
Figure 10C:
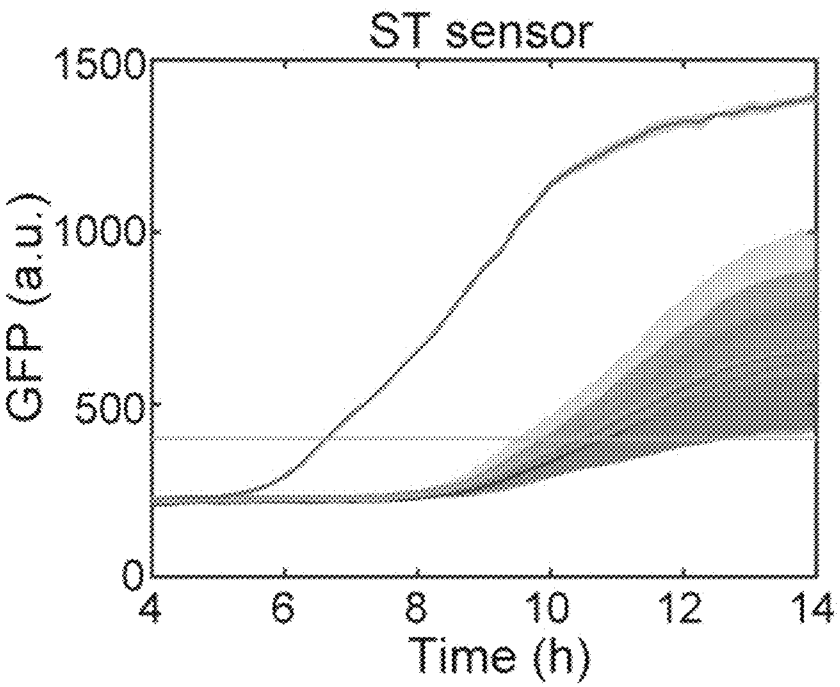
Figure 10D:
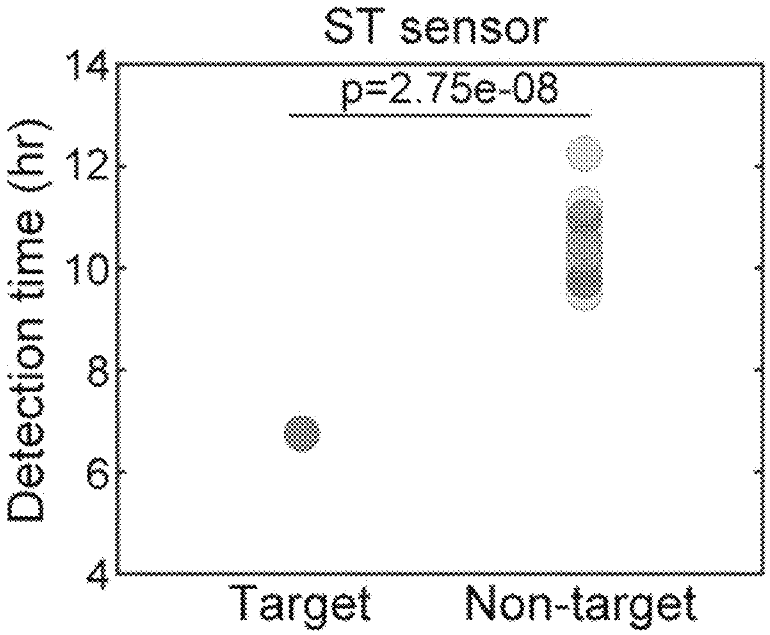
Figure 10E:
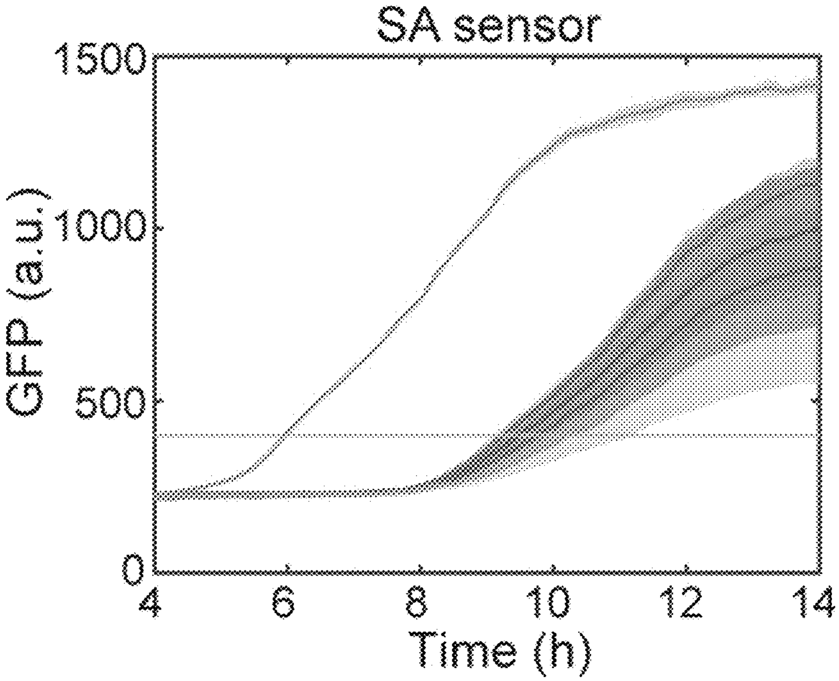
Figure 10F:
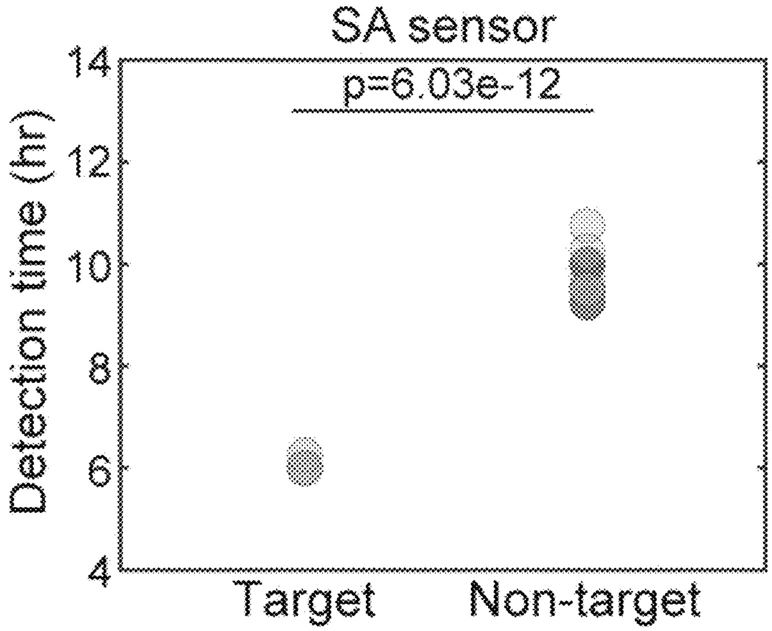
Figure 10G:
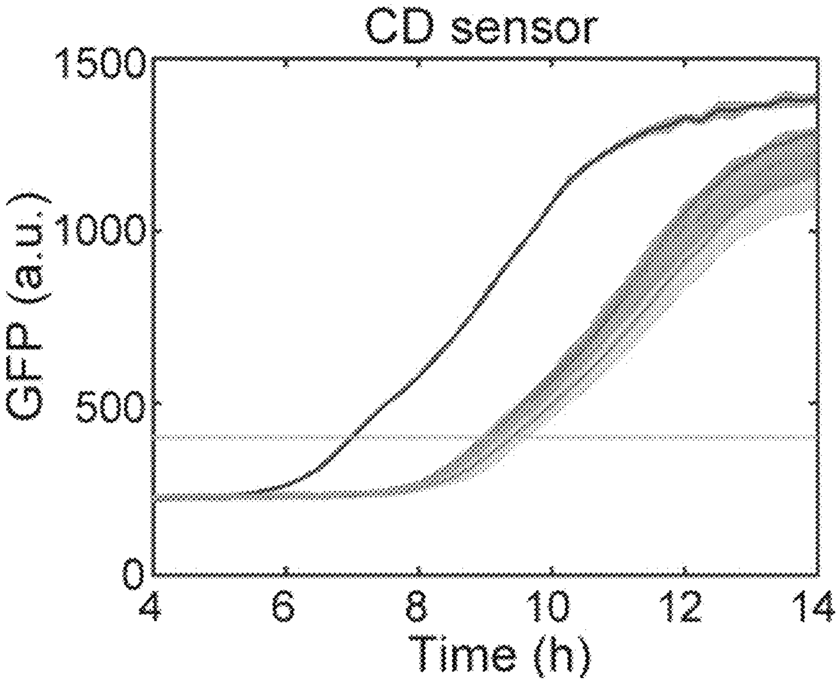
Figure 10H:
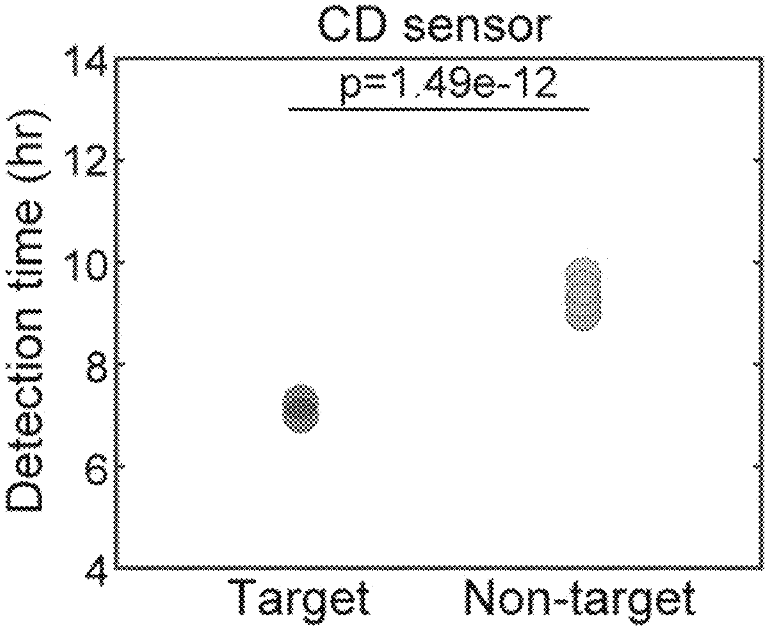

The selected set of target DNA sequences are highly conserved within a given species (ST sensor: 94%, SA sensor: 96%, and CD sensor: 96% all with >95% coverage and >95% identity similarity). In addition, some of the sequences are linked to virulence activities of the pathogen or encode enzymes that are critical for fitness[24-26]. To further explore the conservation of the target sequences across different strains, we performed nucleotide BLAST using the NCBI Database to quantify the homology coverage and sequence similarity across species. The pathogenicity island sipBCDA in *S. typhimurium* was found only in *Salmonella enterica* species and infrequently observed in other species (FIG. 7A). Homologs in other species have low coverage and identity similarity, suggesting that the pathogenicity island could be a good target sequence for this species (FIG. 7A). The heme biosynthesis pathway hemEH in *S. aureus* and phenylalanyl-tRNA synthetase pheST in *C. difficile* are conserved in some closely related strains with varying degrees of similarity and coverage (FIGS. 2I and 2K). The *E. coli* MG1655 xdhABC purine catabolism operon is found in other closely related bacteria such as *Shigella* with high coverage and identity similarity (FIG. 7B). Although the target sequences for building the different DNA sensor strains varied in the degree of specificity based on bioinformatic analyses, a detailed characterization of circuit performance could guide the design of optimized cell-based DNA sensors for future applications.

Figure 2A:
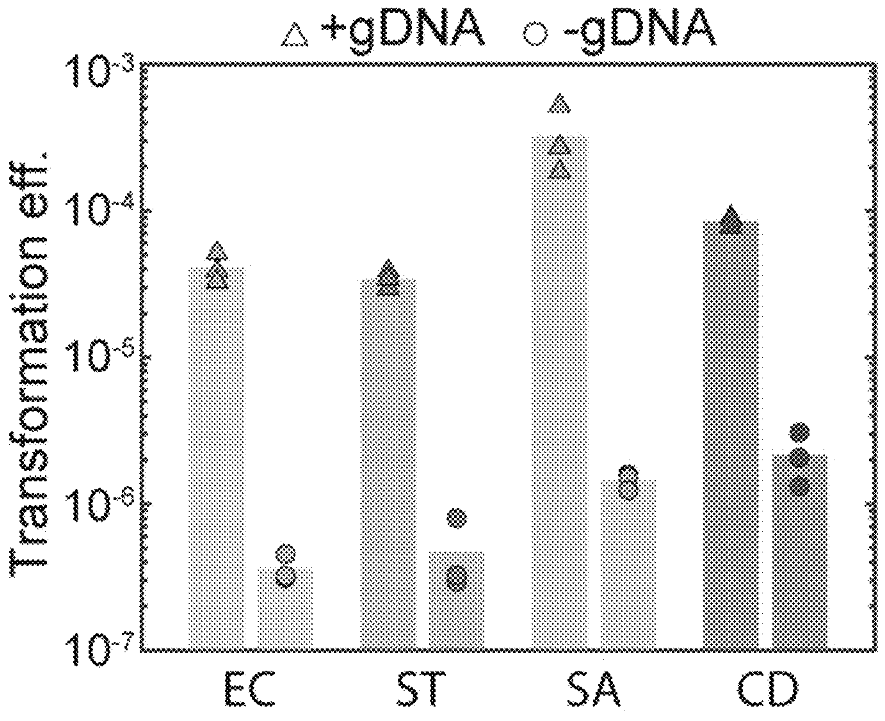
FIGS. 2A-2L. Cell-based sensors can detect DNA from diverse bacteria with high sensitivity and specificity.
Figure 2B:
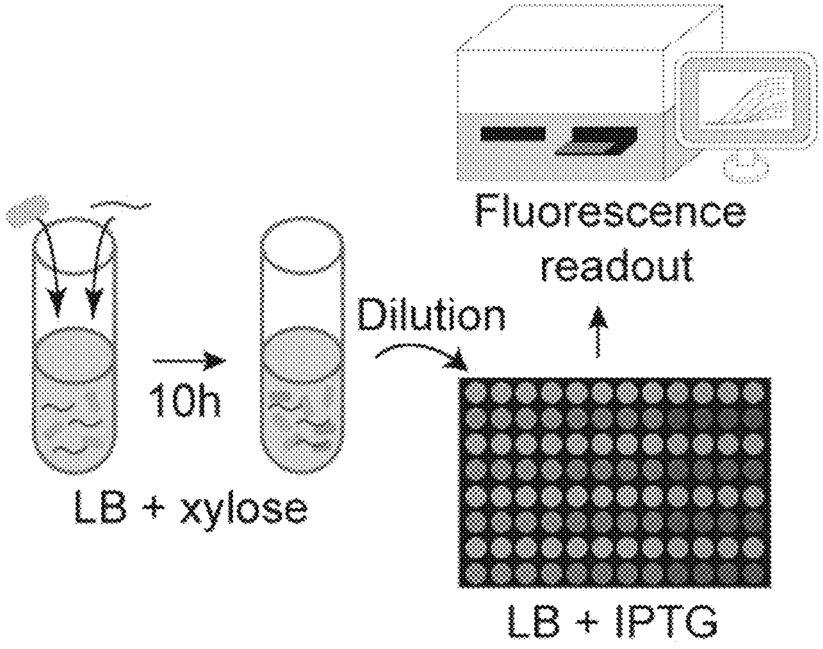
Figure 2C:
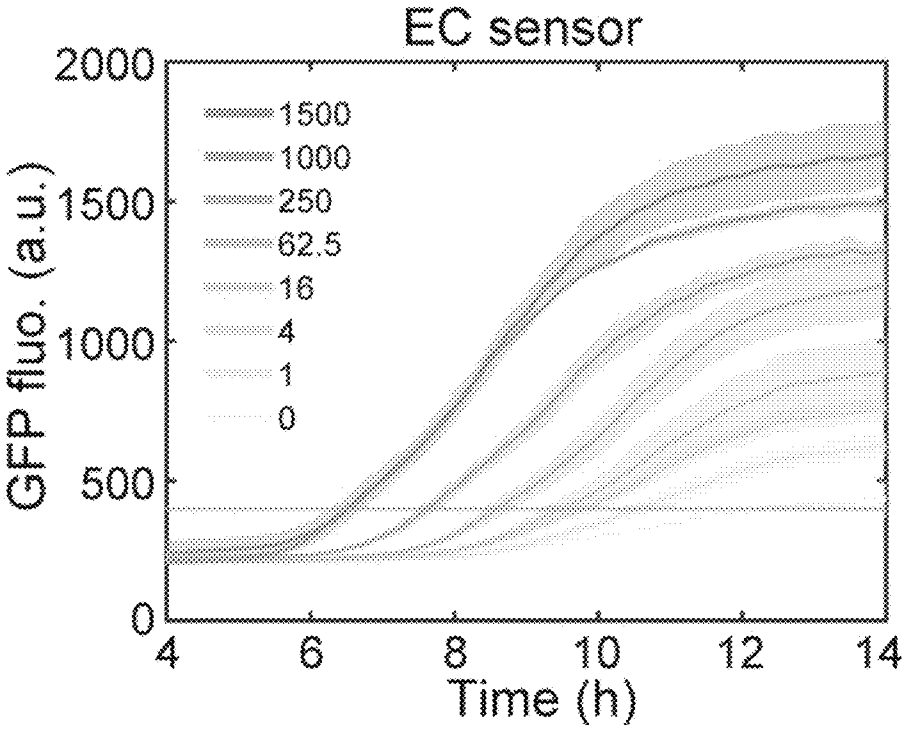
Figure 2D:
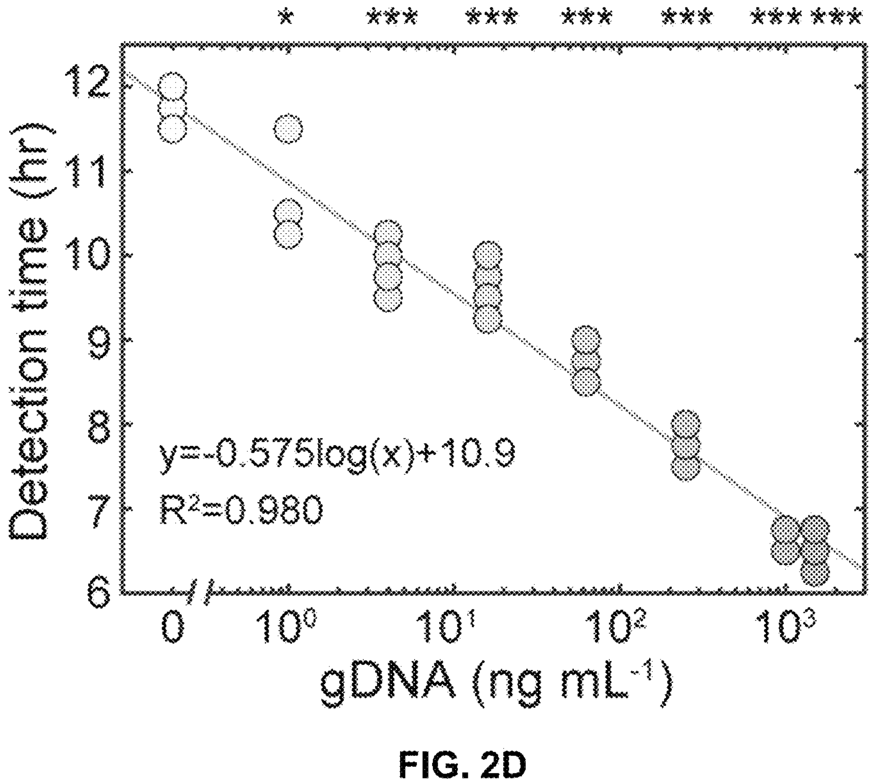
Figure 2E:
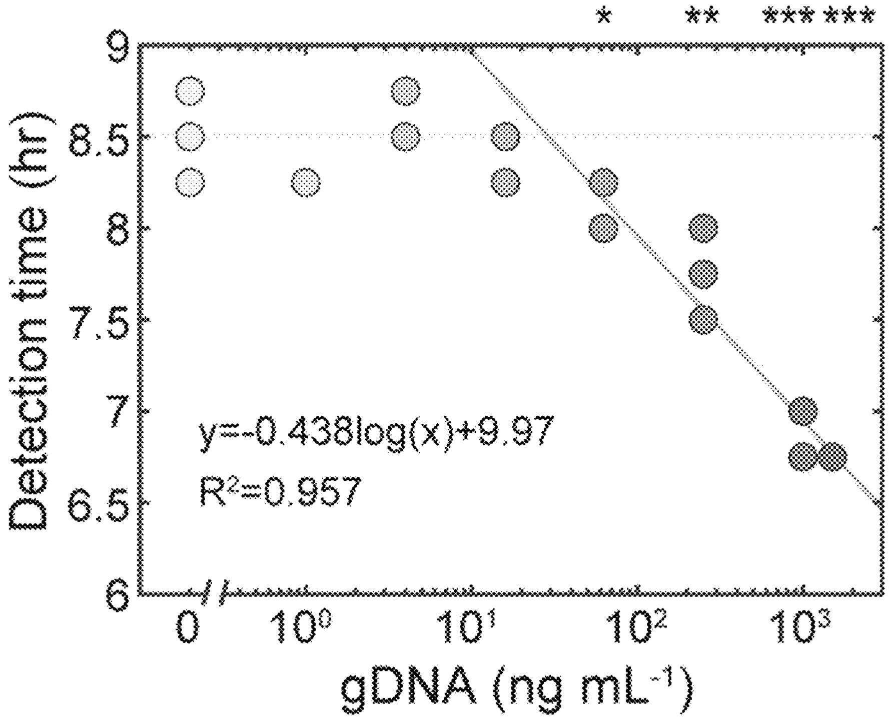
Figure 2F:
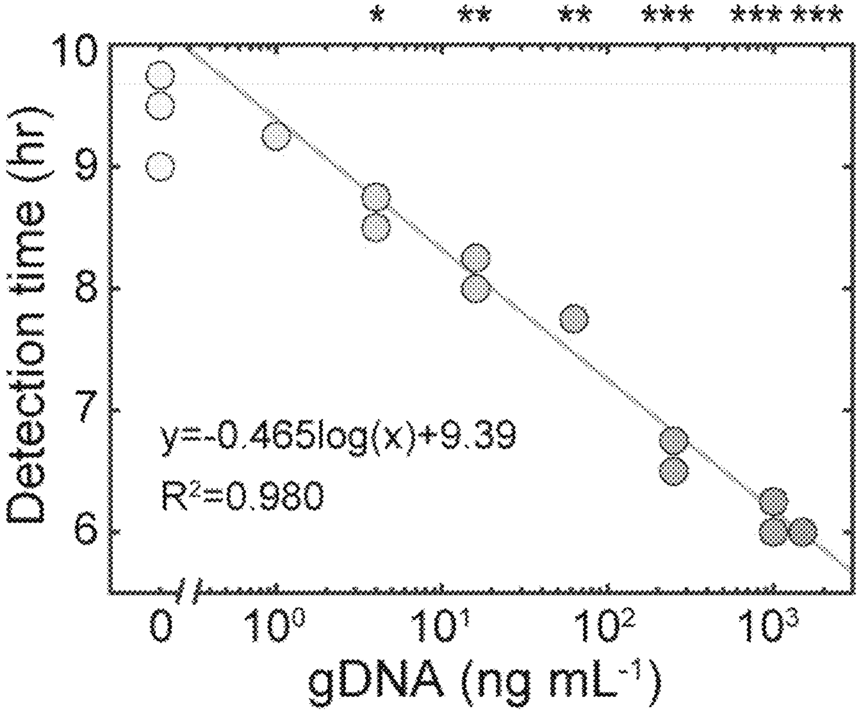
Figure 2G:
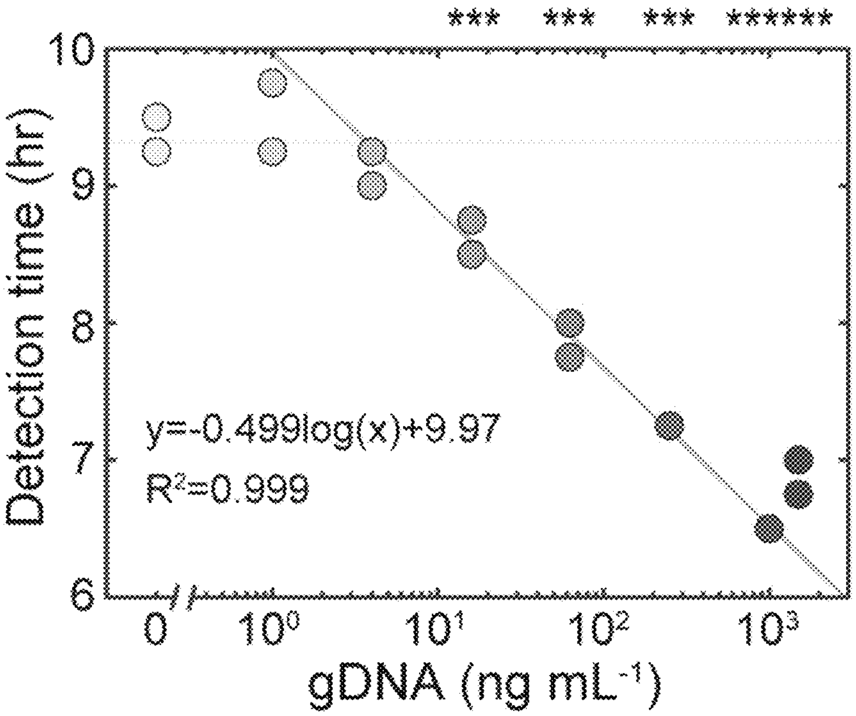
Figure 2H:
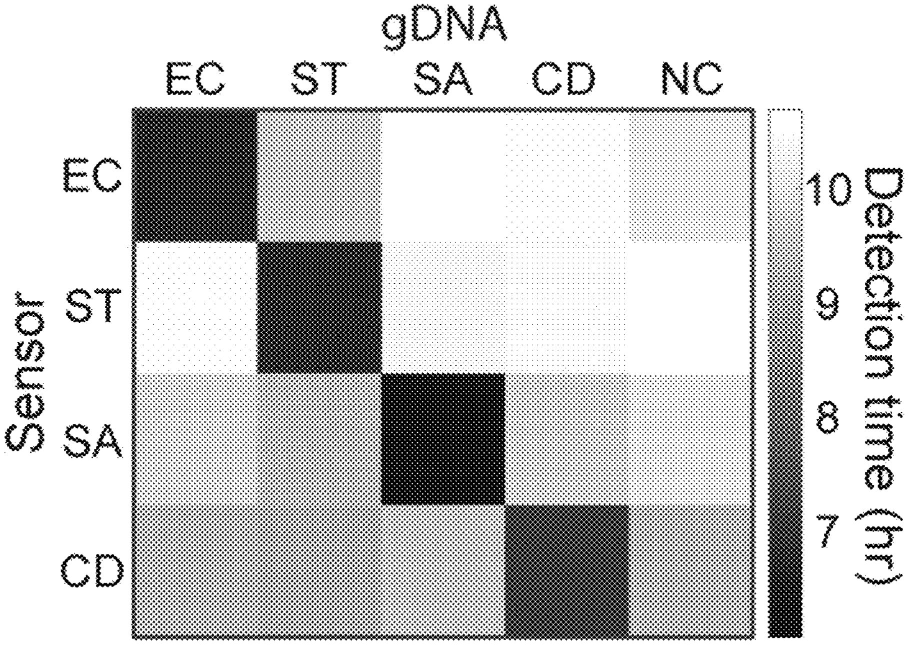
Figure 2I:
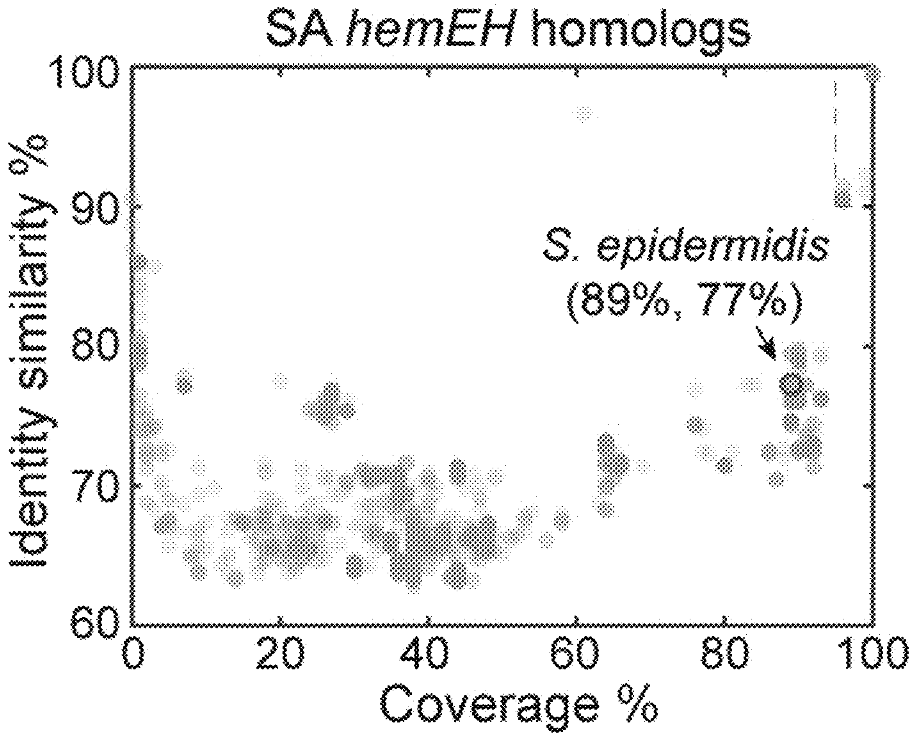

The four sensors robustly detected the presence of 100 ng/mL target gDNA over background (0 ng/mL gDNA) based on transformation efficiency (FIG. 2A). We evaluated the sensitivity of each DNA sensor strain by performing time-series GFP measurements in liquid culture after being transformed with a wide range of gDNA concentrations (0-1500 ng/mL gDNA) from single species (FIGS. 2B, 2C, and 8A-8C). We evaluated the time required for each culture to display a fluorescence level higher than a threshold (i.e. detection time) (FIGS. 2C and 8A-8C). The sensitivity of the circuit was evaluated as the lowest gDNA concentration that yielded a statistically significant difference in the detection time in the presence versus absence of gDNA (FIGS. 2D-2G).

The relationship between the log transformed gDNA concentration and detection time is linear due to the exponential growth of the fluorescent *B. subtilis* sub-population successfully transformed with the input target sequence (FIG. 9A-9D). Therefore, to assess the range of gDNA concentrations that can be accurately sensed, we inferred the parameters of a linear function fit to the log transformed gDNA concentration versus detection time (FIGS. 2D-2G). The inferred slope of the linear function is determined by the cell doubling time (~0.5 hour) and intercept is determined by the background mutation frequency (FIGS. 2D-2G). The EC, SA, and CD DNA sensor strains displayed high sensitivity of 1-16 ng/mL ($10^5$-$10^6$ chromosome copy number/mL), whereas the ST sensor displayed a lower sensitivity (62.5 ng/mL, $10^7$ chromosome copy number/mL). While the DNA sensor strains displayed lower sensitivities than quantitative real-time polymerase chain reaction (qPCR) reported for *E. coli* ($3.5\times10^3$ CFU/mL in pure culture[27]), the observed sensitivities are within the range of the sensitivities reported for the lateral flow immunoassay ($1.8\times10^5$ CFU/mL for a pure culture of *E. coli*[28]).

To characterize the specificity of each DNA sensor strain to the target sequence, we performed time-series fluorescence measurements in liquid culture in response to all individual species gDNA. The fluorescence signal was observed at a substantially earlier time (6.1-7.1 hr) in the presence of the corresponding species' gDNA than in the presence of a non-target species' gDNA or in the absence of DNA (9.1-10.7 hr) (FIGS. 2H and 10A-10H). This demonstrates that the cell-based DNA sensors were highly specific to the target sequence.

Figure 2J:
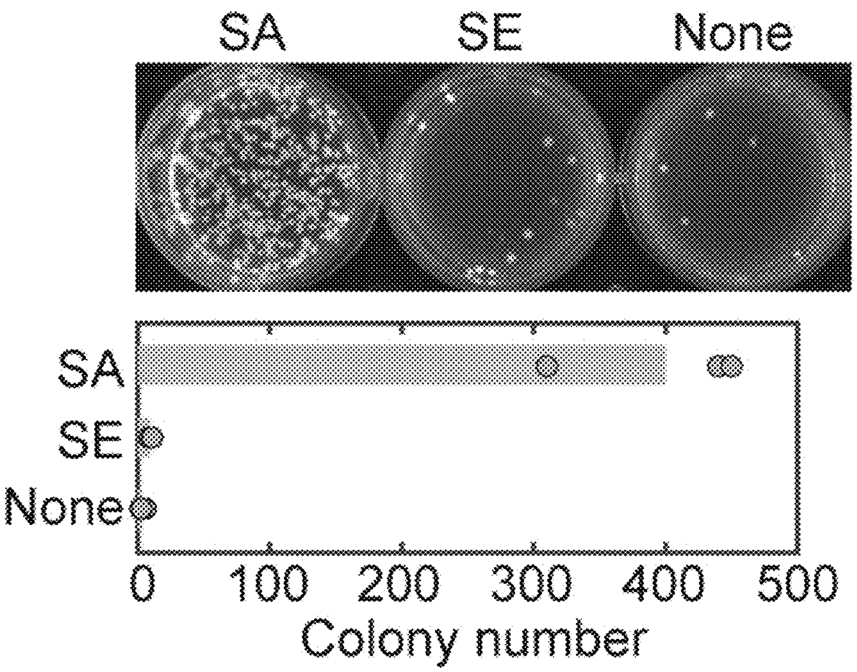
Figure 2K:
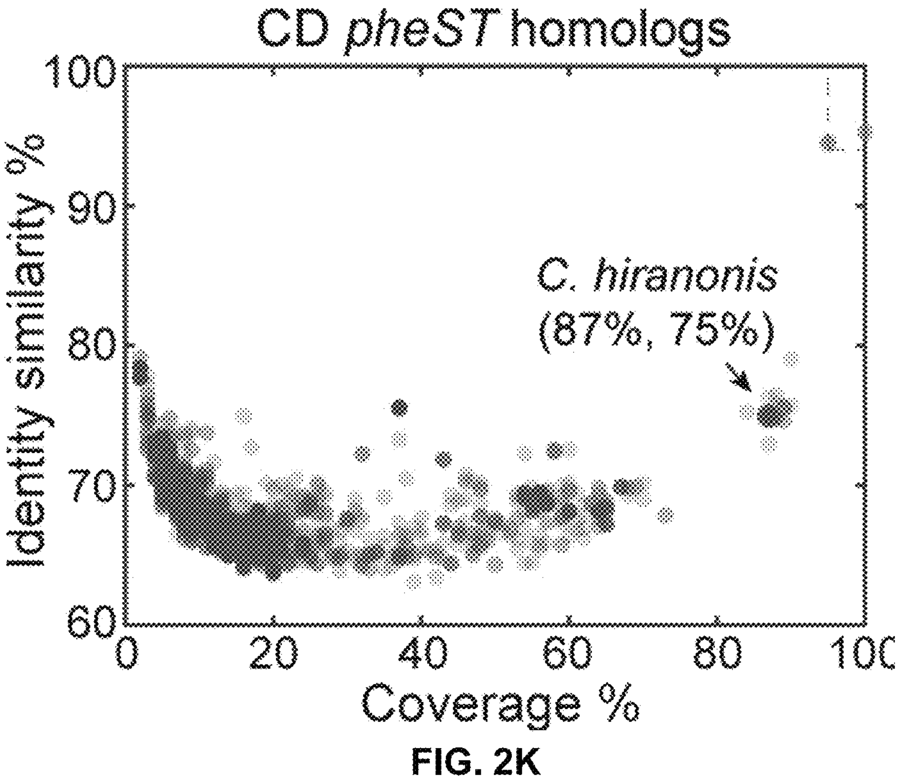
Figure 2L:
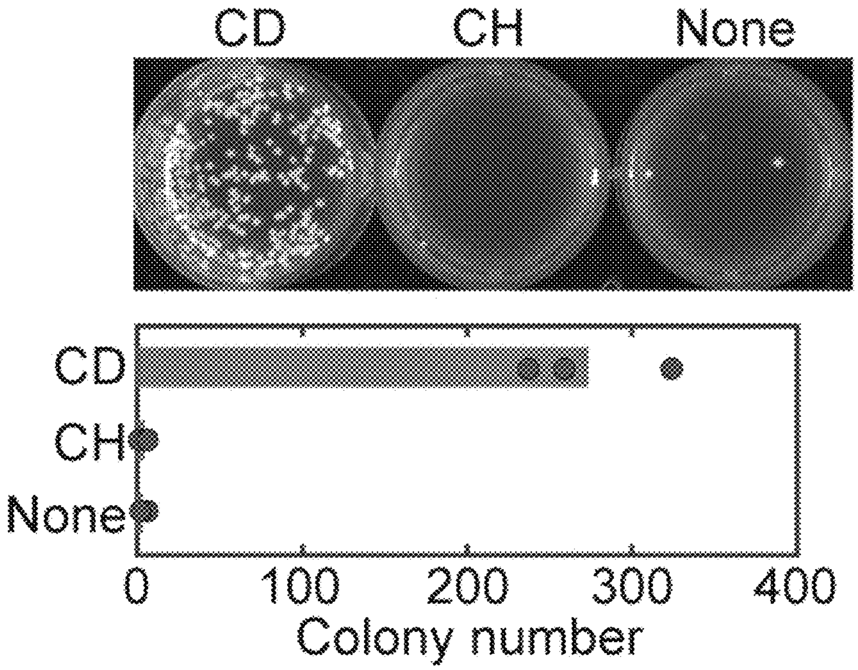
Figure 11A:
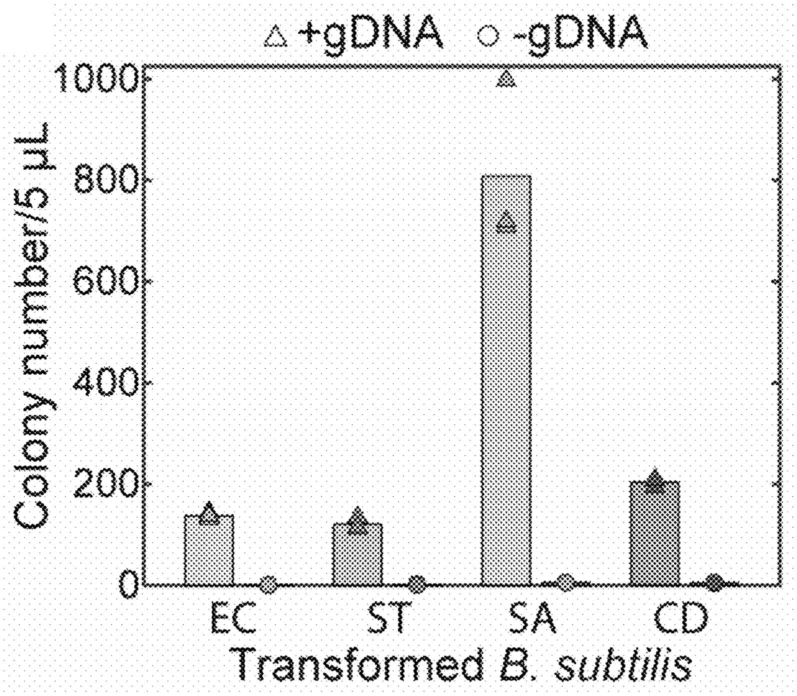
FIGS. 11A and 11B. Detection efficiency based on number of transformed cells.
Figure 11B:
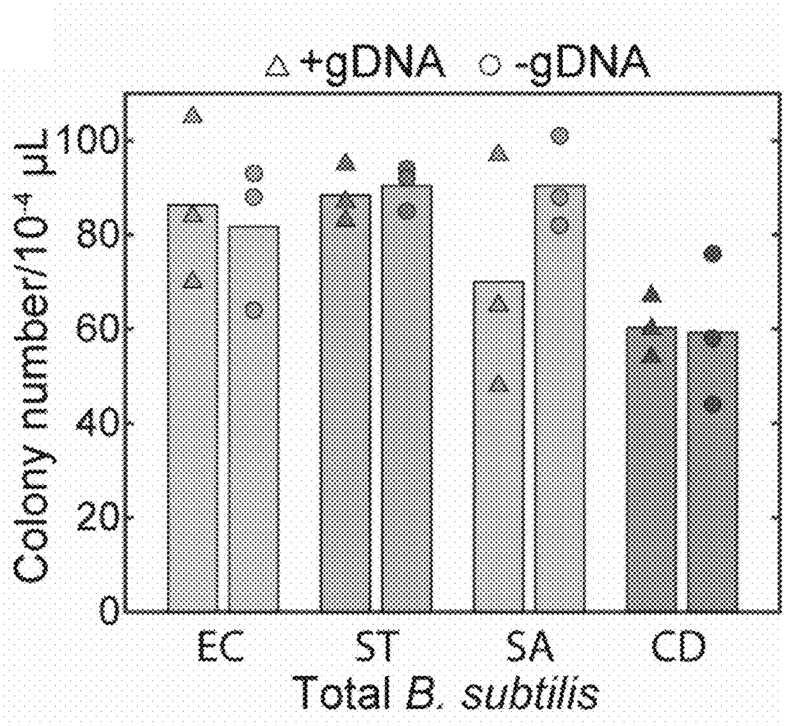

In the context of microbial communities, the cell-based DNA sensors may need to distinguish between closely related species. Therefore, we evaluated the ability of the DNA sensors to distinguish between closely related species with similar target sequences. To this end, we measured the transformation frequency of the SA sensor in the presence of gDNA (100 ng/mL) derived from *S. epidermidis. S. epidermidis* is a closely related human skin commensal bacterium that harbors a similar hemEH sequence to the SA sensor landing pad region (89% coverage and 77% identity similarity) (FIG. 2I). Since the number of total *B. subtilis* colonies was similar in the presence and absence of gDNA, we quantified the number of transformed colonies as opposed to transformation efficiency (FIGS. 2A, 11A, and 11B). The number of colonies in the presence of *S. epidermidis* gDNA (SE) was substantially lower than in the presence of *S. aureus* gDNA (SA) and similar to the absence of DNA (FIG. 2J). Similarly, we characterized the ability of the CD sensor to detect gDNA derived from a human gut commensal bacterium *C. hiranonis*, a close relative of *C. difficile* that contains a similar pheST sequence in its genome to the landing pad region in CD sensor (87% coverage and 75% identity similarity). The number of colonies in the presence of 100 ng/mL *C. hiranonis* gDNA (CH) was substantially lower than in the presence of *C. difficile* gDNA (CD) and also similar to the absence of DNA (FIGS. 2K and 2L). These data demonstrate that the cell-based DNA sensors are highly specific to species that harbor an exact match to the target sequence. Therefore, the sensors do not display false positives in the presence of closely related species that harbor similar target sequences. The high specificity of the sensors is due to the stringent requirements for homologous recombination in *B. subtilis*[13,29].

Multiplexed Detection of Pathogen DNA in Complex Samples

Figure 3A:
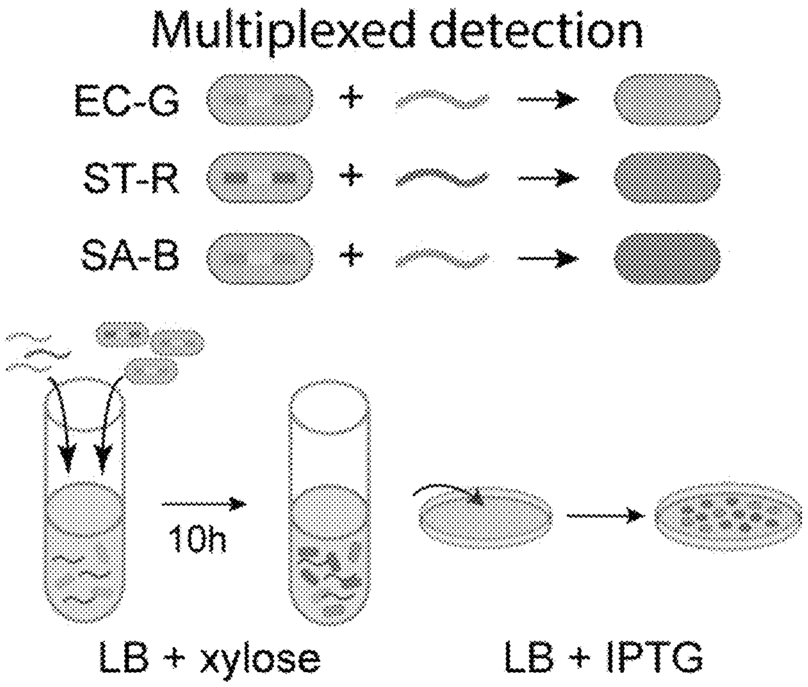
FIGS. 3A-3F. DNA sensors can perform multiplexed detection in complex DNA samples.
Figure 3B:
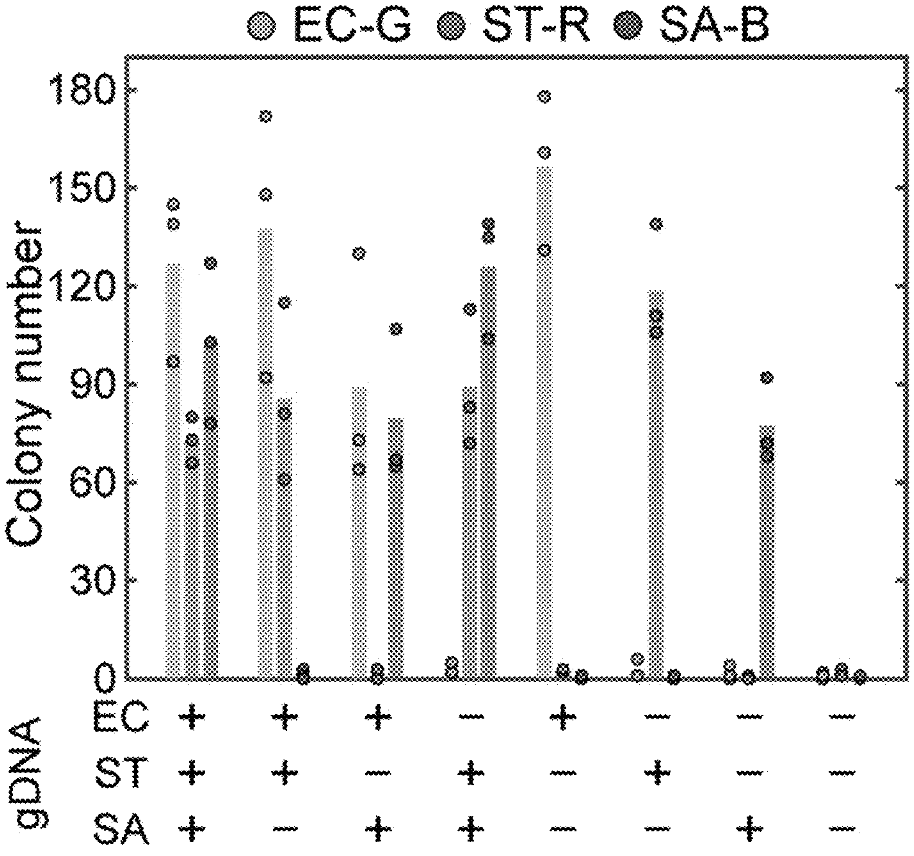
Figure 3C:
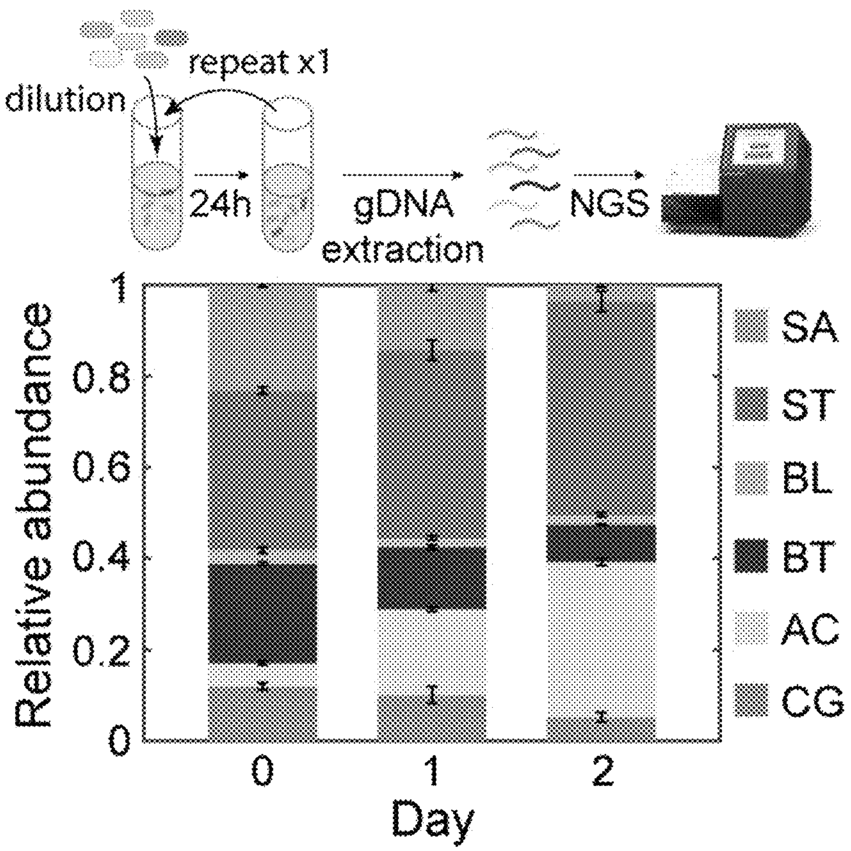
Figure 12:
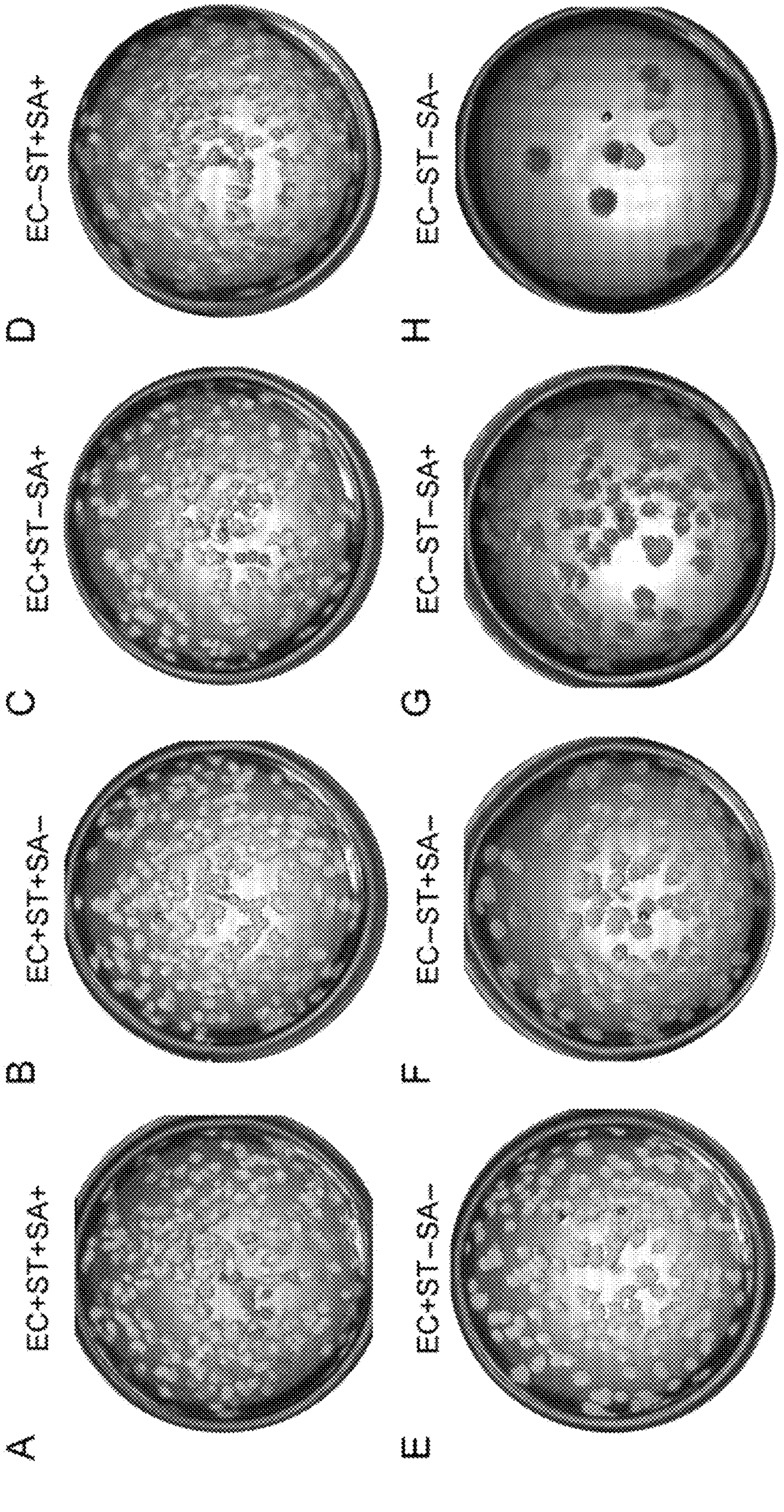
FIG. 12. Representative fluorescence images of transformed EC-G, ST-R, and SA-B sensors for multiplexed detection. Colonies with different fluorescence on agar plate after the transformation of combinations of extracted gDNA in a mixture of EC-G, ST-R, and SA-G sensors. Sensors were transformed with (A) *E. coli, S. aureus* and *S. typhimurium* gDNA, (B) *E. coli* and *S. typhimurium* gDNA, (C) *E. coli* and *S. aureus* gDNA, (D) *S. typhimurium* and *S. aureus* gDNA, (E) *E. coli* gDNA, (F) *S. typhimurium* gDNA, (G) *S. aureus* gDNA, and (H) no gDNA.

Since certain future applications may require sensing of more than one organism, we tested the ability of the DNA sensors to detect more than one species within mixed DNA samples. To this end, we constructed individual sensors with orthogonal fluorescent reporters to achieve multiplexed DNA detection. Exploiting the modularity of the circuit, we constructed an RFP-labeled ST sensor (ST-R) and a BFP-labeled SA sensor (SA-B), in addition to the GFP-labeled EC sensor (EC-G) (FIG. 5C). We introduced gDNA (200 ng/mL) extracted from each of the three target strains into a culture containing EC-G, ST-R, and SA-B sensors and determined the number of fluorescent colonies for each reporter (FIG. 3A). The sensors accurately reported the presence/absence of all combinations of species' gDNA reliably (FIGS. 3B and 12). Therefore, a mixture of DNA sensor strains each individually labeled with a unique fluorescent reporter enabled multiplexed detection of gDNA derived from different species. To investigate if multiplexed detection can be achieved for samples derived from a complex microbial community, we constructed a four-member human gut community composed of diverse commensal bacteria from three major phyla in human gut—*Anaerostipes caccae* (AC, Firmicutes), *Bacteroides* thetaiotaomicron (BT, Bacteroidetes), *Bifidobacterium longum* (BL, Actinobacteria), and *Clostridium asparagiforme* (CG, Firmicutes). This community also contained the target pathogens *S. typhimurium* (ST) and *S. aureus* (SA). We tested whether the DNA sensors could accurately report the relative abundance of the two pathogens during community assembly. The 6-member community was inoculated in equal initial species proportions based on absorbance at 600 nm (OD600, Day 0) and cultured anaerobically for 24 hr (Day 1). An aliquot of the community was transferred to fresh media and community composition was characterized following an additional 24 hr (Day 2). Based on 16S rRNA gene sequencing, the abundance of *S. typhimurium* was similar as a function of time whereas the abundance of *S. aureus* decreased over time (FIG. 3C).

Figure 3D:
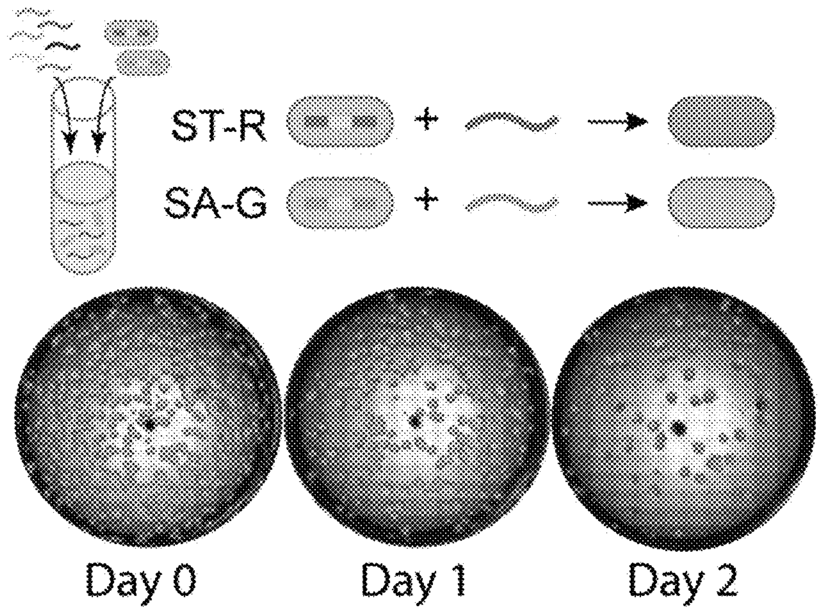
Figure 3E:
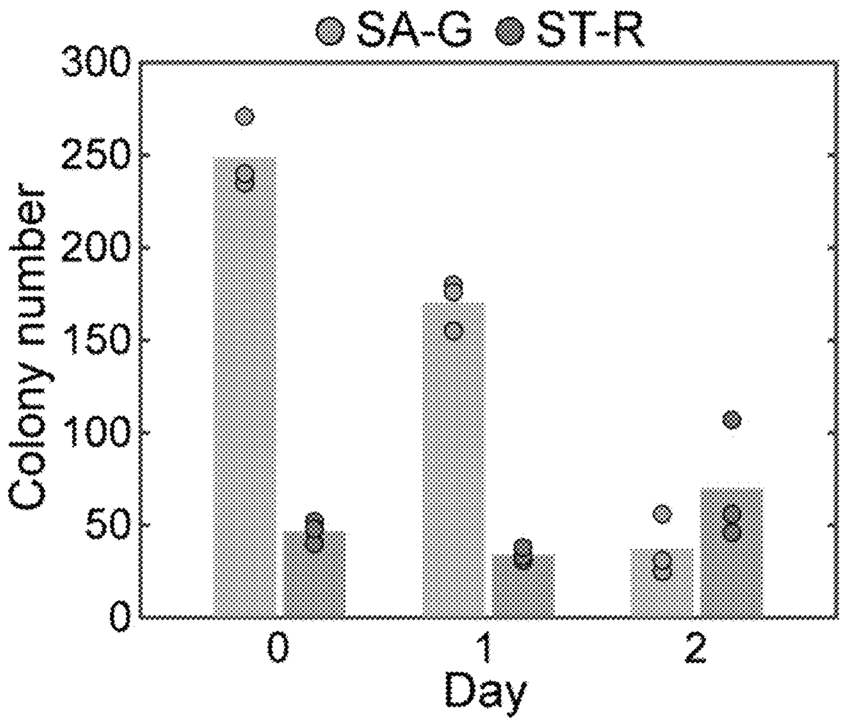
Figure 3F:
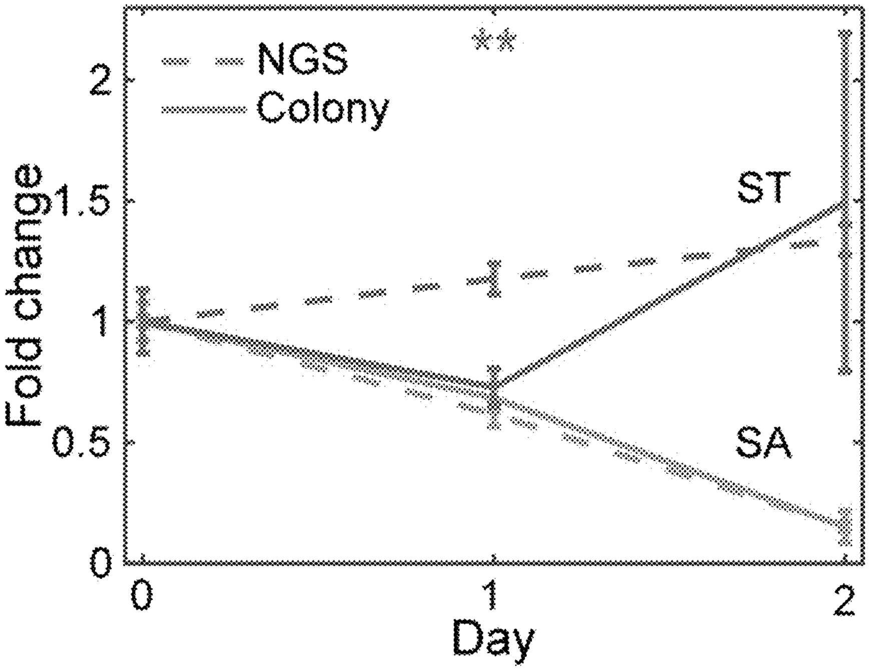
Figure 13A:
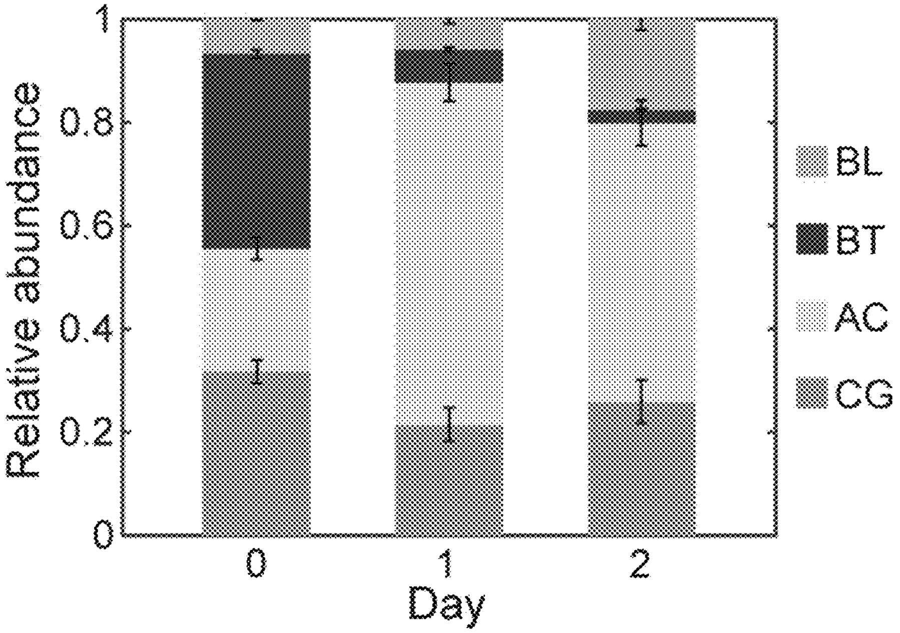
FIGS. 13A and 13B. Negative control for the multiplexed detection in complex DNA samples.
Figure 13B:
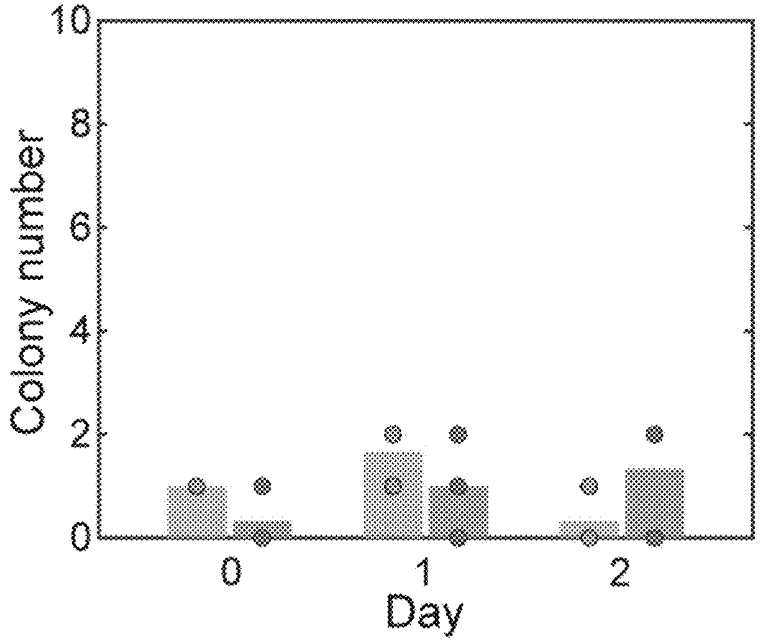

We characterized the ability of the DNA sensors to accurately track the temporal trends in species abundance by introducing purified community gDNA collected at different times into a mixed culture of the ST-R and SA-G sensors (FIG. 3D). Due to the low abundance of target species in the sample, a higher amount of DNA (1 μg/mL) was used for transformation. Consistent with the trends based on 16S rRNA gene sequencing, the number of GFP fluorescent colonies of the SA-G sensor decreased at sequential time points, whereas the number of RFP fluorescent colonies of ST-R sensor were similar at sequential time points (FIGS. 3D-3F). The SA sensor displayed better performance in mirroring the trend from 16S rRNA gene sequencing than the ST sensor, consistent with its higher sensitivity than other sensors (FIGS. 2A, 3E, and 3F). For the community lacking *S. typhimurium* and *S. aureus*, a much smaller number of background colonies was detected than in the 6-member community. This implies that the ST and SA sensors were specific to the target species gDNA and did not generate false positives in the presence of the other constituent community member gDNA (FIGS. 13A and 13B). In sum, our results show that accurate multiplexed DNA detection can be achieved in samples derived from multi-species microbial communities.

Detection of Target Species without DNA Extraction

Figure 4A:
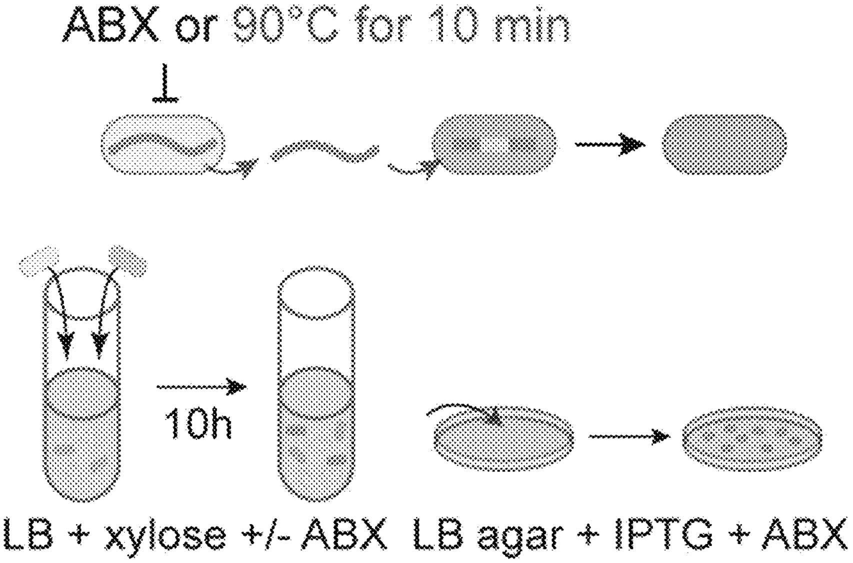
FIGS. 4A-4D. DNA sensors can directly detect target species without DNA extraction.
Figure 4B:
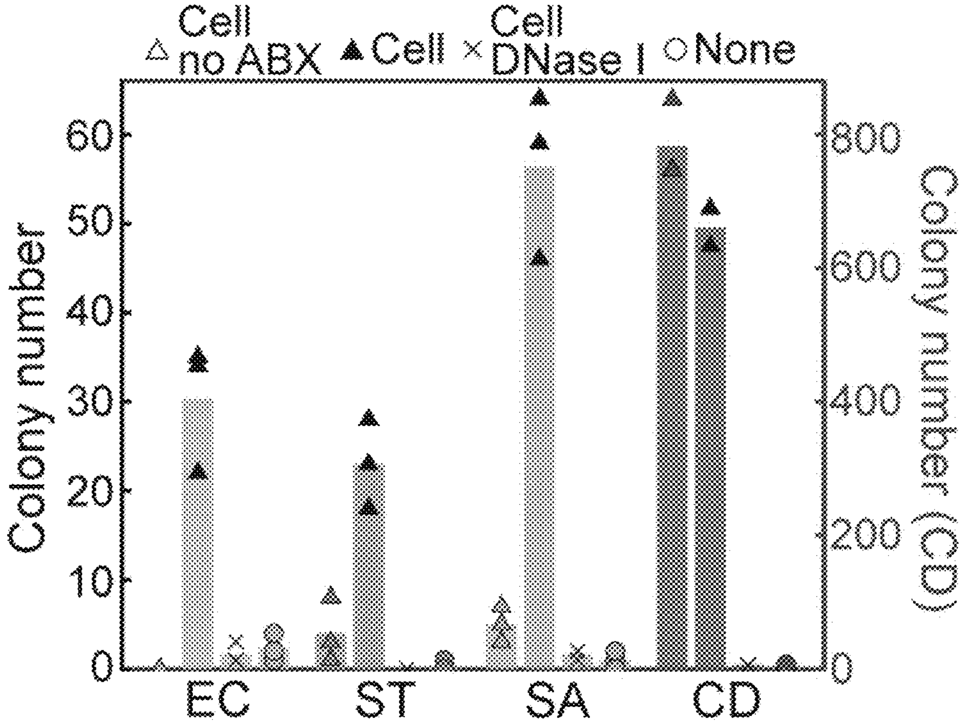
Figure 4C:
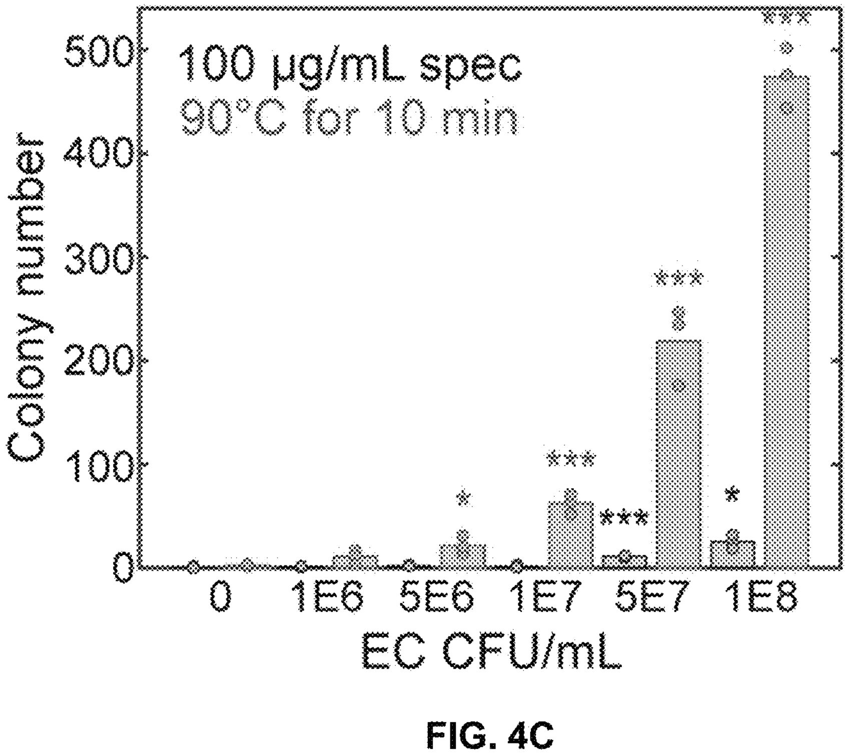

Specific bacterial species have been shown to release eDNA in response to environmental stimuli[11], suggesting that the DNA sensor could detect species without requiring prior gDNA purification. To test this possibility, we co-cultured individual DNA sensor strains with the corresponding donor species with an initial OD600 0.1 of the target strain ($1.22\times10^8$ CFU/mL, $1.07\times10^8$ CFU/mL, $3.2\times10^8$ CFU/mL, and $1.1\times10^7$ CFU/mL for *E. coli, S. typhimurium, S. aureus*, and *C. difficile*, respectively) (FIG. 4A). Since the other species could compete with *B. subtilis*, we introduced specific antibiotics (ABX) to inhibit the growth of the donor cells and enhance donor eDNA release. The DNA sensor strains are resistant to the antibiotics since they harbor the appropriate antibiotic resistance genes. In the presence of 100 μg/mL spectinomycin, the DNA sensors displayed robust detection of *E. coli, S. typhimurium*, and *S. aureus* (FIG. 4B). The addition of spectinomycin was not required for *C. difficile* detection since the growth of *C. difficile* is negatively impacted by the presence of oxygen[30]. To confirm the transformation was mediated by the eDNA released from the target strain, DNase I (1 unit/mL) was added into the co-culture. The number of transformed cells was substantially lower in the presence of DNase I, indicating that DNA detection occurred via natural transformation in the co-cultures (FIG. 4B). Antibiotic resistance is prevalent in microbiomes and may not be used universally as a treatment for the donor cells. Therefore, we tested if heat treatment could be used to efficiently release donor cell DNA. Incubation of *E. coli* at 90° C. for 10 minutes substantially enhanced the EC sensor detection limit ($5\times10^6$ CFU/mL) compared to the addition of spectinomycin (FIG. 4C). In sum, detection of target DNA sequences directly from crude samples in the absence of DNA purification could enable the deployment of the DNA sensors for different future applications.

Figure 4D:
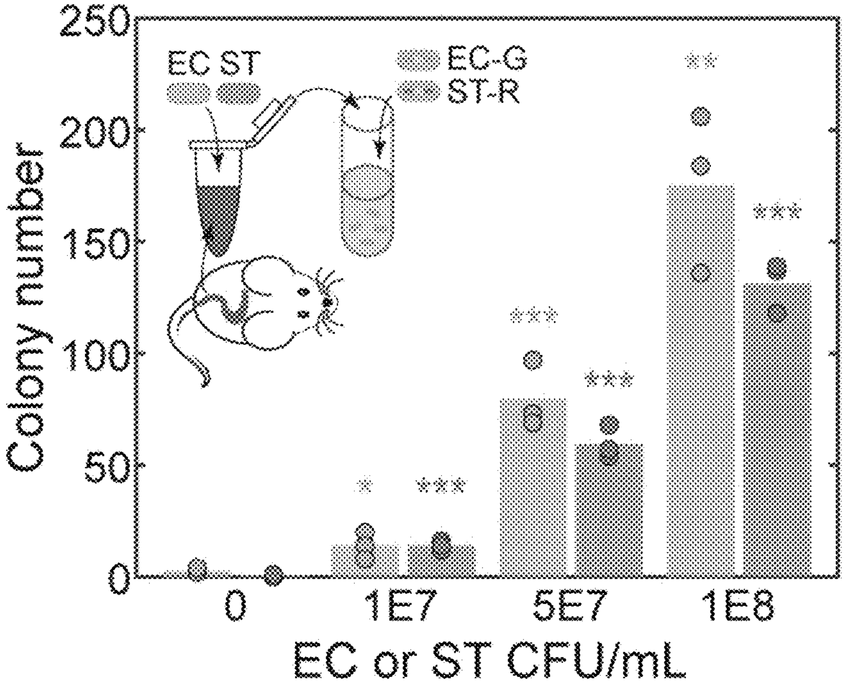
Figure 14B:
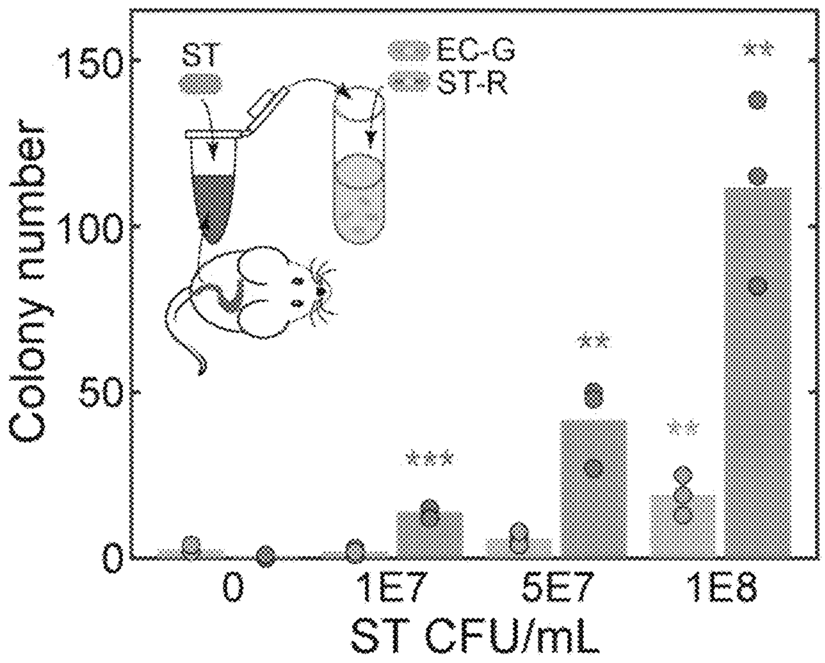

To evaluate the robustness of the DNA sensing function, we characterized the performance of the DNA sensors for multiplexed detection of spike-in bacteria in the presence of cecal contents derived from germ-free mice that were orally gavaged with a defined bacterial consortium (Methods). Mouse ceca contain other bacterial species, host cells and other chemical compounds (e.g. dietary factors), and thus can be used to evaluate the robustness of the DNA sensor. To this end, we introduced varying amounts of *E. coli* and *S. typhimurium* into 10 mg of mouse ceca, incubated these samples at 90° C. for 10 minutes, and then transferred the samples into a mixed culture containing the EC-G and ST-R sensors (FIG. 4D). Our results demonstrated that both sensors can detect *E. coli* and *S. typhimurium* cells in ceca without DNA extraction. In particular, the EC and ST sensors displayed a detection limit of $10^7$ CFU/mL (FIG. 4D). In samples containing a single donor species, high density of *E. coli* or *S. typhimurium* ($10^8$ CFU/mL) yielded infrequent false positives for the multiplexed DNA detection. This suggests that further optimization of the DNA sensors may be needed in complex samples containing high donor cell densities that are heat treated (FIGS. 14A and 14B). In sum, we show that the cell-based DNA sensors can robustly perform DNA detection of heat-treated samples that contain the target sequence.

Discussion

Here we engineered the naturally competent bacterium *B. subtilis* to sense and respond to specific DNA sequences. DNA sensing can be achieved for purified DNA or eDNA released from pre-treated samples containing donor cells harboring the target sequence. We demonstrate that DNA sensing can be sensitive and specific, and multiplexed sensing can be achieved by engineering sensors with orthogonal reporter genes. Detection of species using a living cell-based DNA sensor strain opens avenues for future research for versatile sensing of species and does not rely on chemical or physical signals[31,32]. Since our circuit design is modular, customized sensors could be constructed in the future for the detection of sequences derived from diverse organisms including viruses, fungi and mammalian cells.

The DNA detection limit is impacted by the frequency of background mutations and could be improved by reducing the background genetic mutation rate. For example, counter-selectable markers[33] that can achieve lower background mutation rate could be used to optimize the strength of negative growth selection. The mutation rate can also be reduced by deleting endogenous genes in *B. subtilis* that promote mutagenesis such as the transcription conflict factor mfd[34]. The reduction of mutation rates is also critical for long-term implementation of living DNA sensors in the environments[35].

The time required for DNA detection using the cell-based DNA sensors is relatively slow compared to other diagnostic methods[36]. In particular, the total time required for DNA detection including transformation and selection is approximately one day, which is not suitable for certain applications that require a rapid response. To reduce the detection time, directed evolution or rational design of the natural competence pathway could be used for enhancing the transformation efficiency of *B. subtilis*[37]. This in turn would reduce the time required for transformation and detection of GFP in liquid media. In addition, some naturally competent bacteria such as *Streptococcus pneumoniae* can achieve 50% transformation efficiency[38]. This transformation efficiency is substantially higher than our constructed DNA sensors ($10^{-5}$-$10^{-4}$). With a suitable chassis with a high transformation ability, GFP expression could be observed more rapidly following transformation, which requires a few hours.

The living DNA sensors have potential for in vitro DNA detection applications. One unique feature of the cell-based DNA sensor is the long homology within the landing pad region of the circuit, distinct from PCR-based methods that use short recognition sequences. Therefore, the target DNA sequence can be specified at the level of genes or pathways (i.e. biosynthetic gene clusters), and the DNA sensor could be used to mine such sequences from metagenomic DNA[39].

In addition, the access to NGS sequencing or multiplexed qPCR may not be widely available[36,40]. By contrast, the cell-based DNA detection is relatively simple and cost-effective. The DNA sensors may be suitable for large-scale screening with limited experimental resources. Further, *B. subtilis* sensors could be stored as spores for easy and long-term storage[41]. The metrics used in this study (sequence identity similarity and coverage) should be systematically examined using existing sequencing data and experimental characterization to elucidate sequence design rules for homologous recombination. In addition, tools from machine learning could be used to predict the impact of landing pad sequences on the fitness of *B. subtilis* to minimize any negative effects on growth rate[42].

One of the most unique aspects of this system is the potential for in situ DNA detection. *B. subtilis* has been shown to colonize or reside temporarily in diverse environments including soil and the mammalian gastrointestinal tract[43,44], enabling in situ DNA monitoring. For example, living DNA sensors could be introduced into gastrointestinal tract or plant-associated environment to monitor microbiome dynamics by sensing and recording in real-time[45]. The sensing mechanisms could be coupled to the release of antimicrobials to target specific pathogens[46]. A recent study demonstrated that the naturally competent bacterium *Acinetobacter baylyi* (*A. baylyi*) can be engineered to detect tumor DNA in the mouse colon[47], demonstrating a potential application of in situ DNA detection. In their study, the native CRISPR system in *A. baylyi* was exploited to detect a single mutation in the KRAS gene in cancer cells. Similar CRISPR systems could be incorporated into our current circuit design in the future to discriminate between single-nucleotide differences. In sum, we believe that engineering DNA-sensing bacteria could open new avenues for both in vitro and in situ applications in the future.

Materials and Methods

Plasmid and Strain Construction

All DNA sensor strains were derived from *B. subtilis* PY79. Plasmids constructed in this work are listed in Table 1. The pAX01-comK plasmid was purchased from *Bacillus* Genetic Stock Center (BGSC ID: ECE222) to introduce $P_{xylA}$-comK at the lacA locus in *B. subtilis* PY79 by the selection of MLS (1 μg/mL erythromycin from Sigma-Aldrich and 25 μg/mL lincomycin from Thermo Fisher Scientific) to enhance the transformation efficiency in LB[17,48]. Genes of fluorescent protein GFP(Sp), mCherry, and mTagBFP were cloned from plasmid pDR111_GFP(Sp)[10] (BGSC ID: ECE278), plasmid mCherry_Bsu[11] (BGSC ID: ECE756), and plasmid mTagBFP_Bsu[11] (BGSC ID: ECE745) to construct fluorescent reporter plasmids pOSV00170, pOSV00455 and pOSV00456, respectively. The fluorescent reporter was introduced at the ycgO locus by the selection of 5 μg/mL chloramphenicol (MilliporeSigma). The null DNA detection plasmid pOSV00157 was composed of Repressor lacI and IPTG-inducible toxin-antitoxin system $P_{hyperspank}$-txpA-ratA and can be introduced at the amyE locus by the selection of 100 μg/mL spectinomycin (Dot Scientific). The toxin-antitoxin system txpA-ratA was PCR amplified from *B. subtilis* 168 gDNA.

TABLE 1

List of plasmids.

| Plasmid | Description | Genotype |
|---|---|---|
| pAX01-comK[17] | Xylose-inducible comK | lacA(up), erm, $P_{xylA}$-comK, xylR, lacA(down) |
| pOSV00170 | GFP reporter | ycgO(up), cat, $P_{hyperspank}$-gfp, ycgO(down) |
| pOSV00455 | RFP reporter | ycgO(up), cat, $P_{hyperspank}$-rfp, ycgO(down) |
| pOSV00456 | BFP reporter | ycgO(up), cat, $P_{hyperspank}$-bfp, ycgO(down) |
| pOSV00157 | Detection plasmid without target sequence | amyE(up), lacI, $P_{hyperspank}$-txpA-ratA, spec, amyE(down) |
| pOSV00169 | Detection plasmid with 500 bp EC homology | amyE(up), 0.5 kbp EC(up), lacI, $P_{hyperspank}$-txpA-ratA, 0.5 kbp EC(down), spec, amyE(down) |
| pOSV00205 | Detection plasmid with 1000 bp EC homology | amyE(up), 1 kbp EC(up), lacI, $P_{hyperspank}$-txpA-ratA, 1 kbp EC(down), spec, amyE(down) |
| pOSV00206 | Detection plasmid with 1500 bp EC homology | amyE(up), 1.5 kbp EC(up), lacI, $P_{hyperspank}$-txpA-ratA, 1.5 kbp EC(down), spec, amyE(down) |
| pOSV00207 | Detection plasmid with 2000 bp EC homology | amyE(up), 2 kbp EC(up), lacI, $P_{hyperspank}$-txpA-ratA, 2 kbp EC(down), spec, amyE(down) |
| pOSV00208 | Detection plasmid with 2500 bp EC homology | amyE(up), 2.5 kbp EC(up), lacI, $P_{hyperspank}$-txpA-ratA, 2.5 kbp EC(down), spec, amyE(down) |
| pOSV00292 | Detection plasmid with 2500 bp ST homology | amyE(up), 2.5 kbp ST(up), lacI, $P_{hyperspank}$-txpA-ratA, 2.5 kbp ST(down), spec, amyE(down) |
| pOSV00459 | Detection plasmid with 2500 bp SA homology | amyE(up), 2.5 kbp SA(up), lacI, $P_{hyperspank}$-txpA-ratA, 2.5 kbp SA(down), spec, amyE(down) |
| pOSV00475 | Detection plasmid with 2500 bp CD homology | amyE(up), 2.5 kbp CD(up), lacI, $P_{hyperspank}$-txpA-ratA, 2.5 kbp CD(down), spec, amyE(down) |

*B. subtilis, E. coli, S. typhimurium, S. aureus* and *S. epidermidis* were all cultured at 37° C. in Lennox LB medium (Millipore Sigma). *C. difficile* and gut bacterial strains *A. caccae, B. thetaiotaomicron, C. asparagiforme, C. hiranonis*, and *B. longum* were cultured at 37° C. in YBMT medium in an anaerobic chamber (Coy Laboratory). YBHI medium is Brain-Heart Infusion Medium (Acumedia Lab) supplemented with 0.500 Bacto Yeast Extract (Thermo Fisher Scientific), 1 mg/mL D-Cellobiose (MilliporeSigma), 1 mg/mL D-maltose (MilliporeSigma), and 0.5 mg/mL L-cysteine (Millipore Sigma). The gDNA of each species was extracted using DNeasy Blood & Tissue Kit (Qiagen).

For *S. aureus* gDNA extraction, 0.1 mg/mL Lysostaphin (MilliporeSigma) was added in the pre-treatment step in combination with enzymatic lysis buffer (Qiagen). Bacterial strains are listed in Table 2.

TABLE 2

List of bacterial strains.

| Strain | Description | Genotype |
|---|---|---|
| msOSV00487 | EC-sensor with 500 bp homology | *B. subtilis* PY79 amyE::0.5 kbp EC(up), lacI, $P_{hyperspank}$-txpA-ratA, 0.5 kbp EC(down), spec; ycgO::cat, $P_{hyperspank}$-gfp; lacA::erm, $P_{xylA}$-comK, xylR |
| mOSV00580 | EC-sensor with 1000 bp homology | *B. subtilis* PY79 amyE::1 kbp EC(up), lacI, $P_{hyperspank}$-txpA-ratA, 1 kbp EC(down), spec; ycgO::cat, $P_{hyperspank}$-gfp; lacA::erm, $P_{xylA}$-comK, xylR |
| mOSV00581 | EC-sensor with 1500 bp homology | *B. subtilis* PY79 amyE::1.5 kbp EC(up), lacI, $P_{hyperspank}$-txpA-ratA, 1.5 kbp EC(down), spec; ycgO::cat, $P_{hyperspank}$-gfp; lacA::erm, PxylA-comK, xylR |
| mOSV00582 | EC-sensor with 2000 bp homology | *B. subtilis* PY79 amyE::2 kbp EC(up), lacI, $P_{hyperspank}$-txpA-ratA, 2 kbp EC(down), spec; ycgO::cat, $P_{hyperspank}$-gfp; lacA::erm, $P_{xylA}$-comK, xylR |
| msOSV00495 | EC-sensor (EC-G sensor) with 2500 bp homology | *B. subtilis* PY79 amyE::2.5 kbp EC(up), lacI, $P_{hyperspank}$-txpA-ratA, 2.5 kbp EC(down), spec; ycgO::cat, $P_{hyperspank}$-gfp; lacA::erm, $P_{xylA}$-comK, xylR |
| msOSV00605 | ST sensor | *B. subtilis* PY79 amyE::2.5 kbp ST(up), lacI, $P_{hyperspank}$-txpA-ratA, 2.5 kbp ST(down), spec; ycgO::cat, $P_{hyperspank}$-gfp; lacA::erm, $P_{xylA}$-comK, xylR |
| msOSV00906 | SA sensor | *B. subtilis* PY79 amyE::2.5 kbp SA(up), lacI, $P_{hyperspank}$-txpA-ratA, 2.5 kbp SA(down), spec; ycgO::cat, $P_{hyperspank}$-gfp; lacA::erm, $P_{xylA}$-comK, xylR |
| msOSV01005 | CD sensor | *B. subtilis* PY79 amyE::2.5 kbp CD(up), lacI, $P_{hyperspank}$-txpA-ratA, 2.5 kbp CD(down), spec; ycgO::cat, $P_{hyperspank}$-gfp; lacA::erm, $P_{xylA}$-comK, xylR |
| msOSV01009 | ST-R sensor | *B. subtilis* PY79 amyE::2.5 kbp ST(up), lacI, $P_{hyperspank}$-txpA-ratA, 2.5 kbp ST(down), spec; ycgO::cat, $P_{hyperspank}$-rfp; lacA::erm, $P_{xylA}$-comK, xylR |
| msOSV01008 | SA-B sensor | *B. subtilis* PY79 amyE::2.5 kbp SA(up), lacI, $P_{hyperspank}$-txpA-ratA, 2.5 kbp SA(down), spec; ycgO::cat, $P_{hyperspank}$-bfp; lacA::erm, $P_{xylA}$-comK, xylR |
| usOSV00264 | *Escherichia coli* MG1655 | |
| usOSV00197 | *Salmonella enterica* serovar Typhimurium LT2 ATCC 700720 | |
| usOSV00113 | *Staphylococcus aureus* DSM 2569 | |
| usOSV00095 | *Clostridium difficile* DSM 27147 | |
| usOSV00165 | *Staphylococcus epidermidis* ATCC 14990 | |
| usOSV00046 | *Clostridium hiranonis* DSM 13275 | |
| usOSV00157 | *Anaerostipes caccae* DSMZ 14662 | |
| usOSV00011 | *Bacteroides thetaiotaomicron* ATCC 29148 | |
| usOSV00041 | *Clostridium asparagiforme* DSM 15981 | |
| usOSV00067 | *Bifidobacterium longum* subs. *infantis* DSM 20088 | |

The target sequences xdhABC were PCR amplified from *E. coli* MG1655 gDNA (NCBI Reference Sequence: NC_000913.3; Location: 3001505-3004004 and 3004005-3006504), sipBCDA from *Salmonella enterica* serovar *Typhimurium* LT2 ATCC 700720 (NCBI Reference Sequence: NC_003197.2; Location: 3025979-3028478 and 3028479-3030978), hemEH from *S. aureus* DSM 2569 (GenBank: LHUS02000002.1; Location: 553-2770 and 2864-5638), and pheST from *C. difficile* DSM 27147 (GenBank: FN545816.1; Location: 770923-773144 and 773157-775686) to construct a set of plasmids (pOSV00169, pOSV00205, pOSV00206, pOSV00207, pOS00208, pOSV00292, pOSV00459 and pOSV00475) using restriction enzymes BamHI-HF (New England Biolabs) and EcoRI-HF (New England Biolabs) or Golden Gate Assembly Mix (New England Biolabs). DNA sequences of genetic parts are listed in Table 3.

TABLE 3

Sequences of genetic parts.

| Part | Sequence |
|---|---|
| $P_{hyperspank}$-txpA-ratA | ctcgagggtaaatgtgagcactcacaattcattttgcaaaagttgttgactttatctacaaggtgtggcataatgt<br>gtgtaattgtgagcggataacaattaagcttacataaggaggaactactATGTCGACCTATGAA<br>TCTCTAATGGTCATGATCGGCTTTGCCAATTTAATAGGCGGGATT<br>ATGACATGGGTAATATCTCTTTTAACATTATTATTCATGCTTAGAA<br>AAAAAGACACTCATCCTATTTACATTACTGTAAAGGAAAAGTGTC<br>TACACGAGGACCCTCCTATTAAAGGGTAGTTTCTTTTTTAAAAGCT<br>AGAGTGCTGCCACACTCTGGCTTTTATATTTTAGCATTTCTCATGA<br>AAGTAACACACATTAACAAGTGGTAATGTGGTAATGTGGTACCAA<br>CTATAAGCTTACGCCAGTAGTTGCAATACTTTTGCTTGGCACCATT<br>ATAACATGAATATATATTGATTATATAATTATTTGTATCTTTTATT<br>TGTTACTTTTTTTATCTATGAGTTCAAAATGACCTGATCATAGAAG<br>CCTTAACCCTTTTTCTTTTATTAAAAACCCTCGGATTATGAAAGTG<br>TTATGGTACAATATGGTTTAGTATAAATGAATATTGGCTTTCAAC<br>ATCTCAAGGGCGGTCTGGCTCACTCCCTCATGAAAGGGGGTGATG<br>CACGTGTCAACATTTCAAGCATTAATGCTTATGCTTGCTTTCGGGT<br>CATTTATAATTGCCCTGTTGACTTATATAAAGAAGAAATAGACCC<br>ACCCCTTGAGCTCGGCAAAGTAAAAGGGTAA (SEQ ID NO: 5) |
| gfp(Sp) | ATGGTTTCTAAAGGTGAAGAATTGTTTACAGGTGTTGTTCCAATTT<br>TGGTTGAATTGGATGGTGATGTTAATGGTCATAAATTTTCTGTTTC<br>TGGTGAAGGTGAAGGTGATGCTACATACGGTAAATTGACATTGAA<br>ATTTATTTGTACAACTGGTAAATTGCCAGTTCCTTGGCCAACATTG<br>GTTACAACATTTGCTTATGGTTTGCAATGTTTTGCTCGTTATCCAG<br>ATCACATGAAACAACATGATTTCTTTAAATCTGCTATGCCAGAAG<br>GTTATGTTCAAGAACGTACAATCTTTTTCAAGGATGATGGTAATT<br>ATAAGACACGTGCTGAGGTTAAGTTTGAAGGTGATACATTGGTTA<br>ATCGTATCGAATTGAAGGGTATCGATTTTAAAGAAGATGGTAATA<br>TCTTGGGTCATAAATTGGAATATAATTATAATTCTCATAATGTTTA<br>TATCATGGCTGATAAACAAAAGAACGGTATTAAAGTTAATTTTAA<br>AATTCGTCATAATATTGAAGATGGTTCTGTTCAATTGGCTGATCAT<br>TATCAACAAAATACACCAATTGGTGATGGTCCAGTTTTGTTGCCA<br>GATAATCATTATTTGTCTACACAATCTAAATTGTCTAAAGATCCA<br>AATGAAAAACGTGATCACATGGTTTTGTTGGAATTTGTTACAGCT<br>GCTGGTATTACACATGGTATGGATGAATTGTATAAATAA (SEQ ID<br>NO: 6) |
| rmCherry | ATGGTTAGCAAAGGCGAAGAGGATAATATGGCGATCATCAAAGA<br>ATTTATGCGCTTTAAAGTTCATATGGAAGGCAGCGTTAATGGCCA<br>CGAATTTGAAATTGAAGGCGAAGGTGAAGGCAGACCGTATGAAG<br>GCACACAAACAGCAAAACTGAAAGTTACAAAAGGCGGACCGCTG<br>CCGTTTGCATGGGATATTCTGTCACCGCAATTTATGTATGGCAGC<br>AAAGCATATGTTAAACATCCGGCAGATATCCCGGATTATCTGAAA<br>CTGTCATTTCCGGAAGGCTTTAAATGGGAACGCGTCATGAATTTT<br>GAAGATGGCGGAGTTGTTACAGTCACACAAGATTCATCACTGCAA<br>GATGGCGAATTTATCTATAAAGTCAAACTGCGTGGCACGAACTTT<br>CCGTCAGATGGCCCTGTTATGCAGAAAAAAACAATGGGCTGGGA<br>AGCATCAAGCGAAAGAATGTATCCGGAAGATGGTGCACTGAAAG<br>GCGAAATTAAACAACGCCTGAAACTTAAAGACGGTGGACATTAT<br>GATGCGGAAGTCAAAACAACGTATAAAGCGAAAAAACCTGTTCA<br>ACTGCCTGGCGCATATAACGTTAACATTAAACTGGATATCACGAG<br>CCATAACGAAGATTATACAATCGTCGAACAGTATGAAAGAGCAG<br>AAGGACGCCATTCAACAGGCGGAATGGATGAACTGTATAAATAC<br>TAG (SEQ ID NO: 7) |
| mTagBFP | ATGAGCGAACTGATCAAAGAAAACATGCATATGAAACTGTACAT<br>GGAAGGCACAGTCGATAACCATCACTTTAAATGCACATCAGAAG<br>GCGAAGGCAAACCGTATGAAGGCACACAAACAATGAGAATCAAA<br>GTTGTTGAAGGCGGACCGCTGCCGTTTGCATTTGATATTCTGGCA<br>ACATCATTTCTGTATGGCAGCAAAACGTTTATCAATCATACACAA<br>GGCATCCCGGATTTTTTTAAACAATCATTTCCGGAAGGCTTTACAT<br>GGGAACGCGTTACAACATATGAAGATGGCGGAGTTCTGACAGCA<br>ACACAAGATACATCATTGCAAGATGGCTGCCTGATCTATAATGTC<br>AAAATTAGAGGCGTCAACTTTACAAGCAATGGCCCTGTTATGCAG<br>AAAAAAACACTGGGCTGGGAAGCATTTACAGAAACACTGTATCC |

TABLE 3-continued

Sequences of genetic parts.

| Part | Sequence |
| --- | --- |
| | GGCTGATGGCGGACTGGAAGGCAGAAACGATATGGCACTGAAAC<br>TGGTTGGCGGATCACATCTGATTGCAAACATCAAAACAACGTACC<br>GCTCAAAAAAACCGGCAAAAAATCTGAAAATGCCTGGCGTCTATT<br>ATGTCGATTATAGACTGGAACGCATCAAAGAAGCGAACAACGAA<br>ACATATGTCGAACAACATGAAGTTGCAGTTGCGAGATATTGCGAT<br>CTGCCGTCAAAACTGGGCCATAAACTGAATTACTAG (SEQ ID<br>NO: 8) |
| EC(up) 0.5 kbp | Caattaccatcgaatgcaccattaacgggatgccttttcagcttcacgccgcaccaggcacgccgctctcgg<br>aattactccgcgaacaaggactgctaagtgtcaaacaagggtgctgcgtgggtgaatgtggtgcctgtacggt<br>gttggtcgacggcacagcaatagacagttgcttataccttgccgcctgggctgaaggaaaagagatccgcac<br>gctggaaggtgaagcgaaaggcggaaaactttctcatgttcagcaggcttatgcgaaatccggcgcagtgca<br>gtgcgggttttgtacgcctggcctgattatggctaccacggcaatgctggcgaaaccacgcgagaagccatt<br>aaccattacggaaattcgtcgcggactggcgggaaatctttgtcgctgcacggggtatcagatgattgtaaata<br>cagttctggattgcgagaaaacgaagtaa (SEQ ID NO: 9) |
| EC(down) 0.5 kbp | Ttatgtgtttaacaactcatatttcttaatcttgcgatagagcgtagcaatgccgatgcccagttcatcagcaactt<br>gcttcttgctgttatgacgtgaaagcgcctcgcggatcatttgcttttccatctcctccagcgccgtgccgcccg<br>catcatcgagtgacaggtgcgcctcactgacctctgttacatcactttgctccgttgtgccattattcagcagattt<br>ggcggcaatagcgtgctgtcgataacttcacctgaaggaaccacgttaaccagatattccatcaaattgcttaa<br>ctcgcgcaggtttccgggccaacgatgcttacgcaatatttcgacgacatcgggagcaatgccaggataaac<br>cgatcccagacgacgggtatgcagatgtaaaaagtaatgcaccaatagttcaatatcttcctgacgttcacgca<br>gcggtggcagagttatcgggataacattaagtcggtagaagagatctt (SEQ ID NO: 10) |
| EC(up) 1 kbp | Atgacgcgaaactggagatccactccccgcgcggtgttcgtttcgtcccgattaatggctttcacaccgggcc<br>gggcaaagtgtctcttgagcatgacgaaatcctcgtcgcctttcatttccgccacagccgaaagaacacgcg<br>ggcagcgcgcattttaaatatgccatgcgcgacgcaatggatatttcaacgattggctgcgccgcacattgcc<br>gactggataacggcaatttcagcgaattacgcctggcatttggtgttgccgcgccaacgccgattcgctgcca<br>acatgccgaacagactgcacaaaatgcgccattaaacctgcaaacgctggaagctatcagcgaatctgtcct<br>gcaagatgtcgccccgcgttcttcatggcgggccagtaaagagtttcgtctgcatctcatccagacgatgacc<br>aaaaaagtgattagcgaagccgtcgccgcgggggggaaaattgcaatgaatcacagcgaaacaattac<br>catcgaatgcaccattaacgggatgccttttcagcttcacgccgcaccaggcacgccgctctcggaattactc<br>cgcgaacaaggactgctaagtgtcaaacaagggtgctgcgtgggtgaatgtggtgcctgtacggtgttggtc<br>gacggcacagcaatagacagttgcttataccttgccgcctgggctgaaggaaaagagatccgcacgctgga<br>aggtgaagcgaaaggcggaaaactttctcatgttcagcaggcttatgcgaaatccggcgcagtgcagtgcg<br>ggttttgtacgcctggcctgattatggctaccacggcaatgctggcgaaaccacgcgagaagccattaaccat<br>tacggaaattcgtcgcggactggcgggaaatctttgtcgctgcacggggtatcagatgattgtaaatacagttc<br>tggattgcgagaaaacgaagtaaaaggatatccggcctgaattcaggccggattcactg (SEQ ID<br>NO: 11) |
| EC(down) 1 kbp | Aggttatgtgtttaacaactcatatttcttaatcttgcgatagagcgtagcaatgccgatgcccagttcatcagca<br>acttgcttcttgctgttatgacgtgaaagcgcctcgcggatcatttgcttttccatctcctccagcgccgtgccgc<br>ccgcatcatcgagtgacaggtgcgcctcactgacctctgttacatcactttgctccgttgtgccattattcagca<br>gatttggcggcaatagcgtgctgtcgataacttcacctgaaggaaccacgttaaccagatattccatcaaattg<br>cttaactcgcgcaggtttccgggccaacgatgcttacgcaatatttcgacgacatcgggagcaatgccaggat<br>aaaccgatcccagacgacgggtatgcagatgtaaaaagtaatgcaccaatagttcaatatcttcctgacgttca<br>cgcagcggtggcagagttatcgggataacattaagtcggtagaagagatcttcgcggaatttaccttcggcaa<br>tgaactgggccaaattctgattagttgcagaaatgatgcgaatgtcgacttgtattgggctactggcaccaatcg<br>gcagaatttcacgtgcctcaatagcgcgcagtaatttagcctgcaacattaatggcatatcacctatttcatcga<br>gaaacagcgtgcccgtattcgccgcctgaatcaaccctgttttaccgttggcagaagcgccagtaaatgcacc<br>tttaacataaccgaacagttcgctctccagaagctgctccggaatcgcggcacagttgatagcaataaagggt<br>ttattccgtcttccgctcaacttatggattgcacgggcgacgacttctttacccgtgccgctttcaccaaccacca<br>taacgctggatgggctgggtgcaatacggctaatgagtcgttttaattgccgcataacacggcactcgccaac<br>caattgttcaatatgcggttcatcaggtgcattt (SEQ ID NO: 12) |
| EC(up) 1.5 kbp | cgtaacgcggtgaagatggctaccggtgttgcaatcaatacactgccgctgacgccaaaacggttatatgaa<br>gagttccatctggcaggattgatttgaggataacatcatgtttgattttgcttcttaccatcgcgcagcaaccctt<br>gccgatgccatcaacctgctggctgacaacccgcaggccaaactgctcgccggtggcactgacgtactgattc<br>agctccaccatcacaatgaccgttatcgccatattgttgatattcataatctggcggagctgcggggaattacgc<br>tggcggaagatggctcgctacgtatcggctctgcaacgacatttacccagctaatagaagatcctataactcaa<br>cgtcatctcccggcgttatgtgctgcggccacgtccattgctggaccgcagatccgtaacgtcgctacctacg<br>gtggaaatatttgcaacggtgccaccagcgcagattctgccacgccaacgctaatttatgacgcgaaactgga<br>gatccactccccgcgcggtgttcgtttcgtcccgattaatggctttcacaccgggccgggcaaagtgtctcttg<br>agcatgacgaaatcctcgtcgcctttcatttccgccacagccgaaagaacacgcgggcagcgcgcattttaa<br>atatgccatgcgcgacgcaatggatatttcaacgattggctgcgccgcacattgccgactggataacggcaat<br>ttcagcgaattacgcctggcatttggtgttgccgcgccaacgccgattcgctgccaacatgccgaacagactg<br>cacaaaatgcgccattaaacctgcaaacgctggaagctatcagcgaatctgtcctgcaagatgtcgccccgc<br>gttcttcatggcgggccagtaaagagtttcgtctgcatctcatccagacgatgaccaaaaaagtgattagcgaa<br>gccgtcgccgcgggggggaaaattgcaatgaatcacagcgaaacaattaccatcgaatgcaccattaac<br>gggatgccttttcagcttcacgccgcaccaggcacgccgctctcggaattactccgcgaacaaggactgcta<br>agtgtcaaacaagggtgctgcgtgggtgaatgtggtgcctgtacggtgttggtcgacggcacagcaatagac<br>agttgcttataccttgccgcctgggctgaaggaaaagagatccgcacgctggaaggtgaagcgaaaggcgg<br>aaaactttctcatgttcagcaggcttatgcgaaatccggcgcagtgcagtgcgggttttgtacgcctggcctga<br>ttatggctaccacggcaatgctggcgaaaccacgcgagaagccattaaccattacggaaattcgtcgcggac<br>tggcgggaaatctttgtcgctgcacggggtatcagatgattgtaaatacagttctggattgcgagaaaacgaa<br>gtaaaaggatatccggcctgaattcaggccggattcactg (SEQ ID NO: 13) |

TABLE 3-continued

Sequences of genetic parts.

| Part | Sequence |
|---|---|
| EC(down) 1.5 kbp | aggttatgtgtttaacaactcatatttcttaatcttgcgatagagcgtagcaatgccgatgcccagttcatcagca<br>acttgcttcttgctgttatgacgtgaaagcgcctcgcggatcatttgcttttccatctcctccagcgccgtgccgc<br>ccgcatcatcgagtgacaggtgcgcctcactgacctctgttacatcactttgctccgttgtgccattattcagca<br>gatttggcggcaatagcgtgctgtcgataacttcacctgaaggaaccacgttaaccagatattccatcaaattg<br>cttaactcgcgcaggtttccgggccaacgatgcttacgcaatatttcgacgacatcgggagcaatgccaggat<br>aaaccgatcccagacgacgggtatgcagatgtaaaaagtaatgcaccaatagttcaatatcttcctgacgttca<br>cgcagcggtggcagagttatcgggataacattaagtcggtagaagagatcttcgcggaatttaccttcggcaa<br>tgaactgggccaaattctgattagttgcagaaatgatgcgaatgtcgacttgtattgggctactggcaccaatcg<br>gcagaatttcacgtgcctcaatagcgcgcagtaatttagcctgcaacattaatggcatatcacctatttcatcga<br>gaaacagcgtgcccgtattcgccgcctgaatcaaccctgttttaccgttggcagaagcgccagtaaatgcacc<br>tttaacataaccgaacagttcgctctccagaagctgctccggaatcgcggcacagttgatagcaataaagggt<br>ttattccgtcttccgctcaacttatggattgcacgggcgacgacttctttacccgtgccgctttcaccaaccacca<br>taacgctggatgggctgggtgcaatacggctaatgagtcgttttaattgccgcataacacggcactcgccaac<br>caattgttcaatatgcggttcatcaggtgcatttgctacagaaaaactggtatgcgattggtgaaacgccattaa<br>aaataattgtcggccctgaatgttatgcaattgaccaatgattaattcacttttatcgtcccatgaaacaatatgct<br>gcatatgtccatgggtaaaattactctcaaatgttaatggtctgaaacggataggtttcccaataatattattttgc<br>acaacaccaagtgtttttaaggcagtctgattaacaaactgaacccgattttcatcatctacaactaatacgccctg<br>atccatattatcgatcatggtcgcaaatattttactgatgttatctcctggcccctgatcctccagaagtttcgaaa<br>caaaaatggtggatatatggcgaacataatcagaaaattcgcgtaaattatcactgatatgctcttgttgctcgtg<br>ggtaacggcaatcaaacttatcaccccaacacaacgatcctgtaaaatgacaggcgtacccagaaatgcttttt<br>c (SEQ ID NO: 14) |
| EC(up) 2 kbp | ccctgataaaaggccatatcgtgctggttgaacgaccggaagagccgttaatgtcgttaaaagatttggcgat<br>ggacgctttctaccaccctgaacgcggcgggcagctctctgctgaaagctccatcaaaaccaccactaaccc<br>accggcgtttggctgtacctttgttgatctgacggtcgatattgcgctgtgcaaagtcaccatcaaccgcatcct<br>caacgttcatgattcagggcatattcttaatccactgctggcagaaggtcaggtacacggcggaatgggaatg<br>ggcattggctgggcgctatttgaagagatgatcatcgatgctaaaagcggcgtggtccgtaaccccaatctgc<br>tggattacaaaatgccgaccatgccggatctgccacaactggaaagcgcgttcgtcgaaatcaatgagccgc<br>aatccgcatacggacataagtcactgggtgagccaccaataattcctgttgccgctgctattcgtaacgcggtg<br>aagatggctaccggtgttgcaatcaatacactgccgctgacgccaaaacggttatatgaagagttccatctgg<br>caggattgatttgaggataacatcatgtttgattttgcttcttaccatcgcgcagcaacccttgccgatgccatca<br>acctgctggctgacaacccgcaggccaaactgctcgccggtggcactgacgtactgattcagctccaccatc<br>acaatgaccgttatcgccatattgttgatattcataatctggcggagctgcggggaattacgctggcggaagat<br>ggctcgctacgtatcggctctgcaacgacatttacccagctaatagaagatcctataactcaacgtcatctccc<br>ggcgttatgtgctgcggccacgtccattgctggaccgcagatccgtaacgtcgctacctacggtggaaatattt<br>gcaacggtgccaccagcgcagattctgccacgccaacgctaatttatgacgcgaaactggagatccactccc<br>cgcgcggtgttcgtttcgtcccgattaatggctttcacaccgggccgggcaaagtgtctcttgagcatgacgaa<br>atcctcgtcgcctttcattttccgccacagccgaaagaacacgcgggcagcgcgcattttaaatatgccatgcg<br>cgacgcaatggatatttcaacgattggctgcgccgcacattgccgactggataacggcaatttcagcgaatta<br>cgcctggcatttggtgttgccgcgccaacgccgattcgctgccaacatgccgaacagactgcacaaaatgcg<br>ccattaaacctgcaaacgctggaagctatcagcgaatctgtcctgcaagatgtcgccccgcgttcttcatggc<br>gggccagtaaagagtttcgtctgcatctcatccagacgatgaccaaaaaagtgattagcgaagccgtcgccg<br>cggcgggggaaaattgcaatgaatcacagcgaaacaattaccatcgaatgcaccattaacgggatgccttttt<br>cagcttcacgccgcaccaggcacgccgctctcggaattactccgcgaacaaggactgctaagtgtcaaaca<br>agggtgctgcgtgggtgaatgtggtgcctgtacggtgttggtcgacggcacagcaatagacagttgcttatac<br>cttgccgcctgggctgaaggaaaagagatccgcacgctggaaggtgaagcgaaaggcggaaaactttctc<br>atgttcagcaggcttatgcgaaatccggcgcagtgcagtgcgggttttgtacgcctggcctgattatggctacc<br>acggcaatgctggcgaaaccacgcgagaagccattaaccattacggaaattcgtcgcggactggcgggaa<br>atctttgtcgctgcacggggtatcagatgattgtaaatacagttctggattgcgagaaaacgaagtaaaaggat<br>atccggcctgaattcaggccggattcactg (SEQ ID NO: 15) |
| EC(down) 2 kbp | aggttatgtgtttaacaactcatatttcttaatcttgcgatagagcgtagcaatgccgatgcccagttcatcagca<br>acttgcttcttgctgttatgacgtgaaagcgcctcgcggatcatttgcttttccatctcctccagcgccgtgccgc<br>ccgcatcatcgagtgacaggtgcgcctcactgacctctgttacatcactttgctccgttgtgccattattcagca<br>gatttggcggcaatagcgtgctgtcgataacttcacctgaaggaaccacgttaaccagatattccatcaaattg<br>cttaactcgcgcaggtttccgggccaacgatgcttacgcaatatttcgacgacatcgggagcaatgccaggat<br>aaaccgatcccagacgacgggtatgcagatgtaaaaagtaatgcaccaatagttcaatatcttcctgacgttca<br>cgcagcggtggcagagttatcgggataacattaagtcggtagaagagatcttcgcggaatttaccttcggcaa<br>tgaactgggccaaattctgattagttgcagaaatgatgcgaatgtcgacttgtattgggctactggcaccaatcg<br>gcagaatttcacgtgcctcaatagcgcgcagtaatttagcctgcaacattaatggcatatcacctatttcatcga<br>gaaacagcgtgcccgtattcgccgcctgaatcaaccctgttttaccgttggcagaagcgccagtaaatgcacc<br>tttaacataaccgaacagttcgctctccagaagctgctccggaatcgcggcacagttgatagcaataaagggt<br>ttattccgtcttccgctcaacttatggattgcacgggcgacgacttctttacccgtgccgctttcaccaaccacca<br>taacgctggatgggctgggtgcaatacggctaatgagtcgttttaattgccgcataacacggcactcgccaac<br>caattgttcaatatgcggttcatcaggtgcatttgctacagaaaaactggtatgcgattggtgaaacgccattaa<br>aaataattgtcggccctgaatgttatgcaattgaccaatgattaattcacttttatcgtcccatgaaacaatatgct<br>gcatatgtccatgggtaaaattactctcaaatgttaatggtctgaaacggataggtttcccaataatattattttgc<br>acaacaccaagtgtttttaaggcagtctgattaacaaactgaacccgattttcatcatctacaactaatacgccctg<br>atccatattatcgatcatggtcgcaaatattttactgatgttatctcctggcccctgatcctccagaagtttcgaaa<br>caaaaatggtggatatatggcgaacataatcagaaaattcgcgtaaattatcactgatatgctcttgttgctcgtg<br>ggtaacggcaatcaaacttatcaccccaacacaacgatcctgtaaaatgacaggcgtacccagaaatgcttttt<br>cgcggcaatttctttactatcgcaaccttcgcaaaggggatcgaagcgagactgtgtcacaactttttcagtttt<br>cgtttccaggacgtggcggagcaggcgtgagttgccgctcaactggcgaccaagaaacttcccatacgcgc<br>ccgttccggcaacgcgacacaagttttcatcaacgatctcaacctcaagctgcaaaacgctggcaagcattct<br>ggcaaaacgctgaattgtcggttgaatttgcatcaatactgactgcgtagtagcaagctccatagctttaccttc |

TABLE 3-continued

Sequences of genetic parts.

| Part | Sequence |
| --- | --- |
| | cagacttacttaaaagtcgatcattgaagacgttgatggttcacagatcatgatgatattaactcaggcgaaatt<br>ggctttgataaaaacataagattttatcattttctaatgaaattatggaagagatatcacatttctatatcaatat<br>gagaattacggcggtgagtttatcaaactgaagagagatagcctgcccctttat (SEQ ID NO: 16) |
| EC(up) 2.5 kbp | aggagatgctaatccgctcacgggcaaacgtatttacagcgcagggttgccggagtgtcttgaaaaaggccg<br>gaaaatctttgaatgggaaaaacgccgtgcagaatgccagaaccagcaaggcaatttgcgccgcggcgttg<br>gcgtcgcctgttttagctacacctctaacacctggcctgtcggcgtagaaatagcaggcgcgcgccttctgat<br>gaatcaggatggaaccatcaacgtgcaaagcggcgcgacggaaatcggtcagggtgccgacaccgtcttct<br>cgcaaatggtggcagaaaccgtggggggttccggtcagcgacgttcgcgttatttcaactcaagataccgacg<br>ttacgccgttcgatcccggcgcatttgcctcacgccagagctatgttgccgcgcctgcgctgcgcagtgcgg<br>cactattattaaaagagaaaatcatcgctcacgccgcagtcatgctacatcagtcagcgatgaatctgaccctg<br>ataaaaggccatatcgtgctggttgaacgaccggaagagccgttaatgtcgttaaaagatttggcgatggacg<br>ctttctaccaccctgaacgcgggggcagctctctgctgaaagctccatcaaaaccaccactaacccaccgg<br>cgtttggctgtacctttgttgatctgacggtcgatattgcgctgtgcaaagtcaccatcaaccgcatcctcaacgt<br>tcatgattcagggcatattcttaatccactgctggcagaaggtcaggtacacggcggaatgggaatgggcatt<br>ggctgggcgctatttgaagagatgatcatcgatgctaaaagcggcgtggtccgtaaccccaatctgctggatt<br>acaaaatgccgaccatgccggatctgccacaactggaaagcgcgttcgtcgaaatcaatgagccgcaatcc<br>gcatacggacataagtcactgggtgagccaccaataattcctgttgccgctgctattcgtaacgcggtgaagat<br>ggctaccggtgttgcaatcaatacactgccgctgacgccaaaacggttatatgaagagttccatctggcagga<br>ttgatttgaggataacatcatgtttgattttgcttcttaccatcgcgcagcaacccttgccgatgccatcaacctgc<br>tggctgacaacccgcaggccaaactgctcgccggtggcactgacgtactgattcagctccaccatcacaatg<br>accgttatcgccatattgttgatattcataatctggcggagctgcggggaattacgctggcggaagatggctcg<br>ctacgtatcggctctgcaacgacatttacccagctaatagaagatcctataactcaacgtcatctcccggcgtta<br>tgtgctgcggccacgtccattgctggaccgcagatccgtaacgtcgctacctacggtggaaatatttgcaacg<br>gtgccaccagcgcagattctgccacgccaacgctaatttatgacgcgaaactggagatccactccccgcgcg<br>gtgttcgtttcgtcccgattaatggctttcacaccgggccgggcaaagtgtctcttgagcatgacgaaatcctcg<br>tcgcctttcattttccgccacagccgaaagaacacggggcagcgcgcattttaaatatgccatgcgcgacgc<br>aatggatatttcaacgattggctgcgccgcacattgccgactggataacggcaatttcagcgaattacgcctgg<br>catttggtgttgccgcgccaacgccgattcgctgccaacatgccgaacagactgcacaaaatgcgccattaa<br>acctgcaaacgctggaagctatcagcgaatctgtcctgcaagatgtcgccccgcgttcttcatggcgggcca<br>gtaaagagtttcgtctgcatctcatccagacgatgaccaaaaaagtgattagcgaagccgtcgccgcggcgg<br>ggggaaaattgcaatgaatcacagcgaaacaattaccatcgaatgcaccattaacgggatgccttttcagcttc<br>acgccgcaccaggcacgccgctctcggaattactccgcgaacaaggactgctaagtgtcaaacaagggtgc<br>tgcgtgggtgaatgtggtgcctgtacggtgttggtcgacggcacagcaatagacagttgcttataccttgccgc<br>ctgggctgaaggaaaagagatccgcacgctggaaggtgaagcgaaaggcggaaaactttctcatgttcagc<br>aggcttatgcgaaatccggcgcagtgcagtgcgggttttgtacgcctggcctgattatggctaccacggcaat<br>gctggcgaaaccacgcgagaagccattaaccattacggaaattcgtcgcggactgggggaaatctttgtcg<br>ctgcacggggtatcagatgattgtaaatacagttctggattgcgagaaaacgaagtaaaaggatatccggcct<br>gaattcaggccggattcactg (SEQ ID NO: 17) |
| EC(down) 2.5 kbp | aggttatgtgtttaacaactcatatttcttaatcttgcgatagagcgtagcaatgccgatgcccagttcatcagca<br>acttgcttcttgctgttatgacgtgaaagcgcctcgcggatcatttgcttttccatctcctccagcgccgtgccgc<br>ccgcatcatcgagtgacaggtgcgcctcactgacctctgttacatcactttgctccgttgtgccattattcagca<br>gatttggcggcaatagcgtgctgtcgataacttcacctgaaggaaccacgttaaccagatattccatcaaattg<br>cttaactcgcgcaggtttccgggccaacgatgcttacgcaatatttcgacgacatcgggagcaatgccaggat<br>aaaccgatcccagacgacgggtatgcagatgtaaaaagtaatgcaccaatagttcaatatcttcctgacgttca<br>cgcagcggtggcagagttatcgggataacattaagtcggtagaagagatcttcgcggaatttaccttcggcaa<br>tgaactgggccaaattctgattagttgcagaaatgatgcgaatgtcgacttgtattgggctactggcaccaatcg<br>gcagaatttcacgtgcctcaatagcgcgcagtaatttagcctgcaacattaatggcatatcacctatttcatcga<br>gaaacagcgtgcccgtattcgccgcctgaatcaaccctgttttaccgttggcagaagcgccagtaaatgcacc<br>tttaacataaccgaacagttcgctctccagaagctgctccggaatcgcggcacagttgatagcaataaagggt<br>ttattccgtcttccgctcaacttatggattgcacgggcgacgacttctttacccgtgccgctttcaccaaccacca<br>taacgctggatgggctgggtgcaatacggctaatgagtcgttttaattgccgcataacacggcactcgccaac<br>caattgttcaatatgcggttcatcaggtgcatttgctacagaaaaactggtatgcgattggtgaaacgccattaa<br>aaataattgtcggccctgaatgttatgcaattgaccaatgattaattcacttttatcgtcccatgaaacaatatgct<br>gcatatgtccatgggtaaaattactctcaaatgttaatggtctgaaacggataggtttcccaataatattatttgc<br>acaacaccaagtgtttttaaggcagtctgattaacaaactgaacccgattttcatcatctacaactaatacgccctg<br>atccatattatcgatcatggtcgcaaatattttactgatgttatctcctggcccctgatcctccagaagtttcgaaa<br>caaaaatggtggatatatggcgaacataatcagaaaattcgcgtaaattatcactgatatgctcttgttgctcgtg<br>ggtaacggcaatcaaacttatcaccccaacacaacgatcctgtaaaatgacaggcgtacccagaaatgcttttt<br>cgcggcaattttctttactatcgcaaccttcgcaaaggggatcgaagcgagactgtgtcacaactttttcagtttt<br>cgtttccaggacgtggcggagcaggcgtgagttgccgctcaactggcgaccaagaaacttcccatacgcgc<br>ccgttccggcaacgcgacacaagttttcatcaacgatctcaacctcaagctgcaaaacgctggcaagcattct<br>ggcaaaacgctgaattgtcggttgaatttgcatcaatactgactgcgtagtagcaagctccatagctttaccttc<br>cagacttacttaaaagtcgatcattgaagacgttgatggttcacagatcatgatgatattaactcaggcgaaatt<br>ggctttgataaaaacataagattttatcattttctaatgaaattatggaagagatatcacatttctatatcaatat<br>gagaattacggcggtgagtttatcaaactgaagagagatagcctgcccctttatcttatttctgatacttagcagca<br>aataaataacgcgataaaaaaagccaaacgttttcgtattttacaaacaaccagaagctggcatcaatttgtgatc<br>aaccccacacattatccgtcaaattagtcttttgcagccgcgcggataattctggcacacttattgttagtcccag<br>gtatagctgtgaaaacaccaatcactttggcaagtcacagtgaaataaaccactttgcctgtcattccactaccg<br>ggactttatgatgaaaactgttaatgagctgattaaggatatcaattcgctgacctctcaccttcacgagaaagat<br>tttttgttaacgtgggaacagacgccagatgaactgaaacaagtactggacgttgccgcagcattaaaagcac<br>tgcgtgctgaaaacatctcaaccaaagtctttaatagtggattaggtatttccgtattccgcgacaactccaccc<br>gtacccgcttctcttatgcttccgcg (SEQ ID NO: 18) |

TABLE 3-continued

Sequences of genetic parts.

| Part | Sequence |
| --- | --- |
| ST(up) 2.5 kbp | acgtagcagcaggggtatcaacgtttgcatttcaaggtgccgggcttcccgtcctacgctggtaccctgctctt gcgttaattttggtggcacatatcaagcgcctcaacagccttcgccgccgctttgtcaacaaggtgcgtaaga ttgctgcgggttaacggatctaacgtacagccaaagttatgttcaatgcagctggcaatatagggcatcacctc ctgcataacaagattcgtcgataatttacttaattcaccgccagtgttattttgataatatctaacagctgctttt ccaggttttccagcttcgcttccgctttctttgtttctggcagccatggcccaaaagctgactttctttcaggcca tcttttatgatttgcgcggtatactctgcccccaccttcatcagtagcgtcttcgcctcaggagaatcactggtggc gttgagcgctgaacgaaagagcccggcaaactccattatcgctttcttaccggcgacattatttgaattggtaaaaa cttcttttaacgcctcagcgtctttcccgcatttaaacaatgcatccagactcgcctgtttgatcagcgcgggaaa atcttccagttgcgggcctttaatttcccctgacagcgtcgctgtggcactttctctgactgcggaaagattcgcc gcaagattcgtggcctgcgttttgatctcggtctgcatacctggcattatgacgggggctgagtccttacactt gtaaccattattaatatcctcttctgttatccttgcaggaagctttggcggtttccaggctgctacttatcgtact gctcagcacttttaccaggttgtcgtacaatgaattggcattgctatatttttgcgtcagcgtctgtaatgtggttt tcatattttcttcctgcgctttaaaacccgactgccaggcttgatatttggcgttatccatttcgagttttgagtct tttcccggcgcgcctaaaccatcaatatcctgaaccatttttgtaatggcgtcagatcaacggtgacgacataacc ggatccataagatttcaggcagctattcggtaaattcaattcactgagccactgtctcgcttccgcttcagtggcta ctttaacgccgctgcctgactgcgctggaaataaaacggtattactgtttatttgattatatttattgactaaactg tttaaatcattttgagtgaggtaacatctagcttaacggtattaccgtccttacctggtaataaccagcctcccat tttggaaagaatatcactgaaggcctgataaaaatcggtatagactgcgacaacgttttcataaacgcccagatagc tgtcacctatcgccgatatattttgggaaaccatatcccaaatctcagcatcagaaatggttgttctcggctgcgc cataggcgaagcgctaaataaggccgacgtcggcgcagaaaacgcgctccgcaggttctcatttttgttctgc ggataatgacacgccggacttcgccagcgcattcaggctgctggtcaactgctggcgcgccagcgtgcgct cgtcattattctcttcagagatcggtggcgttgactgcagcgtctgctgtgcctggtggattttagtagccgcctg cgataatgaaatgatatctgtaccgcgatgttctgtggtagacggtaccacggcagtctcgacgtgctcgctcg ccgagggagtctgcggccgttcggcaacgatccccggatgaggagaagcggaataattttgaatattaagca taatatccccagttcgccatcaggagcgcgattaaatcacacccatgatggcgtatagatgacctttcagattaa gcgcgaatattgcctgcgatagcagcgagtgcggatgctttcgactggttaatgctctccattgttttcagcattt cctgaatcaggctggtcgatttacgtgaactttcacgggcttcgtccgatgcggtgctggcaacccggttattc acctggctaatttgctgctcggaacgttcctgagtagcggcgtactgcccggacgcccctgcaataccaccg accgtgaccgagttcttcataatcagatcgcccgtcatctgcatcttgcgcgcatcgattcgggtcatatccatg gtattctgctcaagacgaatatcggattcgacagactcaagacgtttcgacagaatagcctgatgttcaggga gatttgtttattactgtctttaatacccagactttccgtggcgctggttccggcattagatttaagcgtcgcatcat taagattttcgtcgcatcggtaccggttttcttcatatttaacgatttcagagaatcgacgccttcagcaccgagt ttgacgctattctgcccgttcagcacgtttttaatactgtggctttcagtggtcagtttatcgatcttcgcggcatt atgtttaag (SEQ ID NO: 19) |
| ST(down) 2.5 kbp | cgcgcctctttcattctgcagccccttatattccagtttggcgcccacgccagtgatccccaactgaagcgcgc tctgggaaatactaccggacaacgcattcatcccttcgcgcatcatggagcttgccgtcgttttagctgcatcaa aactgactaatgacaacttaccagacagtttgctatcagcctggttcaacgtcagcattaacgtattcgcggca gccaacagcgcaacggcactggaagacattccgctaatatcaaaaaactttccgacttctgcctgctgctcgc gtaactgggtttgcacaacctcattcgctttagtcgtgacattatttgccagagcattcaaatcctgattcatgtcg gtattttgaatactggcttttaaaaaggacgtgatcgttccgggggtttgcgttaatacccctggcgcaggcgcg ctcagtgtaggactcaaccccaggtcactgactttactgctgctaataccaatactattcagaatatctttagcgc taacggattgcgaagctgtctgtgaactattctcaacagaatgattatttaaataagcggcgggatttattcccac attactaattaacatatttttctccctttattttggcagtttttatgcgcgactctggcgcagaataaaacgcgaag catccgcatttgctgtaccgcagaagacatggctttttgcagttccgccgttaccttctggttttcaccaaatatt tctacggattgtttaagccactgctgaatctgatccatggcaaaacgggcgagcataaaatcagcaagcgcctcg ctggcatttttaataaatacgccctcggcaacaccaccggctgactgggctgcggtattcgtgacttccatgcc caacgccactttatttagggtattacctaccagctctttacttaaggcattcgtttgcaggcccatcttgctaccca cattacccagaccgctagtaatacgttgcatcccctgggtaaagagtttgctgccgttttgcgccaactgtttca gcacgttaggcaccaacttcttaatcgtttcgcccatcattttgctcagcgcgttacccagtttcgccgccgcgc ctttcccgacaactgcgaccaccacaatgaccgccaccatggcaatagcggcgacaatcgcaccaacaatg ctgccggccatctctgccgttttcttatcgacgcctaatccttccagcgctttggtaatcgccttgccaatcagct ccattaacggcttcagcacatgctccataatcgggtttagcgcctgctgaataaacgacactcccgtcgccgc cttcacaatttcatcggccaccattaccgcaagtcccaccgcagccagcgccagactcgccccaccggtaaa aacagcggccacaacgctgacaatggttagcagcgcgccgaggactttcccgatacatcccataatgcggtt cgtttcctcggctttgcgcgtctcttcctggaattcagccgatttcttttccatctccgcctgacgcccttcctgca aggcgttgaaaagcgcaagatcgttttgcaggctttcttccgtatttttgcccacaatctcaataaacatggccatg agcatagtgaggcgggcgacatttgacagattatcctgctcaccctgggaaacctgattctgagaggcggca ttagccgttccctggaatttggtcagaatgttatccgctttctcggctttcgctttggcgtctgtgcctgctttaac cgtcgcatccgtggccttatctaaggcctctttcgcctctgtcgcttcttttccggcctgttctaccgcggcttcag cttgtgcatagccggggtcagccgggtccagcgattgcaatttattttgcgcctgcgtcagtttttttggtcgcagc gtcataaacactcttggcggtatccgtctttttgatactggcttcatagagatccgtcgcctcctgagcctctccc agagccgtctggaattctttcgatacctgaatccccatctctttttgtgactcaatcatcgcctgccataccgcca gacgagactccagttgagacagcgaaacatcgcccagtagggtcattaacttgccaagcagtaatgtcaattg cccttcgctggagagtttttcccgggcggcgtccgtaggcggctttagacccaccgtattaatagcgctctcgc cggactttgttccggctttaaggtcgcccgctttcgttgccaccacatctttaaaagctttatccgccgcttttaaa aagtccgtgttcttacgaacgccttcaaaagccgcctcagcgaggcgcggatttgggtatatccgctacggc taatgctacttgcgtcatttaccataattattccttttcttgttcactgtgctgctctgtctccgccgtttttagcg cctccagatagaccaacgcttttg (SEQ ID NO: 20) |
| SA(up) 2.5 kbp | ctatcgtgtcatgtaatcttgcatccgatcttgcaacgctgtaaatgtttcgaagccatcctcttctaagaagtgcc ctccatcttccacgattcgcaagttcccctctaatgcattcattaaacgctgggtttctttatatgaaacgtatttg tcatttttagaactcaatccgtaaaaattgtcaactttcttttttaatattatcgtaatcaatggttacattacttaa atcaatatctaaatctatattttctgcatcttctttaaagcccgctatactaaaaaagccttcaatcggctgatcaa tcatttcaatatatttaaagctgtgattgaacctaaaccatgtgttacaaaatatgtatccttttttgcgtacatta |

TABLE 3-continued

Sequences of genetic parts.

| Part | Sequence |
| --- | --- |
| | atttgtttcgtcatagcttcaatccactgatccactgtcttcgcttcaggggattcaaaattaaataatgttacgtc<br>atatccttctaaagttaagttatgctccaaccactgataccaatgatttctactatttccatgcatagaatgtacaa<br>taattacatctgtcatctcattctctcctttcaacttactacttcttttctatttttaaaaaaatgactgattacct<br>ataattgtaaaataaaaacaccttaattagaaatgttatatcgcaaagtgacatttctaattaaagtgtattgtcat<br>catttcaatatcattcaaaaacagctaaacctttgtctctgcttcaatttcacaaaaataattcccgctgaaagtat<br>ctatatttacacattacttccaccattatataacttaaaaatgactatatttcatcaaacattatctaaaggcgtcg<br>cacctacaccaacaccatccaacaattaacttacaactctgcgattacttcttcagcagcaactttaccttgtgtaa<br>tacaatcaggtagtccaaccgcgaccgacatggtactgtggcatacttttcggcaaacgattgacaattgtaaattc<br>aggatcacctttaaatgtcatttcaaaagatgcaccagttactctaagtcgtggatatgtttgtttaatatgtgctt<br>gaatctgtctaatttgttgaatatcatttgacttaaatctctacgtacaatcgatactaattcattatctgtatgat<br>catcaaccacagtatcacctggtttacctacatacgcacgaatcaaaaccttaccttctggtgtagtaaatggccat<br>tttttcgatgtccaagtacatgcggtaatgtctgtatcactcgttctcgcaatcacgaagccagtaccatcataagt<br>attttcaatgtctttttcatcaaatgccaatacaacagttgcaacagtcgtactatccatcgttttaaagtaatcaa<br>atgctggatcttgtccgaaccaattcaaaaagacttgatgcggtgttgtcactaataccccatcgaatacatcttct<br>tgttgattactgtaaacaattttatattgcttttgagatgtaataatatcatccactgacgtattgtagcgtattgt<br>cacacctttatttttcacatcttgttctaatgcttcaataaatgagcttaaaccatgcttaaattgtttgaattgtc<br>cttttggtgcgccaggatataattgtctttgtttcagacgcttatttttctcatccttcataccttttatcagactt<br>ccgaatgcctcttctttttctttaaaattaggaaacgtactcatcaaacttaatttatcaatatcggtaccataaat<br>accacccattaaaggctcaattaagttctcaagtacctcattacctaatcttgctctgaaaaatgcaccaacagaaa<br>tgtcaccatcttgcatttgtataggctttttgattaaatctaatcctgctcttaatttaccaagtggcgatattaat<br>tttgtagtaacaaatggtttaatatctgttggaatacccataattgaaccacctggaatcggatataatttattttt<br>cgcaaaaatatatgattgtccagtcgtatttgtaacaatatcttgttctaatccaatatctttcgctaattctgtca<br>taatcgtttttctacctaaataagattcaggccctagttcaatcatataaccatctttacgatacgattgaatcttt<br>ccccccggacgattcgatgcttcaaagatggttacatcaatattaggatcttgctgttttaa |
| SA(down) 2.5 kbp | gacttgatttcatcaacaattgcaccgataaataatggatgtgtattcggcatttttggacgataataattcgcacc<br>aatatcatcgcaaacaactttacattcataatcattgtcataaagcacctctaaatgctcacatacaaaacctactg<br>gcgtatatataaagttttatactgatgtttttcatataaatcacgtgttaaatcttgtacatctggccctaaccaagg<br>tgtacctgtattaccttcagattgccaaccaatcgcgatatgttcaatattagattgttctttaattaaaagcgcagt<br>atgttctagttcttgtggatatggatcattattcttttcgattaaacctttggcaaactatgtgccgaaacaactaat<br>accgtgtctttatgttcctcttccggtatttgagctaatgtttcgttgactttattcgtccaatattcaataaatttagg<br>ttgttcataataatgtttcacatgtgtaagttgaataccatattttgcagcttcttcatcagcacgtttgtcatatgatc<br>ctactgaaaatgaagaataatgtggtgctagtactaccgtgattgcttcagtaataccatcattgtgcatttgttcaa<br>ccgcatcttcgataaatggtgaaatgtgttttaatcctaagtatagtttaaattcaacatctgcatatgctttatttaat<br>gctgaaactagtgcatcagcttggtcatctgttgtacctgctaatggtgataaaccacctataaattcatatctatc<br>tttcaaatcttgaagttcttcttcagatggacgtttaccatgtctaatatctgtataatatggctctatgtcactttctt<br>tataaggtgtgccataagccataactaataaccccatttttttagtcattgataataccttcctttaaatgaattatctt<br>tcatgtgcttcaatgtaatactatgattatctttgtgtatatgtgtgtacgaattcgcttactttacgtaacgtctctgg<br>ttgcacttctgggaaaacaccgtgtcctaaattaaagatgtgtttaccgttctccataccttgatctaatattggtttc<br>aatctctcttcaatgacattccatggtgctaataaaattgatggatctaaattcccttgtaatgttttagtaacgccta<br>attgttgagcctgattaatagacgttctccaatctaggcctaatacatcaatcggtaaatcattccattcattgatta<br>aatgactggcacctacaccgaataaaattaccggcacatcatgtttttctttaacctcactgattaatcgaatcata<br>tgtggtttaatgtaacgtctgtaatcctcgacatttaatgcacctacccatgaatcgaaaatttgaatcaattcggc<br>acctgcttcgacttgagctgttacatatttaacagatacatcaactaaatgattcattaaagcaaaccatgttgctt<br>catctctatacatcatcgcttttgtaaaattgtaatttttcgatggtccgccttcaatcatatatgacgctaatgtaaat<br>ggtgccccagtaaatcctattagcggcacatttaacttttcttctgttaaaagtttaattgtatctaatacatatggta<br>catctcgttcggggtctatttgagaaagtttctcaacatcttgaattgttttgataggattatgaatcactggaccaa<br>tacccgatttaatttctacatcgacaccaattggctttaatggtgtcataatatctttgtataaaattgctgcatctgt<br>atgataattatcaactggtaaatgtgttacataagcgcacaactccggctgatgtgtaatatcgaatagtgaatat<br>ttttctttcaattttcgatattctggttgcgaacggccagcttgtcgcataaaccaaacaggtgtatgtgatgtttctt<br>cacctttgatcattttttaaaattgtattgtttttattatgcaccataaaggcctcctaaattaaaatcattcttatctat<br>attatcatatcgctcattcgttcgtattttcaataaataaatgtcataaaactgacatttaatcatagaactatttatt<br>gtaaatttaaattctaaagtccattatttgtatcattacttctaaatatctcgcaagattcattatagtaattttaat<br>caattattaatagtggtaatgactagtttatcatcgtataataaataaaaacataaggggacctttcatatgaagaaa<br>ctatatacatcttatggcacttatggattttacatcaaataaaaatcaataacccgacccatcaactattccaatttt<br>cagcatcagatacttcagttattttgaagaaactgatggtgagactgttttaaaatcaccttcaatatatgaagttat<br>taaagaaattggtgaattcagtgaacatcatttctattgtgcaatcttcattccttcaacagaagatcatgcatatcaa<br>cttgaaaagaaactgattagtgtagacgataatttcagaaactttggtggctttaaaagctatcgtttgttaagacct<br>gctaaaggtacaacatataaaatttatttcggatttgctgatcgacatgcatacgaagactttaagcaatctgatg<br>cctttaatgaccatttttcaaaagacgcattaagtcattactttggttcaagcggacaacattcaagttattttgaaa<br>gatatctatacccaataaaagaatag (SEQ ID NO: 22) |
| CD(up) 2.5 kbp | atgaagcaatatatagtcattgggtgtgggagatttggaagttcagttgcgtctactatgcatcttttaggacatc<br>aagtaatggcaatagacaaaaatgaagattcagttcaaagtatatctgacaaggtaacccattcacttatagtgg<br>atgttactgatgagcaagcgttaaggtcattaggtttaggtaactttgatgtagcagtagttgcaataggttctgat<br>ataagggcatctataatggcgactcttatagccaaagaaatgggtgtagagttgataatatgtaaggcaaagg<br>atgaattacaagctaaagtgctttataaaattggcgcagatagagttgtatttccagaaagagatatgggagtaa<br>gagttgcacacaatttagtttcggataatatattagaccatattgaacttgacccagagtattcaattgttgaaatc<br>gtaactccaaatagttgggttggcaagacacttatagagcttgaattaagagctagatatgagataactgtactt<br>gctataaaaacaggtaaaaatataaatgttacaccttctccagatgaggaacttacagcc ggaagtatcctagtt<br>ataatcggtcaaaatactagtataacagcgataacatctggaaataaggggataattagaagaagataatttact<br>atttaatatatatttaattgcaatgaaagtaaagagtatcatataattatgaatagttatatgatactatttttattta<br>atcgaaggtagtatttatttgtaagattagataaagagaagttaaattaaaagtaaggaggctgtgctaatataaaat<br>ttataagttattagcatttagataaaatgattacaaatataaacagtaaggataatgaaaagttaaagtatacaag<br>agcactattaaaatcaaagaataggaataaagagtcaaagttcataatagaaggatacagaatagtaatgcttg<br>cacttgaatgtatggcaaaccttgattatgtatttatcaatgaagaatttgaaaataagaaagaacatgtaaaact |

TABLE 3-continued

Sequences of genetic parts.

| Part | Sequence |
| --- | --- |
| | attagaagatttggataaaaaaaacacaaagatatacaagactactaataaaaactttaaagaattagtggatac<br>agaaaatactcaaggaataataggtgtagtttcatttaagaaaaaaaaattaagtgaaagtataaataaaaaaga<br>taaatttgtattgattttagatagaatacaagacccaggaaatatggggactataataaggactgctgattctgct<br>ggagtagatgccataatagcactaaagggatgtgtcgatatatacaacccaaaagtaattaggtctactatggg<br>ttctatttttgatatgaatataattgatgcttcacaagatgaaactgtggacatgcttaaatcattggattttaatatag<br>tttcaagttacttaaatacagaaaatttttatgacaaaatagattatggttcaaaagtagcattggtgataggaaac<br>gaagcaaatggaataaatgaagaacttgtatcaaagtctgatatttggttaagatacctatatatggtaaagcc<br>gagtcgttaaatgctgcgataagctctgctatactgatgtatgaaataaaaaaatacttaatttaatgtattgtaata<br>aatataatgtcatgttataatcttgaattaaatagtagagtatcaaaaatagtcaatatatattaaaaaaataattaaa<br>ttaattatatattagatgtatatcatataaaaaatgattgagttgattatgtattagatatatattatataaaaaataa<br>ttgagttaattatgcattagatgtatattatataaaaaataattgagttaattatgcattagatatatattatataaaa<br>aataattaaattaattatgtattggatatatattaaaaatagtcacataatttgaatggaaatgatataatactaaaat<br>aaacaatataatattgtaaatgcaatgaaagaggaaagtattttgattaaacttagtaaagagataaacacctaggct<br>gggagtgttttctaagaggtcatgagaagttccctctggagtaacagagctgaaattttacagtaggctttgacg<br>tcaaaaacgcgttaagtttgttagaggtggtttgatgatttttaaattgttaaactactagggtggtaccgcgaaac<br>tata (SEQ ID NO: 23) |
| CD(down) 2.5 kbp | tagacagggattgaggggctttttttatacaaaaaaacgaaagggtgatatgtgtgcaagaaaaattacttgctt<br>tacgtgaagcagctttggctgaaataaaagaagcacaaagcatagaaagtgtagaaagtttaagagttaagta<br>cttaggaaaaaaaggtgagataactgccatacttaaagaaatgggtaaattatctgctgaagaaagaccagta<br>gttggtaaggttgccaatgaggtaagagaaaacattgaacttagcataaattctaaaaaagaagaaataaatgc<br>tattgaaaaagaaagaaaattaaaagaggaagtgatagatgttactcaaccaggaaaagttttaaaggttggg<br>aagaagcatccaataactcaaattatagatgaagtaacagatatatttatcggaatgggattctctatagcagaa<br>gggccagaagttgagactgttgaaaacaactttgacgcattaaacgctcctaaagaccatccatcaagagata<br>tgagcgatacattctatatcaatgatggggtattacttagaactcaaacatctccagttcaagtaagaactatgag<br>aagtcaagagttaccaataaaagtaattgcaccaggtagatgttttaggtcagactcgccagatgctacacact<br>caccaatgttccatcagatagaagggcttgttgttggaaaagatgttactatggcagaatttaaaggaactatgg<br>atatcttcgttgaaaaattgtttggttctgatatcaaaactaagtttagacctcacaacttcccatttacagaaccaa<br>gtgcagaggttgatgttacttgtttcaaatgtggtggtaaaggttgcccaatgtgtaaatatgaaggttggataga<br>aatattaggttcaggtatggttcatccaaatgtgcttagaaattgtggaatagacccagaagtttacagtggattt<br>gcatttggagttggggttgaaagacttgcaatgcttaaatacgaaatagatgatattagattattattcgaaaatg<br>atatgagattcttaaatcaattttaattaggagggtatgtagatgttagtatctttaaaatggcttagagactatgttg<br>atatagacatggatgtaaaagagttcgctgataaaatgacaatgacaggaactaaagttgaaacaatagattat<br>tatggtgaagaaatagaaaatatattggttggaaagatttagaaataaaacaacatccaaatgctgataagttg<br>gttgtaactaaagtagatattggagataaagttgttcaaatagttacaggagctacaaatatatcagaaggagat<br>tatattccagtagctgtaaatggttctaagttacctggaggagttgaaatcaaacagactgatttcagaggtgaat<br>tatcagatggtatgatgtgttcagcagctgaactaggtatagatgaacattacattgaggagtataaaagaggt<br>ggtatatatatttagaccacgaagattcttatgaattaggaaaagatataaaagatgttttaggattaaaagatgc<br>tttaatagattttgaattaacttcaaacagacctgattgtaaatgcatgatgggtatagctagagaagcagctgca<br>actataggaacaaaagtaaaatatcctgaaatcgaagtaaaagaaagtgacgaagagatagatttcaaagttg<br>agatagataatccagatttatgtagaagatatgttgctagaatggttacagatgtaaaaatagaaccttctccata<br>ttggatgcaaagaagacttacagaagcaggagtaagacctataagtaacatagtcgatataacaaacttcgta<br>atgttagagcttggtcaaccacttcatgcttttgatataaatcaagtagagactggaagaatagtagtaagaaat<br>gctaaagatggagagaaacttgtaacattagatgatgttgagagaacattagataaagatatgctagttataaca<br>aatggagaaaaatcacttggtttagctggtgtaatgggtggtgctaactcagaaataacttctaatacgaagact<br>gtacttttgaaagtgccaatttcaaaccagaaaacataagaatgacagctaaaaaagttggtattaggtcagaa<br>gcatcttcaagaaatgaaaaagacttagaccctaatcttgcagagatagcagcaaatagagctgcacaacttgt<br>tgaaatgttaggagcaggaaaagttttaaaaggtgttgtagatgtatatccaaataaaccagaacctaaaaaatt<br>ggtagtaaatcctcaaagaattaaccacctattaggtgtagatgtaccaatggagcagtttgtaggaattttaga<br>atcattagagtttaaatgtaatttggtagctaatgataaattagaaatagatgtaccaagctttagaacagatatgg<br>aacaagaagctgatgtatgggaagaaatagctagaatttatggatttgagaata (SEQ ID NO: 24) |

All plasmids were constructed using *E. coli* DH5α and transformed into *B. subtilis* using MC medium[49]. MC medium is composed of 10.7 g/L potassium phosphate dibasic (Chem-Impex International), 5.2 g/L potassium phosphate monobasic (MilliporeSigma), 20 g/L glucose (MilliporeSigma), 0.88 g/L sodium citrate dihydrate (MilliporeSigma), 0.022 g/L ferric ammonium citrate (MilliporeSigma), 1 g/L Oxoid casein hydrolysate (Thermo Fisher Scientific), 2.2 g/L potassium L-glutamate (MilliporeSigma), and 20 mM magnesium sulfate (MilliporeSigma). Plasmids were extracted from *E. coli* DH5α using Plasmid Miniprep Kit (Qiagen) for transformation of *B. subtilis. B. subtilis* was inoculated into MC medium and incubated at 37° C. for 2 hours. Extracted plasmids were added into *B. subtilis* cell culture and incubated 37° C. for another 4 hours. Transformed *B. subtilis* were selected on the LB agar plate with selective antibiotics. Double crossover was verified for colonies by the replacement of a different antibiotic resistance gene at the integration locus.

DNA Detection Using Cell-Based Sensors

DNA sensor strain was inoculated from the −80° C. glycerol stock into LB medium with 100 μg/mL spectinomycin and incubated at 37° C. with shaking (250 rpm) for 14 hours. On the next day, the OD600 of overnight culture was measured by NanoDrop One (Thermo Fisher Scientific) and diluted to OD0.1 in 1 mL LB in 14 mL Falcon™ Round-Bottom Tube (Thermo Fisher Scientific) supplemented with 50 mM xylose (Thermo Fisher Scientific) and 100 μg/mL spectinomycin (Dot Scientific). Xylose was added to induce the competence. Spectinomycin was added to avoid contamination from other bacteria but it was not required. The sample gDNA was quantified by the Quant-iT dsDNA Assay Kit (Thermo Fisher Scientific) and supplemented in sensor culture with known concentration. The DNA sensor culture was incubated at 37° C. with shaking (250 rpm) for 10 hours for transformation. Culture of transformed sensors (5 μL) was plated onto a 12-well plate (Thermo Fisher Scientific) for selection. In these plates, each well contained 1 mL LB agar supplemented with 2 mM IPTG (Bioline), 5 μg/mL chloramphenicol (MilliporeSigma), and MLS (1 μg/mL erythromycin from Sigma-Aldrich and 25 μg/mL lincomycin from Thermo Fisher Scientific). Antibiotics were used in agar to avoid contamination. GFP-expressing colonies were imaged using Azure Imaging System 300 (Azure Biosystems) using Epi Blue LED Light Imaging with 50 millisecond exposure time. CFU was counted manually. Transformation efficiency is defined as the ratio of CFU on selective plates (transformed *B. subtilis* with GFP expression) to the CFU on non-selective plate (total *B. subtilis*). To count CFU of total *B. subtilis*, cell culture was serially diluted in phosphate-buffered saline (PBS) (Dot Scientific) and plated onto LB agar plate supplemented with 5 μg/mL chloramphenicol and MLS. Since the total *B. subtilis* CFU was similar for most conditions, CFU of transformed cells was used to indicate detection efficiency.

To quantify the sensitivity or specificity of sensors, cell culture was transferred to liquid LB medium with a 1:20 dilution after transformation with serially diluted DNA from 1500 ng/mL to 1 ng/mL. To test the specificity towards gDNA from different strains, 100 ng/mL purified DNA was used for transformation. LB medium was supplemented with 2 mM IPTG (Bioline), 5 μg/mL chloramphenicol (MilliporeSigma), and MLS. Diluted cell culture was transferred to a 96-well black and clear-bottom CELLSTAR® microplate with 100 uL volume in each well (Greiner Bio-One). Plate was sealed with Breathe-Easy Adhesive Microplate Seals (Thermo Fisher Scientific) and incubated in the SPARK Multimode Microplate Reader (TECAN) at 37° C. with shaking for time-series OD600 and GFP measurements. A threshold of GFP fluorescence 400 was used to determine the detection time for different DNA or different concentrations. The threshold was placed in the region of exponential amplification of GFP across all of the conditions where the difference in the detection time between different conditions was not affected much by the choice of threshold. Unpaired t-test was performed to determine if the detection time of specific DNA concentration is different than the background without DNA (N=4). The detection limit is the lowest DNA concentration with a statistical difference. A straight line was fitted to the mean detection time of the four technical replicates with statistical difference versus the logarithmic DNA concentration. DNA mass per mL in detection limit (1 ng, 62.5 ng, 4 ng, and 16 ng) and genome size (4639675 bp, 4857450 bp, 2827820 bp, and 4153430 bp) were converted to chromosome copy number by NEBioCalculator for *E. coli* ($2.10\times10^5$), *S. typhimurium* ($1.25\times10^7$), *S. aureus* ($1.38\times10^6$), and *C. difficile* ($3.75\times10^6$), respectively.

Bioinformatic Analysis of the Specificity of Target DNA

To analyze if the target sequence is conserved for the target species, we searched the 5000 bp of *E. coli* xdhABC, *S. typhimurium* sipBCDA, *S. aureus* hemEH, and *C. difficile* pheST DNA sequence within the same species in NCBI Nucleotide Collection Database. Nucleotide BLAST was optimized for somewhat similar sequences (blastn). The search was specified to taxid 561 for *E. coli*, taxid 28901 for *S. enterica*, taxid 1280 for *S. aureus*, and taxid 1496 for *C. difficile*. Accession date of data is 2022-08-19. For the same strains with target sequence with more than 95% identity similarity and 95% coverage, the percentage is 99% (N=3462), 94.3% (N=2078), 95.6% (N=1488), and 96.4% (N=139) for *E. coli, S. typhimurium, S. aureus*, and *C. difficile*, respectively. To analyze if the target sequence is conserved in other species, the same search was performed excluding the same species. Homologs with varying identity similarity and coverage were found in different species for the target sequences *E. coli* xdhABC (N=5000), *S. typhimurium* sipBCDA (N=117), *S. aureus* hemEH (N=2993), and *C. difficile* pheST(N=5000). Dot plot of homology coverage and identity similarity of each hit were shown for each target sequence.

Multiplexed DNA Detection Using Cell-Based Sensors

Overnight cultures of DNA sensor strains EC-G, ST-R and SA-B were diluted to OD0.1, OD0.1, and OD0.01, respectively, in one single culture containing 1 mL LB supplemented with 50 mM xylose (Thermo Fisher Scientific) and 100 μg/mL spectinomycin (Dot Scientific). Different combinations of gDNA of *E. coli, S. typhimurium*, and *S. aureus* (200 ng/mL each) were added into the mixed culture containing three DNA sensor strains in separate 14 mL Falcon tubes (Thermo Fisher Scientific). The DNA sensor strains were incubated at 37° C. with shaking (250 rpm) for 10 hours and 5 μL of cell culture was plated onto 12-well plates (Thermo Fisher Scientific). In these plates, each well contained 1 mL LB agar supplemented with 2 mM IPTG, 5 μg/mL chloramphenicol, and MLS. Plates were incubated at 37° C. overnight for bacterial growth.

On the next day, each well was imaged using Nikon Eclipse Ti-E Microscope. Brightfield images were collected at 4× magnification using the built-in transilluminator of the microscope. Fluorescence images were collected with the epifluorescence light source X-Cite 120 (Excelitas) and standard band filter cubes including BFP (Excitation: 395/25 nm, Emission: 460/50 nm, Chroma), GFP (Excitation: 470/40 nm, Emission: 525/50 nm, Nikon) and Texas Red (Excitation: 560/40 nm, Emission: 630/70 nm, Nikon) to image BFP, GFP, and RFP, respectively. Pixels were processed with 8×8 binning when taking images. The exposure times for BFP, GFP, RFP were 1.5 ms, 1.5 ms, and 7 ms, respectively. Complete images of each LB agar well were generated from multipoint images after scanning a 24×24 mm area. Once the full images were assembled, each of the four channels were mapped to unity by the minimum and maximum pixel values of all images for that channel using ImageJ. Colonies of different colors were counted manually.

Multiplexed Detection in Complex DNA Samples Using NGS or Cell-Based DNA Sensors Bacterial species *A. caccae, B. thetaiotaomicron, B. longum, C. asparagiforme, S. typhimurium*, and *S. aureus* were inoculated from the −80° C. glycerol stock into YBHI medium and incubated at 37° C. anaerobically overnight. On the next day, cell culture of each strain was diluted to OD0.01 in YBHI (Passage 0) and incubated for 24 hours (Passage 1). Cell culture was diluted to OD0.1 into a fresh YBHI and incubated for another 24 hours (Passage 2). At each passage, cell pellet was collected for DNA extraction using DNeasy Blood & Tissue Kit (Qiagen). To extract *S. aureus* gDNA, 0.1 mg/mL Lysostaphin (MilliporeSigma) was added in the pre-treatment step in combination with enzymatic lysis buffer (Qiagen). Purified DNA was stored at −20° C. before further processing for NGS or cell-based detection.

To use NGS for characterizing microbial community composition, the V3-V4 region of the 16S rRNA gene was PCR amplified from extracted DNA using custom dual-indexed primers on a 96-well PCR plate (detailed method described in Clark et al. Nat. Comm., 2021[50]). PCR products from each well were pooled and purified using DNA Clean & Concentrator kit (Zymo). The resulting library was sequenced on an Illumina MiSeq using a MiSeq Reagent Kit v2 (500-cycle) to generate 2×250 paired-end reads.

Sequencing data were demultiplexed using Basespace Sequencing Hub's FastQ Generation program. Custom python scripts were used for further data processing and sequences were mapped to the 16S rRNA reference database created using consensus sequences from Sanger sequencing data of monospecies cultures. Relative abundance was calculated as the read count mapped to each species divided by the total number of reads of all species.

To use cell-based DNA sensors to detect *S. typhimurium* and *S. aureus* gDNA in the community DNA, 1000 ng/mL extracted community DNA was added to the mixture of SA-G (OD0.1) and ST-R sensors (OD0.1) for the multiplexed detection of *S. typhimurium* and *S. aureus*. The DNA sensor strains were incubated at 37° C. with shaking (250 rpm) for 10 hours and 5 μL of cell culture was plated onto 12-well plates (Thermo Fisher Scientific) containing 1 mL LB agar supplemented with 2 mM IPTG, 5 μg/mL chloramphenicol, and MLS. Plates were incubated at 37° C. overnight for bacterial growth. On the next day, each well was imaged using Nikon Eclipse Ti-E Microscope. Brightfield and fluorescence images of GFP and RFP were collected at 4× magnification using the same procedure described in the previous section for the multiplexed DNA detection. Colony numbers were counted manually. The fold change of mean colony numbers compared to Day 1 was compared with the fold change of relative abundance by NGS results.

Direct Detection of Target Species in the Co-Culture Using Cell-Based Sensors

*E. coli, S. typhimurium*, and *S. aureus* and the corresponding DNA sensor strains were inoculated from the −80° C. glycerol stock into LB medium and incubated at 37° C. with shaking (250 rpm) for 14 hours. *C. difficile* was separately inoculated in YBHI medium and incubated in an anaerobic chamber (Coy Laboratory). On the next day, cell culture of sensor and target strain were diluted to an OD0.1 each in a single culture containing 1 mL LB supplemented with 50 mM xylose with or without 100 μg/mL spectinomycin in 14 mL Falcon tubes (Thermo Fisher Scientific). Overnight culture of target strains (14 hr) was diluted in PBS (Dot Scientific) and plated onto LB agar plates or YBHI agar plates to determine the initial CFU of target bacteria in the co-culture (OD0.1), which was $1.22\times10^{8}$ CFU/mL, $1.07\times10^{8}$ CFU/mL, $3.2\times10^{8}$ CFU/mL, and $1.1\times10^{7}$ CFU/mL for *E. coli, S. typhimurium, S. aureus*, and *C. difficile*, respectively. Sensor and target strains were co-cultured at 37° C. with shaking (250 rpm) for 10 hours, and 5 μL of cell culture was plated onto 12-well plates (Thermo Fisher Scientific). Each well contained 1 mL LB agar supplemented with 2 mM IPTG, 5 μg/mL chloramphenicol, and MLS for the selection of transformed *B. subtilis*. The 12-well plates were incubated overnight at 37° C. On the next day, fluorescent colonies were imaged by Azure Imaging System 300 (Azure Biosystems) using the Epi Blue LED Light Imaging with 50 millisecond exposure time. Colonies with GFP expression were counted manually. To determine if the detection of target bacteria was via transformation, 1 μL (1 unit) DNase I (Thermo Fisher Scientific) was added to the 1 mL co-culture. One unit of DNase I can completely degrade 1 μg of plasmid DNA in 10 min at 37° C. according to the manufacturer's specification.

To improve the detection efficiency, overnight culture of *E. coli* was incubated at 90° C. in digital dry baths/block heaters (Thermo Fisher Scientific) for 10 min and placed on ice for 3 min before being transferred to the sensor culture containing 1 mL LB, 50 mM xylose, and OD0.1 of sensor strain for detection. Spectinomycin was not used in the sensor culture for heat-treated samples. To test the multiplexed detection of *E. coli* and *S. typhimurium* in mice cecal samples, 10 mg cecal samples were first resuspended with 100 μL LB and 50 mM xylose in 1.7 mL Eppendorf tubes (Dot Scientific). Different amounts of overnight culture of *E. coli* and *S. typhimurium* were spiked into cecal samples. The cecal samples were then incubated at 90° C. for 10 min and sat on ice for 3 min before being transferred to the mixed culture of EC-G and ST-R sensors (1 mL LB, 50 mM xylose, OD0.1 of EC-G, and OD0.1 of ST-R) for multiplexed detection. Cecal samples were collected from germ-free mouse experiments following protocols approved by the University of Wisconsin-Madison Animal Care and Use Committee. Briefly, 8-week-old C57BL/6 gnotobiotic male mice (wild-type) were inoculated with 8 human gut bacteria—*Dorea formicigenerans, Coprococcus comes, Anaerostipes caccae, Bifidobacterium longum, Bifidobacterium adolescentis, Bacteroides vulgatus, Bacteroides caccae*, and *Bacteroides* thetaiotaomicron via oral gavage. After four weeks of colonization, mice were euthanized for cecal sample collection. Cecal samples were stored at −80° C. and thawed for the use in multiplexed detection of spike-in *E. coli* and *S. typhimurium.*

REFERENCES

1. Brophy, J. A. N. & Voigt, C. A. Principles of genetic circuit design. *Nature Methods* 11, (2014).
2. Levskaya, A. et al. Engineering *Escherichia coli* to see light. *Nature* 438, 441-442 (2005).
3. Bourdeau, R. W. et al. Acoustic reporter genes for noninvasive imaging of microorganisms in mammalian hosts. *Nature* 553, (2018).
4. You, L., Cox, R. S., Weiss, R. & Arnold, F. H. Programmed population control by cell-cell communication and regulated killing. *Nature* 428, (2004).
5. Danino, T., Mondragón-Palomino, O., Tsimring, L. & Hasty, J. A synchronized quorum of genetic clocks. *Nature* 463, (2010).
6. Liao, M. J., Din, M. O., Tsimring, L. & Hasty, J. Rock-paper-scissors: Engineered population dynamics increase genetic stability. *Science* (80-.). 365, (2019).
7. Saeidi, N. et al. Engineering microbes to sense and eradicate *Pseudomonas aeruginosa*, a human pathogen. *Mol. Syst. Biol.* 7, (2011).
8. Borrero, J., Chen, Y., Dunny, G. M. & Kaznessis, Y. N. Modified lactic acid bacteria detect and inhibit multiresistant enterococci. *ACS Synth. Biol.* 4, (2015).
9. Scott, S. R. & Hasty, J. Quorum Sensing Communication Modules for Microbial Consortia. *ACS Synth. Biol.* 5, (2016).
10. Sexton, J. T. & Tabor, J. J. Multiplexing cell-cell communication. *Mol. Syst. Biol.* 16, (2020).
11. Ibáñez de Aldecoa, A. L., Zafra, O. & González-Pastor, J. E. Mechanisms and regulation of extracellular DNA release and its biological roles in microbial communities. *Front. Microbiol.* 8, 1390 (2017).
12. Johnston, C., Martin, B., Fichant, G., Polard, P. & Claverys, J.-P. Bacterial transformation: distribution, shared mechanisms and divergent control. *Nat. Rev. Microbiol.* 12, 181-196 (2014).
13. Carrasco, B., Serrano, E., Martin-González, A., Moreno-Herrero, F. & Alonso, J. C. *Bacillus subtilis* MutS modulates RecA-mediated DNA strand exchange between divergent DNA sequences. *Front. Microbiol.* (2019). doi: 10.3389/fmicb.2019.00237
14. Popp, P. F., Dotzler, M., Radeck, J., Bartels, J. & Mascher, T. The *Bacillus* BioBrick Box 2.0: Expanding the genetic toolbox for the standardized work with *Bacillus subtilis. Sci. Rep.* 7, (2017).
15. Dubnau, D. Genetic competence in *Bacillus subtilis. Microbiological Reviews* (1991).
16. Ji, M. et al. Engineering *Bacillus subtilis* ATCC 6051a for the production of recombinant catalases. *J. Ind. Microbiol. Biotechnol.* 48, (2021).
17. Zhang, X.-Z. & Zhang, Y.-H. P. Simple, fast and high-efficiency transformation system for directed evolution of cellulase in *Bacillus subtilis. Microb. Biotechnol.* 4, 98-105 (2011).
18. Silvaggi, J. M., Perkins, J. B. & Losick, R. Small untranslated RNA antitoxin in *Bacillus subtilis. J. Bacteriol.* 187, (2005).
19. Maamar, H. & Dubnau, D. Bistability in the *Bacillus subtilis* K-state (competence) system requires a positive feedback loop. *Mol. Microbiol.* (2005). doi:10.1111/j.1365-2958.2005.04592.x
20. Xi, H., Schneider, B. L. & Reitzer, L. Purine catabolism in *Escherichia coli* and function of xanthine dehydrogenase in purine salvage. *J Bacteriol.* 182, (2000).
21. McClelland, M. et al. Complete genome sequence of *Salmonella enterica* serovar *Typhimurium* LT2. *Nature* 413, (2001).
22. Stabler, R. A. et al. Comparative genome and phenotypic analysis of *Clostridium difficile* 027 strains provides insight into the evolution of a hypervirulent bacterium. *Genome Biol.* 10, (2009).
23. Soni, I., Chakrapani, H. & Chopra, S. Draft genome sequence of methicillin-sensitive *Staphylococcus aureus* ATCC 29213. *Genome Announc.* 3, (2015).
24. Tucker, S. C. & Galin, J. E. Complex function for SicA, a *Salmonella enterica* serovar *typhimurium* type III secretion-associated chaperone. *J. Bacteriol.* 182, (2000).
25. Lobo, S. A. L. et al. *Staphylococcus aureus* haem biosynthesis: Characterisation of the enzymes involved in final steps of the pathway. *Mol. Microbiol.* 97, (2015).
26. Beyer, D. et al. New Class of Bacterial Phenylalanyl-tRNA Synthetase Inhibitors with High Potency and Broad-Spectrum Activity. *Antimicrob. Agents Chemother.* 48, (2004).
27. Ibekwe, A. M. & Grieve, C. M. Detection and quantification of *Escherichia coli* O157:H7 in environmental samples by real-time PCR. *J. Appl. Microbiol.* 94, (2003).
28. Jung, B. Y., Suk, C. J. & Chang, H. K. Development of a rapid immunochromatographic strip for detection of *Escherichia coli* O157. *J. Food Prot.* 68, (2005).
29. Serrano, E., Ramos, C., Alonso, J. C. & Ayora, S. Recombination proteins differently control the acquisition of homoeologous DNA during *Bacillus subtilis* natural chromosomal transformation. *Environ. Microbiol.* 23, (2021).
30. Giordano, N. et al. Cysteine desulfurase IscS2 plays a role in oxygen resistance in *Clostridium difficile. Infect. Immun.* 86, (2018).
31. Papagiannopoulou, C., Parchen, R., Rubbens, P. & Waegeman, W. Fast Pathogen Identification Using Single-Cell Matrix-Assisted Laser Desorption/Ionization-Aerosol Time-of-Flight Mass Spectrometry Data and Deep Learning Methods. *Anal. Chem.* 92, (2020).
32. Nißler, R. et al. Remote near infrared identification of pathogens with multiplexed nanosensors. *Nat. Commun.* 11, (2020).
33. Dong, H. & Zhang, D. Current development in genetic engineering strategies of *Bacillus* species. *Microb. Cell Fact.* 13, (2014).
34. Ragheb, M. N., Merrikh, C., Browning, K. & Merrikh, H. Mfd regulates RNA polymerase association with hard-to-transcribe regions in vivo, especially those with structured RNAs. *Proc. Natl. Acad. Sci.* U.S.A 118, (2020).
35. Renda, B. A., Hammerling, M. J. & Barrick, J. E. Engineering reduced evolutionary potential for synthetic biology. *Molecular BioSystems* 10, (2014).
36. Law, J. W. F., Mutalib, N. S. A., Chan, K. G. & Lee, L. H. Rapid methods for the detection of foodborne bacterial pathogens: Principles, applications, advantages and limitations. *Front. Microbiol.* 5, (2014).
37. Rahmer, R., Heravi, K. M. & Altenbuchner, J. Construction of a super-competent *Bacillus subtilis* 168 using the PmtlA-comKS inducible cassette. *Front. Microbiol.* 6, 1431 (2015).
38. Kurushima, J. et al. Unbiased homeologous recombination during pneumococcal transformation allows for multiple chromosomal integration events. Elife 9, (2020).
39. Burian, J. et al. High-throughput retrieval of target sequences from complex clone libraries using CRISPRi. *Nat. Biotechnol.* 2022 1-5 (2022). doi:10.1038/s41587-022-01531-8
40. Gu, W., Miller, S. & Chiu, C. Y. Clinical Metagenomic Next-Generation Sequencing for Pathogen Detection. *Annu. Rev. Pathol. Mech. Dis.* 14, (2019).
41. Liu, F., Li, J., Zhang, T., Chen, J. & Ho, C. L. Engineered Spore-Forming *Bacillus* as a Microbial Vessel for Long-Term DNA Data Storage. *ACS Synth. Biol.* (2022). doi:10.1021/ACSSYNBIO.2C00291/SUPPL_FILE/SB2C00291_SI_001.PDF
42. Gomes, A. L. C. et al. Genome and sequence determinants governing the expression of horizontally acquired DNA in bacteria. *ISME J.* 14, (2020).
43. Beauregard, P. B., Chai, Y., Vlamakis, H., Losick, R. & Kolter, R. *Bacillus subtilis* biofilm induction by plant polysaccharides. *Proc. Natl. Acad. Sci. U.S.A* 110, (2013).
44. Tam, N. K. M. et al. The intestinal life cycle of *Bacillus subtilis* and close relatives. *J. Bacteriol.* (2006). doi:10.1128/JB.188.7.2692-2700.2006
45. Sheth, R. U. & Wang, H. H. DNA-based memory devices for recording cellular events. *Nature Reviews Genetics* (2018). doi:10.1038/s41576-018-0052-8
46. González, L. M., Mukhitov, N. & Voigt, C. A. Resilient living materials built by printing bacterial spores. *Nat. Chem. Biol.* 16, (2020).
47. Cooper, R. M. et al. Engineered bacteria detect tumor DNA in vivo. *bioRxiv* 2021.09.10.459858 (2021). doi:10.1101/2021.09.10.459858
48. Cheng, Y.-Y., Papadopoulos, J. M., Falbel, T., Burton, B. M. & Venturelli, O. S. Efficient plasmid transfer via natural competence in a synthetic microbial community. *bioRxiv* 2020.10.19.342733v2 (2020). doi:10.1101/2020.10.19.342733
49. Konkol, M. A., Blair, K. M. & Kearns, D. B. Plasmid-encoded comi inhibits competence in the ancestral 3610 strain of *Bacillus subtilis. J. Bacteriol.* 195, (2013).
50. Clark, R. L. et al. Design of synthetic human gut microbiome assembly and butyrate production. *Nat. Commun.* 12, (2021).
51. Overkamp, W. et al. Benchmarking various green fluorescent protein variants in *Bacillus subtilis, Streptococcus pneumoniae*, and *Lactococcus lactis* for live cell imaging. *Appl. Environ. Microbiol.* 79, 6481-6490 (2013).
52. Tack, D. S. et al. The genotype-phenotype landscape of an allosteric protein. *Mol. Syst. Biol.* 17, (2021).

53. Prindle, A. et al. Ion channels enable electrical communication in bacterial communities. *Nature* 527, (2015).
54. Miller, M. B. & Bassler, B. L. Quorum sensing in bacteria. *Annual Review of Microbiology* 55, (2001).
55. Du, P. et al. De novo design of an intercellular signaling toolbox for multi-channel cell-cell communication and biological computation. *Nat. Commun.* 11, (2020).
56. Marchand, N. & Collins, C. H. Peptide-based communication system enables *Escherichia coli* to *Bacillus megaterium* interspecies signaling. *Biotechnol. Bioeng.* 110, (2013).
57. Morens, D. M. & Fauci, A. S. Emerging Pandemic Diseases: How We Got to COVID-19. *Cell* 182, (2020).
58. Iqbal, S. S. et al. A review of molecular recognition technologies for detection of biological threat agents. *Biosens. Bioelectron.* 15, (2000).
59. Chiu, C. Y. & Miller, S. A. Clinical metagenomics. *Nature Reviews Genetics* 20, (2019).
60. East-Seletsky, A. et al. Two distinct RNase activities of CRISPR-C2c2 enable guide-RNA processing and RNA detection. *Nature* 538, (2016).
61. Gootenberg J S, Abudayyeh 00, Lee J W, Essletzbichler P, Dy A J, Joung J, Verdine V, Donghia N, Daringer N M, Freije C A, Myhrvold C, Bhattacharyya R P, Livny J, Regev A, Koonin E V, Hung D T, Sabeti P C, Collins J J, Zhang F. Nucleic acid detection with CRISPR-Cas13a/C2c2. *Science.* 2017 Apr. 28; 356(6336):438-442.

We claim:

1. A cell-based DNA sensor comprising a competent cell comprising a genetic circuit, wherein the genetic circuit comprises:

a pair of homology arms in a DNA strand, wherein the homology arms comprise a first homology arm and a second homology arm, the first homology arm is homologous to a first portion of a target DNA, the second homology arm is homologous to a second portion of the target DNA, and the first homology arm and the second homology arm are separated within the DNA strand by an interstitial region of the DNA strand; and a reporter switch and a kill switch, wherein:

the reporter switch comprises a reporter gene and a negative regulator of the reporter gene, wherein the reporter gene comprises a promoter and a coding sequence that are not comprised within the interstitial region of the DNA strand, and wherein the negative regulator of the reporter gene is comprised within the interstitial region of the DNA strand; and the kill switch comprises one or more genetic elements configured for inhibiting growth of the competent cell, wherein at least one of the one or more genetic elements is comprised within the interstitial region of the DNA strand.

2. The DNA sensor of claim 1, wherein the negative regulator of the reporter gene comprises a repressor gene, wherein the repressor gene expresses a repressor that represses expression of the reporter gene.

3. The DNA sensor of claim 1, wherein the reporter gene is a fluorescent or luminescent protein gene.

4. The DNA sensor of claim 1, wherein the interstitial region comprises at least one of a growth inhibitor gene, a positive regulator of a growth inhibitor gene, and a negative regulator of a selectable marker gene.

5. The DNA sensor of claim 1, wherein the kill switch comprises a toxin gene and a repressor gene, wherein the repressor gene expresses an inducible repressor of the toxin gene, and wherein the toxin gene is comprised within the interstitial region.

6. The DNA sensor of claim 1, wherein the kill switch comprises a toxin gene and a positive regulator of the toxin gene, wherein one or both of the toxin gene and the positive regulator of the toxin gene is comprised within the interstitial region.

7. The DNA sensor of claim 1, wherein the kill switch comprises a counter-selectable marker gene comprised within the interstitial region.

8. The DNA sensor of claim 1, wherein the kill switch comprises a selectable marker gene and a negative regulator of the selectable marker gene, wherein the selectable marker gene is not comprised within the interstitial region of the DNA strand, and wherein the negative regulator of the selectable marker gene is comprised within the interstitial region of the DNA strand.

9. The DNA sensor of claim 8, wherein the negative regulator of the selectable marker gene is also the negative regulator of the reporter gene.

10. The DNA sensor of claim 1, wherein the target DNA is native DNA.

11. A composition comprising two or more cell-based DNA sensors, wherein each of the two or more cell-based DNA sensors is a cell-based DNA sensor as recited in claim 1, wherein:

the pairs of homology arms in the two or more cell-based sensors are each homologous to different target DNA sequences; and the reporter genes in the two or more cell-based DNA sensors express reporters that are each detectably different from each other.

12. A method of detecting target DNA with the cell-based DNA sensor of claim 1, the method comprising:

culturing the DNA sensor in a culture medium comprising the target DNA for a time effective to transform the DNA sensor with the target DNA; and detecting the transformed DNA sensor.

13. The method of claim 12, wherein the target DNA is non-isolated cellular DNA.

14. The method of claim 12, wherein the target DNA is non-isolated bacterial DNA.

15. The method of claim 12, wherein the cell-based DNA sensor comprises two or more cell-based DNA sensors, wherein:

the pairs of homology arms in the two or more cell-based sensors are each homologous to different target DNA sequences; and the reporter genes in the two or more cell-based DNA sensors express reporters that are each detectably different from each other.

16. A method of detecting a target cell comprising target DNA with the cell-based DNA sensor of claim 1, the method comprising:

culturing the DNA sensor in a culture medium with the target cell for a time effective to transform the DNA sensor with the target DNA; and detecting the transformed DNA sensor.

17. The method of claim 16, wherein the culturing is performed without lysing the target cell.

18. The method of claim 16, wherein the target cell comprises a bacterium.

19. The method of claim 16, wherein the cell-based DNA sensor comprises two or more cell-based DNA sensors, wherein:

the pairs of homology arms the two or more cell-based sensors are each homologous to different target DNA sequences from different target cells; and the reporter genes in the two or more cell-based DNA sensors express reporters that are each detectably different from each other.

* * * * *